US011780795B2

(12) United States Patent
De Ren et al.

(10) Patent No.: US 11,780,795 B2
(45) Date of Patent: Oct. 10, 2023

(54) CUMENE-PHENOL COMPLEX WITH THERMAL OXIDATION SYSTEM

(71) Applicant: Honeywell International Inc., Charlotte, NC (US)

(72) Inventors: Jan De Ren, Bracknell (GB); David K. Borland, Workingham (GB); Tom Jackson, Surrey (GB); Chad A. Williams, Arlington Heights, IL (US); Cooper W. Bauer, St. Louis, MO (US); William J. Whyman, Tulsa, OK (US)

(73) Assignee: Honeywell International Inc., Charlotte, NC (US)

( * ) Notice: Subject to any disclaimer, the term of this patent is extended or adjusted under 35 U.S.C. 154(b) by 280 days.

(21) Appl. No.: 17/361,690

(22) Filed: Jun. 29, 2021

(65) Prior Publication Data
US 2022/0041534 A1 Feb. 10, 2022

Related U.S. Application Data

(60) Provisional application No. 63/153,447, filed on Feb. 25, 2021, provisional application No. 63/060,804, filed on Aug. 4, 2020.

(51) Int. Cl.
C07C 37/00 (2006.01)
C07C 37/08 (2006.01)
B01D 53/34 (2006.01)
B01D 53/50 (2006.01)
C07F 1/04 (2006.01)
C07C 5/03 (2006.01)
C07C 37/68 (2006.01)
C02F 1/72 (2023.01)
C02F 1/04 (2023.01)

(52) U.S. Cl.
CPC .......... C07C 37/006 (2013.01); B01D 53/343 (2013.01); B01D 53/50 (2013.01); C02F 1/04 (2013.01); C02F 1/72 (2013.01); C07C 5/03 (2013.01); C07C 37/685 (2013.01); B01D 2251/10 (2013.01); B01D 2259/12 (2013.01); C02F 2209/03 (2013.01)

(58) Field of Classification Search
CPC ......... C07C 37/006; C07C 37/08; C07C 5/03; C07F 1/04; B01D 53/343; B01D 53/50
See application file for complete search history.

(56) References Cited

U.S. PATENT DOCUMENTS

| | | |
|---|---|---|
| 3,567,433 A | 3/1971 | Gutnikov |
| 4,377,470 A | 3/1983 | Hettinger, Jr. et al. |
| 4,430,517 A | 2/1984 | Imai et al. |
| 4,514,368 A | 4/1985 | Hubred |
| 4,544,533 A | 10/1985 | Marcantonio |
| 4,762,812 A | 8/1988 | Lopez et al. |
| 5,339,755 A | 8/1994 | Smith |
| 5,365,010 A | 11/1994 | Rao et al. |
| 6,252,124 B1 | 6/2001 | Zakoshansky et al. |
| 6,449,954 B2 | 9/2002 | Bachmann |
| 6,514,904 B1 | 2/2003 | Moser et al. |
| 7,002,048 B2 | 2/2006 | Wijesekera et al. |
| 7,034,192 B2 | 4/2006 | Wijesekera |
| 7,126,029 B2 | 10/2006 | Skipworth et al. |
| 7,141,700 B1 | 11/2006 | Schmidt et al. |
| 7,141,701 B1 | 11/2006 | Schmidt et al. |
| 7,166,752 B2 | 1/2007 | Marshall, Jr. et al. |
| 7,186,866 B1 | 3/2007 | Keenan et al. |
| 7,417,003 B2 | 8/2008 | Schmidt et al. |
| 7,674,739 B2 | 3/2010 | Elomari et al. |
| 7,652,181 B1 | 4/2010 | Schmidt et al. |
| 7,700,511 B2 | 4/2010 | Reynolds et al. |
| 7,740,751 B2 | 6/2010 | Peters |
| 7,744,828 B2 | 6/2010 | Schmidt et al. |
| 7,841,807 B2 | 11/2010 | Naunheimer et al. |
| 7,878,736 B2 | 2/2011 | Naunheimer et al. |
| 7,888,537 B2 | 2/2011 | Schmidt et al. |
| 8,242,320 B2 | 8/2012 | Schmidt et al. |
| 8,329,603 B2 | 12/2012 | Randolph et al. |
| 8,387,645 B2 | 3/2013 | Shafe |
| 8,457,278 B2 | 6/2013 | Fadler |
| 8,518,847 B2 | 8/2013 | Jan et al. |
| 8,608,941 B2 | 12/2013 | Haizmann et al. |
| 8,609,915 B2 | 12/2013 | Majumdere et al. |
| 8,609,916 B2 | 12/2013 | Majumder et al. |
| 8,679,321 B2 | 3/2014 | Negiz et al. |
| 8,853,481 B2 | 10/2014 | Jan et al. |
| 9,006,123 B2 | 4/2015 | Nabozny |
| 9,079,816 B2 | 7/2015 | Johnson et al. |
| 9,138,738 B1 | 9/2015 | Glover et al. |

(Continued)

FOREIGN PATENT DOCUMENTS

| | | |
|---|---|---|
| CA | 2706957 A1 | 6/2009 |
| CN | 101239758 A | 8/2008 |
| EP | 0320094 A2 | 6/1989 |
| EP | 1218890 A2 | 7/2002 |
| WO | 0226680 A1 | 4/2002 |

OTHER PUBLICATIONS

Levy, Edward et al., Recovery of Water from Boiler Flue Gas Using Condensing Heat Exchangers, Final Technical Report issued Jun. 2011, Energy Research Center.
Liu, Xinpeng et al., Desulfurization and regeneration performance of heteropoly compound/ionic liquid solutions at high temperature, Chemical Engineering Journal 316, 2017, 171-178.
International Preliminary Report on Patentability from corresponding PCT application No. PCT/US2021/071068 dated Feb. 7, 2023.
International Search Report from corresponding PCT application No. PCT/US2021/071068 dated Nov. 3, 2021.
Written Opinion from corresponding PCT application No. PCT/US2021/071068 dated Nov. 3, 2021.

Primary Examiner — Sikarl A Witherspoon

(57) ABSTRACT

A process for the treatment of waste water, spent air, and hydrocarbon containing liquid and gaseous streams in the cumene/phenol complex is described. Various effluent streams are combined in appropriate collection vessels, including a spent air knockout drum, a hydrocarbon buffer vessel, a fuel gas knockout drum, a phenolic water vessel, and a non-phenolic water vessel. Streams from these vessels are sent to a thermal oxidation system.

20 Claims, 21 Drawing Sheets

(56) References Cited

U.S. PATENT DOCUMENTS

| | | |
|---|---|---|
| 9,150,469 B2 | 10/2015 | Bullen et al. |
| 9,181,150 B1 | 11/2015 | Smith et al. |
| 9,206,362 B2 | 12/2015 | Haizmann et al. |
| 9,290,826 B2 | 3/2016 | Da Costa et al. |
| 9,302,951 B2 | 4/2016 | Stevens et al. |
| 9,321,783 B2 | 4/2016 | Ibert et al. |
| 9,327,259 B2 | 5/2016 | Hartman et al. |
| 9,328,037 B2 | 5/2016 | Riley et al. |
| 9,359,917 B2 | 6/2016 | Koseoglu et al. |
| 9,360,252 B2 | 6/2016 | Furlong et al. |
| 9,399,604 B2 | 7/2016 | Martins et al. |
| 9,416,321 B2 | 8/2016 | Eizenga et al. |
| 9,469,818 B2 | 10/2016 | Baldriaghi et al. |
| 9,523,050 B2 | 12/2016 | Pandranki et al. |
| 9,567,264 B2 | 2/2017 | Fichtl |
| 9,637,699 B2 | 5/2017 | Ellig et al. |
| 9,718,047 B2 | 8/2017 | Moser et al. |
| 9,745,523 B2 | 8/2017 | Ganguly et al. |
| 9,815,756 B2 | 11/2017 | Schmidt et al. |
| 9,822,314 B2 | 11/2017 | Ray |
| 9,914,675 B2 | 3/2018 | Buchbinder et al. |
| 9,914,880 B2 | 3/2018 | Fichtl et al. |
| 9,914,883 B2 | 3/2018 | Dutta et al. |
| 10,041,004 B2 | 8/2018 | Govindhakannan et al. |
| 10,240,099 B2 | 3/2019 | Mani et al. |
| 10,384,186 B2 | 8/2019 | Egolf et al. |
| 10,399,852 B2 | 9/2019 | De Ren et al. |
| 10,429,066 B2 | 10/2019 | Schröter et al. |
| 10,577,539 B2 | 3/2020 | Brodeur-Campbell et al. |
| 10,577,547 B2 | 3/2020 | Wexler et al. |
| 2008/0188694 A1 | 8/2008 | Schmidt et al. |
| 2013/0087481 A1 | 4/2013 | Heraud et al. |
| 2015/0094486 A1 | 4/2015 | Buchbinder et al. |
| 2016/0168054 A1 | 6/2016 | Kalnes et al. |
| 2019/0144766 A1 | 5/2019 | Yokomizo et al. |
| 2019/0292949 A1 | 9/2019 | Sonnek et al. |
| 2020/0222851 A1 | 7/2020 | De Ren et al. |

CUMENE-PHENOL COMPLEX WITH THERMAL OXIDATION SYSTEM

RELATED APPLICATIONS

This application claims the benefit of U.S. Provisional Patent Application Ser. Nos. 63/060,804 filed on Aug. 4, 2020, and 63/153,447 filed Feb. 25, 2021, the entirety of which are incorporated herein by reference.

BACKGROUND

In general, phenol may be prepared by the air oxidation of cumene and the subsequent sulfuric acid cleavage of the resulting cumene hydroperoxide to form a reaction mixture comprising phenol, acetone and unreacted cumene. In addition to the principal products, there are formed varying amounts of by-products such as mesityl oxide, alpha-methylstyrene, hydroxyacetone, 2-methylbenzofuran, p-cumylphenol, phenyldimethylcarbinol, acetophenone, and higher molecular weight phenols.

In the process of recovering phenol from the acid cleavage reaction mixture, the acidic reaction mixture is initially neutralized, either directly by the addition of a diamine, ammonia, sodium phenate, or caustic, for example, or indirectly by contact with an ion exchange resin. In one embodiment, the neutralized reaction mixture is fed to a distillation column, commonly referred to as a crude acetone column or crude splitter, at conditions to effect a crude separation of those materials boiling below cumene whereby an overhead fraction is recovered comprising substantially all of the acetone and lower boiling by-products, as well as a substantial portion of the water and unreacted cumene. Acetone is subsequently recovered, as is cumene, by the further distillation of the crude acetone column overhead. The resulting recovered cumene is recycled to the oxidation process.

The bottoms fraction recovered from the crude acetone column, comprising phenol and alpha-methylstyrene (AMS), as well as the balance of the water and the bulk of the unreacted cumene, is typically treated for the separation of heavy ends and thereafter fed to a distillation column, commonly referred to as a cumene or alpha-methylstyrene or cumene-alpha-methylstyrene column. The latter column is operated at conditions to separate an overhead fraction comprising water, cumene, alpha-methylstyrene, and an azeotropic concentration of phenol from the higher boiling phenol product. The phenol, recovered as the bottoms fraction, further contains certain impurities, e.g., mesityl oxide, 2-methylbenzofuran and hydroxy acetone, and these impurities are treated and separated from the bottoms fraction to yield a substantially pure phenol product.

The overhead fraction from the cumene-alpha methylstyrene column will invariably comprise a significant amount of phenol, e.g., between 2 and 25 weight percent, as well as cumene and alpha-methylstyrene. This overhead fraction can be caustic extracted to recover the cumene and the alpha-methylstyrene as a water-immiscible organic phase which is then reacted and recycled to the oxidation section as cumene. The phenol is recovered as sodium phenate in the aqueous phase. There is phenol recovery facility in which the aqueous sodium phenate solution is acid treated, and the resulting organic phase sprung phenol is recycled for recovery. The aqueous phase containing dissolved phenol and acidifying agent is extracted with a solvent or stripped with steam for recovery of phenol, followed by necessary treatment for safe disposal.

In another embodiment, the neutralized reaction mixture is fed to a dividing wall distillation column, commonly referred to as a crude splitter, at conditions to effect a crude separation of those materials boiling below cumene whereby an overhead fraction is recovered comprising substantially all of the acetone and lower boiling by-products, as well as a substantial portion of the water and unreacted cumene. Acetone is subsequently recovered, as is cumene, by the further distillation of the crude acetone column overhead. The resulting recovered cumene is recycled to the oxidation process.

The phenol, recovered as the bottoms fraction, further contains certain impurities, e.g., mesityl oxide, 2-methylbenzofuran and hydroxy acetone, and the impurities are treated and separated from the bottoms fraction to yield a substantially pure phenol product.

The sidedraw fraction from the crude splitter will invariably comprise a significant amount of phenol, e.g., between 2 and 25 weight percent, the balance of the water, and the bulk of the unreacted cumene and alpha-methylstyrene. The sidedraw fraction can be caustic extracted to recover the cumene and the alpha-methylstyrene as a water-immiscible organic phase which is then reacted and recycled to the oxidation section as cumene. The phenol is recovered as sodium phenate in the aqueous phase. There is phenol recovery facility in which the aqueous sodium phenate solution is acid treated, and the resulting organic phase sprung phenol is recycled for recovery. The aqueous phase containing dissolved phenol and acidifying agent, is extracted with a solvent or stripped with steam for recovery of phenol, followed by necessary treatment for safe disposal.

Recycle cumene from various sections of the complex may contain small quantities of organic acid compounds which are undesirable in the phenol process unit. This is removed using a caustic wash and a water wash.

The cumene/phenol complex involves a number of process units which produce a variety of effluent streams which must be treated and disposed of.

Therefore, it would be desirable to reduce the number of pieces of equipment in the complex while providing proper treatment of the effluent streams. It would also be desirable to reduce the cost of the chemicals used in treating the effluent streams. It would also be desirable to reduce the complexity of processing and treating the effluent streams.

DETAILED DESCRIPTION

Figure 1:
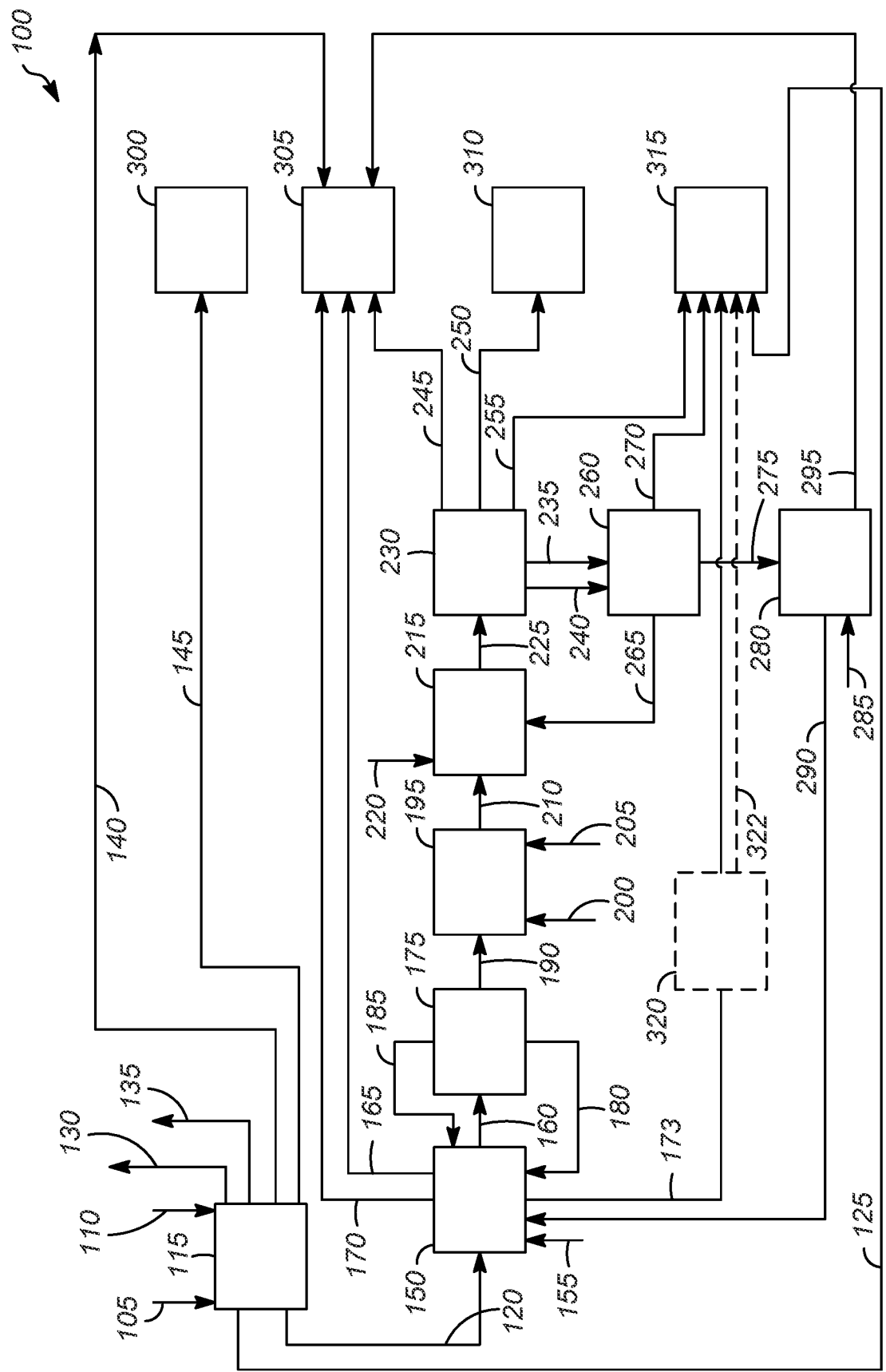
FIG. 1 is an illustration of a cumene/phenol complex using a conventional configuration.

The present invention provides proper treatment of waste water, spent air, and hydrocarbon containing liquid and gaseous streams in the cumene/phenol complex. Various effluent streams from different parts of the cumene/phenol complex are combined in appropriate collection vessels, including for example, one or more of a spent air knockout drum, a hydrocarbon buffer vessel, a fuel gas knockout drum, a phenolic water vessel, and a non-phenolic water vessel. Streams from these vessels are sent to a thermal oxidation system. This allows the elimination of a number of components from the conventional process, including one or more of the waste water treatment plant, the oil extraction column, solvent caustic wash column, spent air adsorbers, solvent drum as well as the associated piping, instrumentation, controls, and mechanical and structural components, reducing both capital costs and operating costs. In addition, the process reduces the cost of treatment chemicals, and the size of certain streams is also reduced.

The effluent streams include both gaseous streams and liquid streams. As used herein, gaseous waste streams have a heating value less than 40 BTU/SCF. Examples of gaseous waste streams include, but are not limited to, the cumene production unit vent gas stream from the cumene production unit, the oxidation spent air stream from the oxidation unit section, the decanter vent stream from the oxidation unit section, and the fractionation hydrocarbon vent stream from the acetone-phenol fractionation unit section. Low calorific value gaseous fuel streams have a heating value greater than 40 BTU/SCF. Examples of low calorific value gaseous fuel streams include, but are not limited to, the propane vent stream from the cumene production unit, the benzene drag stream from the cumene production unit, and the AMS hydrogen vent gas stream from the AMS hydrogenation unit. Liquid waste streams have a heating value less than 2500 Btu/lb. Examples of liquid waste streams include, but are not limited to, the benzene column water stream from the cumene production unit, the peroxide-containing oxidation waste water stream from the oxidation unit section, the peroxide-free oxidation waste water stream from the peroxide destruction unit, the fractionation waste water stream from the acetone-phenol fractionation unit section, and the phenolic waste water stream from the phenol recovery unit section. High calorific value/low selling value liquid streams have a heating value greater than 2500 Btu/lb, and would include streams rich in polynuclear aromatics, asphaltenes, carbon residues, and the like. Examples of high calorific value/low selling value liquid streams include, but are not limited to, the cumene production unit hydrocarbon waste stream from the cumene production unit, and the fractionation organic product stream from the acetone-phenol fractionation unit section. The specific number for the division between a waste stream and a stream having calorific value (low or high) may vary. However, the division allows integration of the process based on the heating value for the stream.

One aspect of the invention is a process for producing phenol. In one embodiment, the process comprises: oxidizing a fresh cumene feed stream in an oxidation unit section to form an oxidation product stream comprising cumene hydroperoxide (CHP), dimethylphenylcarbinol (DMPC), and cumene, and at least one of an oxidation waste water stream, an oxidation spent air stream, and a decanter vent stream; concentrating the oxidation product stream in a CHP concentration unit section to form a concentrated CHP stream and a concentration vent gas stream; decomposing the concentrated CHP stream in a decomposition unit section using a decomposition acid to form an acidic crude product stream comprising phenol, acetone, cumene, and alpha-methylstyrene (AMS); neutralizing the acidic crude product with a neutralization agent in a neutralization unit section to form a neutralized crude product stream; fractionating the neutralized crude product stream in an acetone-phenol fractionation unit section into a fractionation cumene-AMS-phenol stream, and at least one of a fractionation phenolic water stream, a fractionation organic product stream, a fractionation waste water stream, and a fractionation hydrocarbon vent gas stream; separating the fractionation cumene-AMS-phenol stream in a phenol recovery unit section into a cumene-AMS feed stream, and at least one of a recycled sprung phenol stream comprising phenol and cumene, and a phenolic waste water stream; hydrogenating the cumene-AMS feed stream in an AMS hydrogenation unit section to form a MSHP recycled cumene stream; at least one of: introducing at least one of the fractionation organic product stream from the fractionation unit section, a fuel gas knockout drum hydrocarbon liquid stream from a fuel gas knockout drum, and a spent air knockout drum liquid stream from a spent air knockout drum into a hydrocarbon buffer vessel; introducing at least one of an AMS hydrogen vent gas stream from the AMS hydrogenation unit section, a hydrocarbon buffer vessel vent gas stream from the hydrocarbon buffer vessel, a phenolic vent gas stream from a phenolic water vessel, and a non-phenolic vent gas stream from a non-phenolic water vessel into the fuel gas knockout drum; introducing at least one of: the fractionation waste water stream the acetone-phenol fractionation unit section, the phenolic waste water stream from the phenol recovery unit section, and a skimmed water phase from the hydrocarbon buffer vessel into a phenolic water vessel; introducing at least one of the oxidation waste water stream from the oxidation unit section and a benzene column water stream from a cumene production unit into a non-phenolic water vessel; thermally oxidizing one or more of: a mixed hydrocarbon waste stream from the hydrocarbon buffer vessel, a burner fuel gas stream from the fuel gas knockout drum, a phenolic water stream from the phenolic water vessel, and a non-phenolic water stream from the non-phenolic water vessel in a thermal oxidation system. By thermally oxidizing a specified stream, we mean that the thermally oxidizable hydrocarbon, components in the stream are thermally oxidized. For example, with the phenolic or non-phenolic water streams, the thermally oxidizable hydrocarbon components in the phenolic or non-phenolic water streams are thermally oxidized; the water is evaporated.

In some embodiments, thermally oxidizing the one or more of: the mixed hydrocarbon waste stream from the hydrocarbon buffer vessel, the burner fuel gas stream from the fuel gas knockout drum, the spent air stream from the spent air knockout drum, the phenolic water stream from the phenolic water vessel, and the non-phenolic water stream from the non-phenolic water vessel comprises: thermally oxidizing the one or more of: the mixed hydrocarbon waste stream from the hydrocarbon buffer vessel, the burner fuel gas stream from the fuel gas knockout drum, the spent air stream from the spent air knockout drum, the phenolic water stream from the phenolic water vessel, the non-phenolic water stream from the non-phenolic water vessel in a thermal oxidizing section forming a flue gas consisting essentially of at least one of $H_2O$, $CO_2$, $N_2$, $O_2$, SOx, NOx, HCl, $Na_2SO_4$, $Na_2CO_3$, and $Cl_2$; recovering waste heat from the flue gas in a waste heat recovery section; optionally quenching the flue gas in a quench section after recovering the waste heat to form a quenched flue gas consisting essentially of at least one of $H_2O$, $CO_2$, $N_2$, $O_2$, SOx, NOx, HCl, $Na_2SO_4$, $Na_2CO_3$, and $Cl_2$; optionally removing at least one of $Na_2SO_4$, $Na_2CO_3$, SOx, HCl, and $Cl_2$ from the flue gas or the quenched flue gas in a SOx removal section to form a de-SOx outlet flue gas consisting essentially of at least one of $H_2O$, $CO_2$, $N_2$, $O_2$, NOx, wherein removing the at least one of the $Na_2SO_4$, $Na_2CO_3$, SOx, HCl, and $Cl_2$ from the flue gas comprises: contacting a caustic solution or an $NH_3$ based solution with the quenched flue gas in a scrubbing section to form the de-SOx outlet flue gas and a liquid effluent comprising at least one of $H_2O$, $Na_2SO_3$, $Na_2SO_4$, $Na_2HSO_3$, $Na_2CO_3$, NaCl, $(NH_4)_2SO_4$, and $NH_4Cl$; or reacting the flue gas with a reactant in an SOx reaction section to form a reaction section flue gas consisting essentially of at least one of $H_2O$, $CO_2$, $N_2$, $O_2$, NaCl, $Na_2CO_3$, $Na_2SO_4$, $NaNO_3$, $CaCl_2$, $CaSO_4$, $CaCO_3$, $Ca(NO_3)_2$, $MgCl_2$, $MgCO_3$, $MgSO_4$, $Mg(NO_3)_2$, $Cl_2$, and NOx, wherein the reactant comprises $NaHCO_3$, $NaHCO_3 \cdot Na_2CO_3 \cdot 2(H_2O)$, $CaCO_3$, $Ca(OH)_2$, and $Mg(OH)_2$; and optionally filtering the reaction section flue gas in a filter section to remove at least one of NaCl, $Na_2CO_3$, $Na_2SO_4$, $NaNO_3$, $CaCl_2$, $CaSO_4$, $CaCO_3$, $Ca(NO_3)_2$, $MgCl_2$, $MgCO_3$, $MgSO_4$, and $Mg(NO_3)_2$ to form the de-SOx outlet flue gas; optionally removing NOx from the flue gas, the quenched flue gas or the de-SOx outlet flue gas to form a de-NOx outlet flue gas consisting essentially of at least one of $H_2O$, $CO_2$, $N_2$, and $O_2$.

In some embodiments, the process further comprises: providing the recovered waste heat to one or more of: a vaporizer in the CHP concentration unit section, a dehydrator steam heat exchanger in the decomposition unit section, and a reboiler in the acetone-phenol fractionation unit section.

In some embodiments, quenching the flue gas comprises quenching the flue gas with at least one of: air, de-SOx outlet flue gas, de-NOx outlet flue gas, and water.

In some embodiments, the water comprises a water stream from the non-phenolic water vessel or an outside water stream.

In some embodiments, the process further comprises: introducing a water wash waste stream from the phenol recovery unit section and the phenolic waste water stream from the phenol recovery unit section into the phenolic water vessel.

In some embodiments, the process further comprises: introducing at least one of: the oxidation spent air stream from the oxidation unit section, the decanter vent stream from the oxidation unit section, the concentration vent gas stream from the CHP concentration unit section, and the fractionation hydrocarbon vent gas stream from the acetone-phenol fractionation unit section into the spent air knockout drum; optionally preheating a spent air stream from the spent air knockout drum; and thermally oxidizing the spent air stream from the spent air knockout drum in the thermal oxidation system.

In some embodiments, oxidizing the fresh cumene feed stream in the oxidation unit section to form the oxidation product stream comprises: passing the fresh cumene feed and an oxidation air feed stream to at least one oxidation reactor to form the oxidation product stream and an oxidation spent air stream; cooling the oxidation spent air stream in an oxidizer vent gas cooler before introducing the oxidation spent air stream into a spent air knockout drum, and forming a condensate stream; passing the condensate stream to a decanter vessel and forming the decanter vent stream, the oxidation waste water stream, and a decanter cumene recycle stream; washing the decanter cumene recycle stream with a recycle cumene wash water stream and a recycle cumene wash caustic stream in a cumene feed wash column to form a washed cumene stream and a recycle cumene wash water waste stream; passing the washed cumene stream to the oxidation reactors; passing the recycle cumene wash water waste stream to the non-phenolic water vessel; and optionally at least one of passing the MSHP recycle cumene stream from the AMS hydrogenation unit section to the cumene feed wash column and passing a concentration section recycle cumene stream from the CHP concentration unit section to the cumene feed wash column.

In some embodiments, the process further comprises at least one of: recycling a concentration section recycled cumene stream from the CHP concentration unit section to the oxidation unit section; recycling the concentration vent gas stream from the CHP concentration unit section to the oxidation unit section; recycling the recycled sprung phenol stream from the phenol recovery unit section to the neutralization unit section; and passing the oxidation waste water stream to a peroxide destruction section to convert peroxides in the oxidation waste water stream to at least one of alcohols, ketones, aldehydes, organic acids and water to form a peroxide-free oxidation waste water stream before introducing the peroxide-free oxidation waste water stream into the non-phenolic water vessel.

In some embodiments, the process further comprises: reacting propylene and benzene in a cumene production zone to produce the cumene feed stream, and at least one of: a cumene production unit hydrocarbon waste stream, a propane vent stream, a benzene drag stream, and a cumene production unit vent gas stream; and at least one of: introducing the cumene production unit hydrocarbon waste stream into the hydrocarbon buffer vessel; introducing at least one of: the propane vent stream and the benzene drag stream into the fuel gas knockout drum; and introducing the cumene production unit vent gas stream into the spent air knockout drum.

In some embodiments, the process further comprises: preheating at least one of the phenolic water stream from the phenolic water vessel, and the non-phenolic water stream from the non-phenolic water vessel before thermally oxidizing the at least one of the spent air stream, the phenolic water stream, and the non-phenolic water stream using at least one of the recovered waste heat from the thermal oxidation system and a low pressure steam stream from the cumene production unit.

In some embodiments, the process further comprising: controlling a pressure in at least one of the hydrocarbon buffer vessel, the phenolic water vessel, and the non-phenolic water vessel in a push-pull system by introducing at least one of fuel gas, liquefied petroleum gas, and waste gas into the at least one of the hydrocarbon buffer vessel, the phenolic water vessel, and the non-phenolic water vessel; and sending excess at least one of the fuel gas, liquefied petroleum gas, and waste gas to the fuel gas knockout drum.

In some embodiments, the phenolic water stream is atomized and injected into a burner flame in the thermal oxidizer section and wherein the non-phenolic water is injected at a position downstream of the burner flame.

Another aspect of the invention comprises a process for producing phenol. In one embodiment, the process comprises: reacting propylene and benzene in a cumene production zone to produce a fresh cumene feed stream, and at least one of: a cumene production unit hydrocarbon waste stream, a benzene column water stream, a propane vent stream, a benzene drag stream, and a cumene production unit vent gas stream; oxidizing the fresh cumene feed stream in an oxidation unit section to form an oxidation product stream comprising cumene hydroperoxide (CHP), dimethylphenylcarbinol (DMPC), and cumene, and at least one of an oxidation waste water stream, an oxidation spent air stream, and a decanter vent stream; concentrating the oxidation product stream in a CHP concentration unit section to form a concentrated CHP stream and a concentration vent gas stream; decomposing the concentrated CHP stream in a decomposition unit section using a decomposition acid to form an acidic crude product stream comprising phenol, acetone, cumene, and AMS; neutralizing the acidic crude product with a neutralization agent in a neutralization unit section to form a neutralized crude product stream; fractionating the neutralized crude product stream in a acetone-phenol fractionation unit section into a fractionation cumene-AMS-phenol stream, and at least one of a fractionation phenolic water stream, a fractionation organic product stream, a fractionation waste water stream, and a fractionation hydrocarbon vent gas stream; separating the fractionation cumene-AMS-phenol stream in a phenol recovery unit section into a cumene-AMS feed stream, and at least one of a recycled sprung phenol stream comprising phenol and cumene, and a phenolic waste water stream; recycling the recycled sprung phenol stream to the neutralization unit section; hydrogenating the cumene-AMS feed stream in an AMS hydrogenation unit section to form a MSHP recycled cumene stream and an AMS hydrogen vent stream; at least one of: introducing at least one of the fractionation organic product stream from the fractionation unit section, the cumene production unit hydrocarbon waste stream from the cumene production unit, a fuel gas knockout drum hydrocarbon liquid stream from a fuel gas knockout drum, and a spent air knockout drum liquid stream from a spent air knockout drum into a hydrocarbon buffer vessel; introducing at least one of the AMS hydrogen vent gas stream from the AMS hydrogenation unit section, the propane vent stream from the cumene production unit, the benzene drag stream from the cumene production unit, a hydrocarbon buffer vessel vent gas stream from the hydrocarbon buffer vessel, a phenolic vent gas stream from a phenolic water vessel, and a non-phenolic vent gas stream from a non-phenolic water vessel into the fuel gas knockout drum; introducing at least one of: the fractionation waste water stream the acetone-phenol fractionation unit section, the phenolic waste water stream from the phenol recovery unit section, and a skimmed water phase from the hydrocarbon buffer vessel into the phenolic water vessel; introducing at least one of: the oxidation waste water stream from the oxidation unit section and a benzene column water stream from the cumene production unit into the non-phenolic water vessel; thermally oxidizing one or more of: a mixed hydrocarbon waste stream from the hydrocarbon buffer vessel, a burner fuel gas stream from the fuel gas knockout drum, a phenolic water stream from the phenolic water vessel, a non-phenolic water stream from the non-phenolic water vessel in a thermal oxidation system, comprising: thermally oxidizing the one or more of: the mixed hydrocarbon waste stream from the hydrocarbon buffer vessel, the burner fuel gas stream from the fuel gas knockout drum, the spent air stream from the spent air knockout drum, the phenolic water stream from the phenolic water vessel, the non-phenolic water stream from the non-phenolic water vessel in a thermal oxidizing section forming a flue gas consisting essentially of at least one of $H_2O$, $CO_2$, $N_2$, $O_2$, SOx, NOx, HCl, $Na_2SO_4$, $Na_2CO_3$, and $Cl_2$; recovering waste heat from the flue gas in a waste heat recovery section; optionally quenching the flue gas in a quench section after recovering the waste heat to form a quenched flue gas consisting essentially of at least one of $H_2O$, $CO_2$, $N_2$, $O_2$, SOx, NOx, HCl, $Na_2SO_4$, $Na_2CO_3$, and $Cl_2$; optionally removing at least one of $Na_2SO_4$, $Na_2CO_3$, SOx HCl, and $Cl_2$ from the flue gas or the quenched flue gas in a SOx removal section to form a de-SOx outlet flue gas consisting essentially of at least one of $H_2O$, $CO_2$, $N_2$, $O_2$, NOx, wherein removing the $Na_2SO_4$, $Na_2CO_3$, HCl, $Cl_2$, SOx from the flue gas comprises: contacting a caustic solution or an $NH_3$ based solution with the quenched flue gas in a scrubbing section to form the de-SOx outlet flue gas and a liquid effluent comprising at least one of $H_2O$, $Na_2SO_3$, $Na_2SO_4$, $Na_2HSO_3$, $Na_2CO_3$, NaCl, $(NH_4)_2SO_4$, and $NH_4Cl$; or reacting the flue gas with a reactant in an SOx reaction section to form a reaction section flue gas consisting essentially of at least one of $H_2O$, $CO_2$, $N_2$, $O_2$, NaCl, $Na_2CO_3$, $Na_2SO_4$, $NaNO_3$, NOx, $CaCl_2$, $CaSO_4$, $CaCO_3$, $Ca(NO_3)_2$, $MgCl_2$, $MgCO_3$, $MgSO_4$, $Mg(NO_3)_2$, $Cl_2$, and NOx, wherein the reactant comprises $NaHCO_3$, $NaHCO_3 \cdot Na_2CO_3 \cdot 2(H_2O)$, $CaCO_3$, $Ca(OH)_2$, and $Mg(OH)_2$; and optionally filtering the reaction section flue gas in a filter section to remove at least one of NaCl, $Na_2CO_3$, $Na_2SO_4$, $NaNO_3$, $CaCl_2$), $CaSO_4$, $CaCO_3$, $Ca(NO_3)_2$, $MgCl_2$, $MgCO_3$, and $MgSO_4$, to form the de-SOx outlet flue gas; optionally removing NOx from the flue gas, the quenched flue gas, or the de-SOx outlet flue gas to form de-NOx outlet flue gas consisting essentially of at least one of $H_2O$, $CO_2$, $N_2$, and $O_2$.

In some embodiments, the process further comprises: introducing at least one of: the oxidation spent air stream from the oxidation unit section, the decanter vent stream from the oxidation unit section, the concentration vent gas stream from the CHP concentration unit section, the fractionation hydrocarbon vent gas stream from the acetone-phenol fractionation unit section, and the cumene production unit vent gas stream from the cumene production unit into the spent air knockout drum; optionally preheating a spent air stream from the spent air knockout drum; and thermally oxidizing the spent air stream from the spent air knockout drum in the thermal oxidation system.

In some embodiments, the process further comprises: providing the recovered waste heat to one or more of: a vaporizer in the CHP concentration unit section, a dehydrator steam heat exchanger in the decomposition unit section, and a reboiler in the acetone-phenol fractionation unit section.

In some embodiments, the process further comprises at least one of: introducing a water wash waste stream from the phenol recovery unit section and the phenolic waste water stream from the phenol recovery unit section into the phenolic water vessel; and introducing at least one of: the oxidation spent air stream from the oxidation unit section, the decanter vent stream from the oxidation unit section, the concentration vent gas stream from the CHP concentration unit section, and the fractionation hydrocarbon vent gas stream from the acetone-phenol fractionation unit section into the spent air knockout drum.

In some embodiments, the process further comprises: preheating at least one of the phenolic water stream from the phenolic water vessel, and the non-phenolic water stream from the non-phenolic water vessel before thermally oxidizing the at least one of the spent air stream, the phenolic water stream, and the non-phenolic water stream using at least one of the recovered waste heat from the thermal oxidation system and a low pressure steam stream from the cumene production unit.

In some embodiments, the process further comprises: controlling a pressure in at least one of the hydrocarbon buffer vessel, the phenolic water vessel, and the non-phenolic water vessel in a push-pull system by introducing at least one of fuel gas, liquefied petroleum gas, and waste gas into the at least one of the hydrocarbon buffer vessel, the phenolic water vessel, and the non-phenolic water vessel; and sending excess at least one of the fuel gas, liquefied petroleum gas, and waste gas to the fuel gas knockout drum.

In some embodiments, the phenolic water stream is atomized and injected into a burner flame or directly downstream of the calculated flame length in the thermal oxidizer section. The flame length will typically be between 5% and 50% of the total thermal oxidizer chamber (firebox) length. The calculated flame length can be calculated using known methods (e.g., Flame Length and its Heat Radiation, Yagi, Bull. Chem. Soc. JP, 1949, Vol. 22, No. 3, p. 97-104) or determined using known computational fluid dynamic (CFD) modeling (e.g., A Computational Flame Length Methodology for Propane Jet Fires, Cumber and Spearpoint, Fire Safety J., Vol. 3, April 2006, p. 215-228; Structure & Calculation of a Gas Flame, Kryzhanovsky and Kryzhanovsky, 2012, Ukraine; An Experimental Study of Flame Lengths and Emissions of Fully-Modulated Diffusion Flames, Usowicz, Master's Thesis, Worcester Polytechnic Institute, May, 2001). The non-phenolic water is injected at a position downstream of the calculated atomization and evaporation distance of the phenolic water. The atomization and evaporation distance can be calculated using known CFD modeling. Typical atomization and evaporation distances expressed as time are in the range of about 0.05 sec to about 0.5 sec, or about 0.15 sec to about 0.25 sec.

FIG. 1 illustrates a conventional configuration for a cumene/phenol complex 100.

A propylene feed stream 105 and a benzene stream 110 are sent to the cumene production unit 115 where the benzene is alkylated with the propylene to form cumene. The propylene feed stream 105 comprises propylene and propane (e.g., greater than 60% propylene with the remainder being propane). The benzene stream 110 typically contains at least 80 wt % benzene with the balance being $C_5$-$C_7$ non-aromatics.

Suitable alkylation catalysts include solid acid catalysts and preferably a solid oxide zeolite. Examples include, but are not limited to, zeolite beta, zeolite X, zeolite Y, mordenite, faujasite, zeolite omega, UZM-8, MCM-22, MCM-36, MCM-49 and MCM-56. Typical operating conditions include: a temperature of the alkylation reactor is in the range of 100° C. to 310° C. (212° F. to 590° F.), or 120° C. to 280° C. (248° F. to 536° F.); and a pressure in the range of 800 to 5100 kPa (116 to 740 psia), or about 1000 to 3900 kPa (145 to 565 psia). Alkylation reactors, operating conditions and catalysts are known in the art and not further discussed here.

Effluents from the cumene production unit 115 include the cumene stream 120, benzene column water stream 125, propane vent stream 130, benzene drag stream 135, cumene production unit vent gas stream 140, and cumene production unit hydrocarbon waste stream 145.

The cumene stream 120, which comprises greater than 99.9 wt % cumene with the remainder being other $C_8$-$C_9$ aromatics, is sent to the oxidation unit section 150. Cumene can be oxidized to cumene hydroperoxide (CHP) by direct liquid phase oxidation of the cumene with oxidation gas stream 155, which can be oxygen or an oxygen-containing gas such as air, usually at an elevated temperature. Temperatures for the oxidation reaction range from about room temperature to about the boiling point of cumene, (about 152° C. (305° F.)), and pressures range from about atmospheric to about 3.4 MPa(g) (500 psig).

The oxidation product stream 160 comprises comprising cumene hydroperoxide (CHP), dimethylphenylcarbinol (DMPC), and unreacted cumene. Other effluents from the oxidation unit section 150 include oxidation spent air stream 165, decanter vent stream 170, and peroxide-containing oxidation waste water stream 173.

The oxidation product stream 160 is transferred to a CHP concentration unit section 175 where the CHP concentration is raised to a level of about 80 to 85 wt % to form the concentrated CHP stream 190. The concentration section recycle cumene stream 180 comprising unconverted cumene and small amounts of CHP is recycled to the oxidation unit section 150. A concentration vent gas stream 185 from the CHP concentration unit section 175 can be recycled to the oxidation unit section 150.

The concentrated CHP stream 190 is sent to the decomposition unit section 195. In the decomposition unit section 195, the concentrated CHP is decomposed into phenol and acetone using a decomposition acid 200 and water 205. The decomposition acid 200 can be a liquid acid such as $H_2SO_4$ or a gas such as $H_2S$. CHP decomposition is a very exothermic reaction which is normally carried out on a commercial scale in continuous stirred or back-mixed reactors. In such reactors only a small fraction of CHP is unreacted at any given time. The reaction medium consists essentially of the products of decomposition of CHIP, i.e., phenol and acetone, plus any solvent (e.g., cumene) and other materials added with CHP to the reactor. In the presence of the decomposition acid, the DMPC formed during cumene oxidation dehydrates to alphamethylstyrene (AMS), a useful by-product.

The acidic crude product stream 210 comprising phenol, acetone, unreacted cumene, and AMS is sent to the neutralization unit section 215 where it is contacted with a neutralization agent 220. Suitable neutralization agents 220 include, but are not limited to, amines, such as 2-methylpentamethylenediamine (Dytek), hexamethylenediamine, triethylenetetramine, diethylenetriamine, sodium phenate, ammonia, and sodium hydroxide.

The neutralized crude product stream 225 is sent to the acetone-phenol fractionation unit section 230. A fractionation cumene-AMS-phenol stream 235 comprising cumene, AMS, and phenol, is formed. Other streams including a fractionation phenolic water stream 240, a fractionation hydrocarbon vent gas stream 245, a fractionation organic product stream 250, and a fractionation waste water stream 255, may also be formed.

The fractionation cumene-AMS-phenol stream 235 and the fractionation phenolic water stream 240 are sent to the phenol recovery unit section 260 where further separation occurs. A recycled sprung phenol stream 265, a final phenolic waste water stream 270, and a cumene-AMS feed stream 275. The recycled sprung phenol stream 265 comprising phenol, unreacted cumene, and water can be recycled to the neutralization unit section 215.

The cumene-AMS feed stream 275 comprising cumene and AMS is sent to the AMS hydrogenation unit section 280. AMS is reacted with a hydrogen stream 285 to hydrogenate the AMS. A MSHP (methyl styrene hydrogenation process) recycled cumene stream 290 comprising cumene and 0-0.1 wt % AMS is recycled to the oxidation unit section 150. An AMS hydrogen vent gas stream 295 is also formed, The cumene/phenol complex 100 includes a number of units to treat various streams from different units in the complex.

The cumene production unit hydrocarbon waste stream 145 from the cumene production unit 115 comprises diphenyl propane and $C_{15+}$ aromatics. The cumene production unit hydrocarbon waste stream 145 is sent to an organic waste storage vessel 300.

The cumene production unit vent gas stream 140 from the cumene production unit 115, which comprises $N_2$ saturated in cumene at cooling water temperature (e.g., about 3 mol % cumene, 4.5 mol % $O_2$ with the balance being $N_2$ at the cooling temperature e.g., 35° C.), is sent to a thermal oxidizer 305.

Oxidation spent air stream 165 and decanter vent stream 170 from the oxidation unit section 150 are also sent to the thermal oxidizer 305. The oxidation spent air stream 165 comprises $N_2$, $O_2$, and cumene (e.g., about 1-7 mol % $O_2$ with the balance being $N_2$, and the stream is saturated with cumene at nominal 5° C. (range 2-10° C.) (i.e., 0.1 mol %). The decanter vent stream 170 comprises $N_2$, $O_2$, and cumene (e.g., about 1-7 mol % $O_2$ with the balance being $N_2$, and the stream is saturated with cumene at nominal 35° C. (range 20-35° C.) (i.e., 0.1 mol %).

The fractionation hydrocarbon vent gas stream 245 from the acetone-phenol fractionation unit section 230 is sent to the thermal oxidizer 305. The fractionation hydrocarbon vent gas stream 245 comprises $N_2$ (e.g., greater than 99 mol % $N_2$ and 0-1 mol % phenol and acetone).

The AMS hydrogen vent gas stream 295 from the AMS hydrogenation unit section 280 is sent to the thermal oxidizer 305. The AMS hydrogen vent gas stream 295 comprises $H_2$ and methane (e.g., 80-100 mol % $H_2$, 0-0.1 mol % cumene, balance is methane, ethane, and $N_2$).

The cumene/phenol complex has a waste water treatment plant 315 to treat and remove contaminants from the process water. The benzene column water stream 125 from the cumene production unit 115, the fractionation waste water stream 255 from the acetone-phenol fractionation unit section 230, the final phenolic waste water stream 270 from the phenol recovery unit section 260, and the peroxide-containing oxidation waste water stream 173 from the oxidation unit section 150 or the peroxide-free oxidation waste water stream 322 from the peroxide destruction unit section 320 are sent to the waste water treatment plant 315.

The fractionation waste water stream 255 from the acetone-phenol fractionation unit section 230 comprises water, caustic, and acetone (e.g., 0-30 wppm phenol, 0-2 wt % caustic, 100-1000 wppm acetone, and 0-500 wppm cumene) is sent to the waste water treatment plant.

The final phenolic waste water stream 270 from the phenol recovery unit section 260 comprises water, phenol, and salts (e.g., 10-100 wppm phenol, 10-25 wt % sodium sulfate, with the balance being water).

The peroxide-containing oxidation waste water stream 173 from the oxidation unit section 150 comprises water, CHP, and caustic (e.g., 0-2000 wppm total peroxides, 300 wppm cumene, 0.1 wt % caustic, and remainder water). The peroxide-containing oxidation waste water stream 173 can be sent directly to the waste water treatment plant 315 (solid line). In some embodiments, the peroxide-containing oxidation waste water stream 173 can be sent to an optional peroxide destruction unit section 320 where peroxides in the peroxide-containing oxidation waste water stream 173 are converted to alcohols, ketones, aldehydes, organic acids and water. In this case, the peroxide-free oxidation waste water stream 322 from the peroxide destruction unit section 320 is sent to the waste water treatment plant 315 (dotted line).

The benzene column water stream 125 from the cumene production unit 115 comprises water saturated in benzene (e.g., 1100-1900 wppm benzene at the cooling temperature e.g., 35° C.).

The propane vent stream 130 from the cumene production unit 115 comprises propane saturated in benzene (e.g., 45 wt % propane with 25 wt % benzene, 11 wt % non-aromatics, and 4 wt % ethane at 35° C.), and it is sent to the relief header.

The benzene drag stream comprises benzene and $C_5$-$C_7$ non-aromatics (e.g., 40-90 wt % benzene and the balance being $C_5$-$C_7$ non-aromatics). The higher the purity of the benzene stream 110, the lower the drag rate of the benzene drag stream 135. The benzene drag stream 135 can be sent for benzene recovery in an aromatics complex, for example, or to the gasoline pool.

The fractionation organic product stream 250 from the acetone-phenol fractionation unit section 230, which comprises organic residue (e.g., 0-5 wt % phenol, 2-20 wt % acetophenone, balance unidentified heavies), is sent to product storage unit 310. It is typically burned; in some cases, it is mixed with fuel oil prior to being burned.

Figure 2:
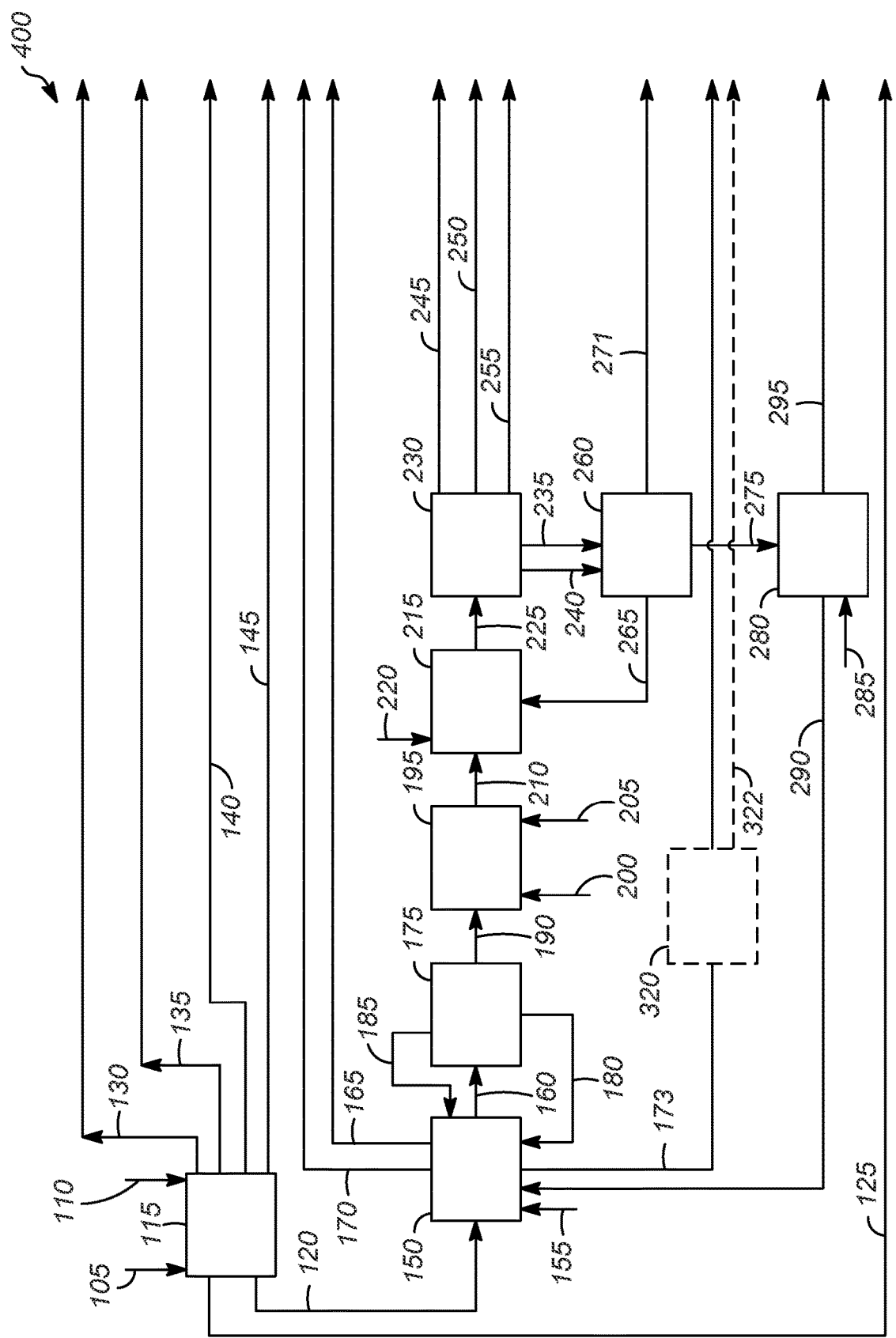
FIG. 2-3 are an illustration of a cumene/phenol complex according to the present invention.
Figure 3:
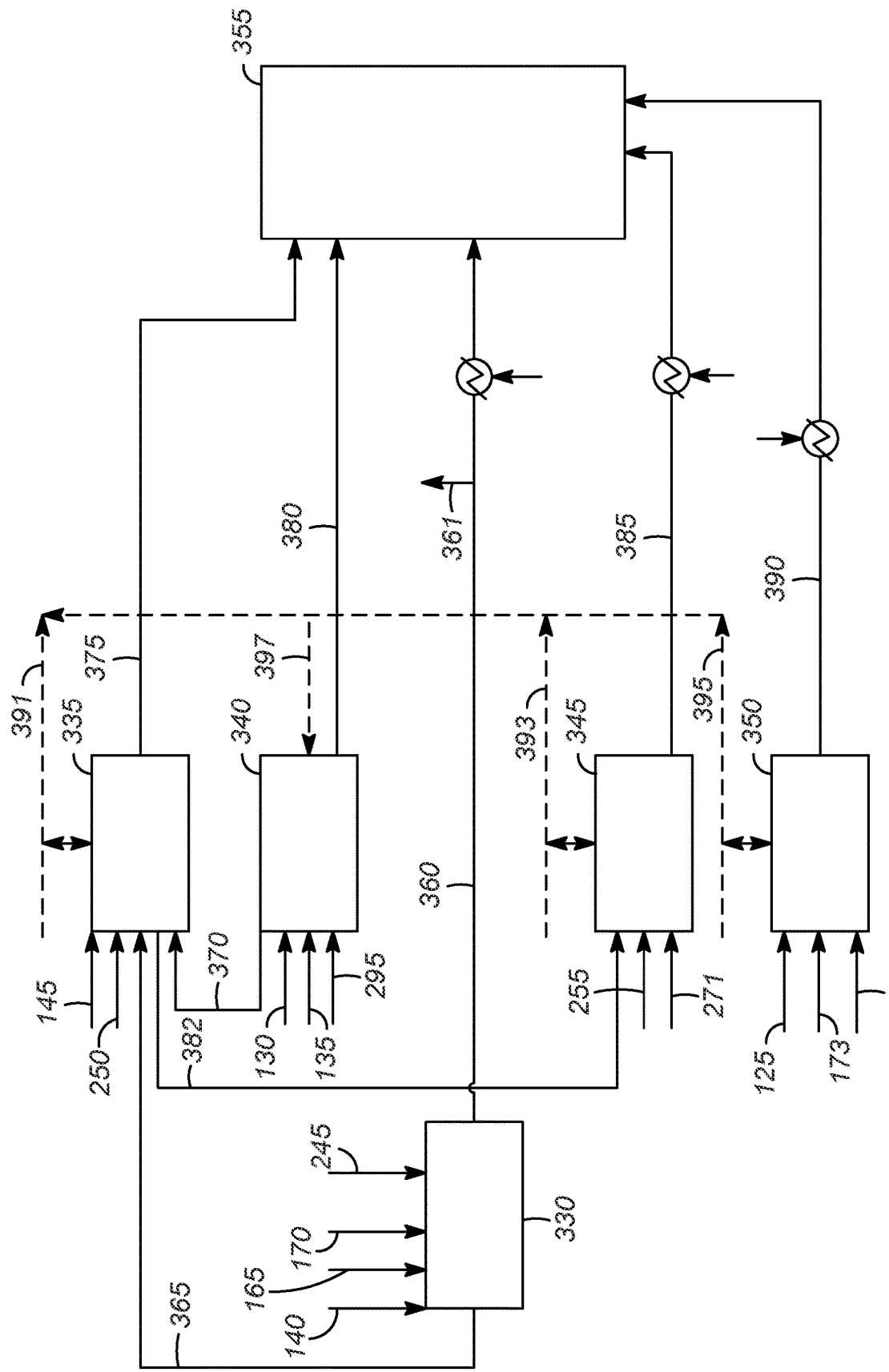

FIGS. 2-3 illustrates an example of a cumene/phenol complex 325 of the present invention. Various parts of the cumene/phenol complex 325 are as described above, including the cumene production unit 115, the oxidation unit section 150, the CHP concentration unit section 175, the decomposition unit section 195, the neutralization unit section 215, the acetone-phenol fractionation unit section 230, the phenol recovery unit section 260, the AMS hydrogenation unit section 280, the peroxide destruction unit section 320, and the product storage unit 310.

This process requires less make-up chemicals than the process of FIG. 1. For example, the amount of make-up sodium hydroxide and sulfuric acid in the phenol recovery unit section 260 is reduced because the first phenolic waste water stream 271 is sent to the phenolic water vessel 345 and then to the thermal oxidation system. The first phenolic waste water stream 271 has a higher phenolic content than final phenolic waste water stream 270 in FIG. 1, as will be shown below in FIG. 6-7. In addition, the process also has a reduced first phenolic waste water stream 271 compared to the process of FIG. 1.

However, as shown in FIG. 3, the process includes a spent air knockout drum 330, a hydrocarbon buffer vessel 335, a fuel gas knockout drum 340, a phenolic water vessel 345, a non-phenolic water vessel 350, and a thermal oxidation system 355.

The spent air knockout drum 330 contains at least one of: the cumene production unit vent gas stream 140 from the cumene production unit, the oxidation spent air stream 165 from the oxidation unit section 150, the decanter vent stream 170 from the oxidation unit section 150, and the fractionation hydrocarbon vent gas stream 245 from the acetone-phenol fractionation unit section 230. A spent air stream 360 from the spent air knockout drum 330 is sent to the thermal oxidation system 355. There can be a cold spent air drag stream 361 from the spent air stream 360.

The hydrocarbon buffer vessel 335 contains at least one of the cumene production unit hydrocarbon waste stream 145 from the cumene production unit 115, the fractionation organic product stream 250 from the acetone-phenol fractionation unit section 230, the spent air knockout drum liquid stream 365 from the spent air knockout drum 330, the fuel gas knockout drum hydrocarbon liquid stream 370 from the fuel gas knockout drum 340. The mixed hydrocarbon waste stream 375 from the hydrocarbon buffer vessel 335 is sent to the thermal oxidation system 355.

The fuel gas knockout drum 340 contains at least one of the AMS hydrogen vent gas stream 295 from the AMS hydrogenation unit section 280, the hydrocarbon buffer vessel vent gas stream 391 from the hydrocarbon buffer vessel 335, the phenolic vent gas stream 393 from the phenolic water vessel 345, and the non-phenolic vent gas stream 395 from the non-phenolic water vessel 350. It may also contain the propane vent stream 130, and the benzene drag stream 135 from the cumene production unit 115. The burner fuel stream 380 from the fuel gas knockout drum 340 is sent to the thermal oxidation system 355.

The phenolic water vessel 345 contains at least one of: the fractionation waste water stream 255 from the acetone-phenol fractionation unit section 230, and the first phenolic waste water stream 271 from the phenol recovery unit section 260. It may also contain a skimmed water phase 382 from the hydrocarbon buffer vessel 335. The phenolic water stream 385 from the phenolic water vessel 345 is sent to the thermal oxidation system 355.

The non-phenolic water vessel 350 contains at least one of the peroxide-containing oxidation waste water stream 173 from the oxidation unit section 150, the peroxide-free oxidation waste water stream 322 from the peroxide destruction unit section 320, and the benzene column water stream 125 from the cumene production unit 115. The non-phenolic water stream 390 from the non-phenolic water vessel 350 is sent to the thermal oxidation system 355.

The temperature of one of the more of the spent air stream 360, the phenolic water stream 385, and the non-phenolic water stream 390 can be adjusted (e.g., increased or decreased) as needed. Heat for increasing the temperature can come from recovered waste heat from the thermal oxidation system 355, as will be discussed below.

The hydrocarbon buffer vessel 335, phenolic water vessel 345, and non-phenolic water vessel 350 each operate with a push/pull system using liquefied petroleum gas/waste gas/fuel gas to maintain a constant pressure. There is a vent gas stream 391, 393, 395 into and out of each of the hydrocarbon buffer vessel 335, phenolic water vessel 345, and non-phenolic water vessel 350. When the pressure is high, gas will be pushed out of the hydrocarbon buffer vessel 335, phenolic water vessel 345, and non-phenolic water vessel 350 to the fuel gas knockout drum 340 via line 397, while it will be pulled into the hydrocarbon buffer vessel 335, phenolic water vessel 345, and non-phenolic water vessel 350 when the pressure is low via the waste gas/fuel gas supply line 397.

Figure 4:
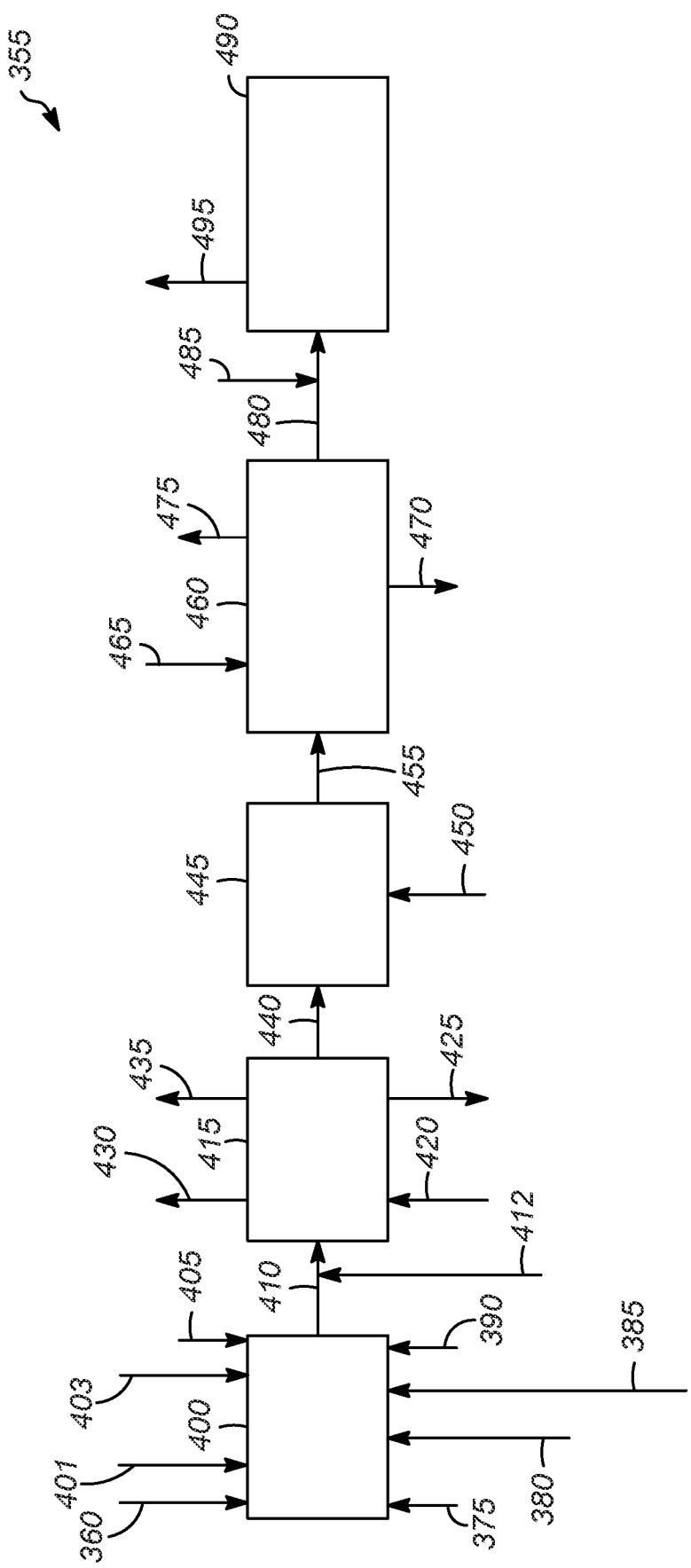
FIG. 4 is an illustration of one embodiment of a thermal oxidation system according to the present invention.

One embodiment of a thermal oxidation system 355 is illustrated in FIG. 4. The thermal oxidation system 355 comprises a thermal oxidizing section 400, a waste heat recovery section 415, a quench section 445, a SOx removal section 460, and an optional NOx removal section 490.

At least one of the spent air stream 360 from the spent air knockout drum 330, the mixed hydrocarbon waste stream 375 from the hydrocarbon buffer vessel 335, the burner fuel stream 380 from the fuel gas knockout drum 340, the phenolic water stream 385 from the phenolic water vessel 345, and the non-phenolic water stream 390 from the non-phenolic water vessel 350, along with make-up natural gas stream 401, quench stream 403, and combustion air stream 405 are introduced into the thermal oxidizing section 400. At least one of the spent air stream 360 from the spent air knockout drum 330, the phenolic water stream 385 from the phenolic water vessel 345, and the non-phenolic water stream 390 from the non-phenolic water vessel 350 may optionally be pre-heated and/or pressurized before being introduced into the thermal oxidizing section 400. The spent air stream 360 typically has a temperature of −30-30° C., and it might need to be raised to a temperature of 31-180° C. The phenolic water stream 385 and non-phenolic water stream 390 typically have a temperature of 1-70° C., and they might need to be raised to a temperature of 71-180° C.

The inlet temperature of the thermal oxidizing section 400 is typically in the range of −30-500° C. with a pressure of −1 kPa(g) to 3000 kPa(g). The outlet temperature is typically in the range of 650–1300° C. with a pressure of −1 kPa(g) to 50 kPa(g). The residence time in the thermal oxidizing section 400 is between 0.5 and 2 seconds. The thermal oxidizing section 400 operates at a temperature in the range of 650-1300° C. with a residence time between 0.5 and 2 seconds. Any suitable thermal oxidizing section 400 could be used, including, but not limited to, an adiabatic thermal oxidizer chamber. The thermal oxidizing section 400 can be forced draft, induced draft, or a combination of both. Although it is not typically present, there could be an optional selective non-catalytic reduction (SNCR) section. The inlet temperature of the SNCR section is typically in the range of 650-1300° C. with a pressure of −1 kPa(g) to 50 kPa(g). The outlet temperature is typically in the range of 650-1040° C. with a pressure of −1 kPa(g) to 50 kPa(g). The residence time in the SNCR section is between 0.2 and 1 seconds. The thermal oxidation step would be separated from the SNCR step via a choke wall in the vessel. The hydrocarbons are converted to $H_2O$ and $CO_2$. The sulfides from the sulfur species (e.g. $H_2S$) present in feed are converted to oxidized sulfur particulate SOx including, but not limited to, $SO_2$ and $SO_3$, and $H_2O$. The nitrogen from the nitrogen bound molecules (e.g. $NH_3$) present in the feed are converted to Nitrogen ($N_2$) and NOx, including, but not limited to, NO, $NO_2$. The HCl and $Cl_2$ (if either is present) remain. However, in many cases, there will not be significant amounts of nitrogen containing molecules, and/or sulfur containing molecules, and/or chlorine containing molecules in the feed to the thermal oxidizing section 400; therefore, the SNCR section, SOx removal section and NOx removal section will usually not be present.

In some embodiments. the phenolic water stream 385 from the phenolic water vessel 345 is directly injected into the flame section of the thermal oxidizing section 400, while the non-phenolic water stream 390 is injected downstream of the flame section. This reduces the amount of fuel needed to operate the thermal oxidizing section 400.

The flue gas stream 410 from the thermal oxidizing section 400 consists essentially of one or more of $H_2O$, $CO_2$, $N_2$, $O_2$, SOx (i.e., $SO_2$ and $SO_3$), NOx (i.e., NO and $NO_2$), HCl, $Na_2SO_4$, $Na_2CO_3$, $Cl_2$. "Consisting essentially of" means that one of more of the gases or vapors are present and there are no other gases or vapors present which require treatment before being released to the atmosphere. The flue gas stream 410 is sent to the waste heat recovery section 415. A quench stream 412 cools the flue gas stream 410 to a temperature below 720° C. and preferably be below 705° C. to avoid liquid salts fouling the boiler in the waste heat recover section 415. The inlet temperature of the waste heat recovery section 415 is typically in the range of 500-720° C. with a pressure of −2 kPa(g) to 50 kPa(g). The outlet temperature is typically in the range of 200-400° C. with a pressure of −2 kPa(g) to 50 kPa(g). Suitable waste heat recovery apparatus and methods include, but are not limited to, a waste heat recovery boiler, including, but not limited to, a firetube boiler or a watertube boiler. Boiler feed water or oil stream 420 enters the waste heat recovery section 415 where a portion is converted to steam or hot oil stream 430 as recovered waste heat, with the remainder exiting as blowdown water or oil stream 425. In some cases, the steam can be converted to electricity, for example using a steam turbine, if desired.

The recovered waste heat in steam or hot oil stream 430 can be in the form of low (e.g., less than 350 kPa(g)), medium (e.g., 350 kPa(g) to 1750 kPa(g)), or high pressure (e.g., greater than 1750 kPa(g)) saturated or superheated steam, hot oil, and/or electricity. The recovered heat can be used to provide heat to one or more pieces of equipment or process streams in the phenol/cumene complex or to other parts of the plant. For example, the recovered waste heat in steam or hot oil stream 430 can be used to heat to one or more of: a vaporizer in the CHP concentration unit section 175, a dehydrator steam heat exchanger in the decomposition unit section 195, and a reboiler in the acetone-phenol fractionation unit section 230, or for other heat requirements.

If $Na_2SO_4$, $Na_2CO_3$, SOx, NOx, HCl and $Cl_2$ removal are not required, exhaust stream 435, consisting essentially of one or more of $H_2O$, $CO_2$, $N_2$, $O_2$, $Na_2SO_4$, $Na_2CO_3$, SOx, NOx, HCl, and $Cl_2$ exits the waste heat recovery section 415.

Otherwise, the flue gas stream 440 from the waste heat recovery section 415 flows to the quench section 445 where the temperature of the flue gas is reduced to the saturation temperature using quench stream 450. The inlet temperature of the quench section 445 is typically in the range of 200-400° C. with a pressure of −3 kPa(g) to 50 kPa(g). The outlet temperature is typically in the range of 45–150° C. with a pressure of −3 kPa(g) to 50 kPa(g). Quench stream 450 includes, but is not limited to, air, de-SOx outlet flue gas, de-NOx outlet flue gas, water, or combinations thereof. The water may comprise a water stream (not shown) from the non-phenolic water vessel 350 or an outside water stream.

The quenched flue gas stream 455 from the quench section 445 is sent to the SOx removal section 460 for removal of at least one of Na2SO4, Na2CO3, SOx, HCl, and $Cl_2$. The inlet temperature of the SOx removal section 460 is typically in the range of 45-150° C. with a pressure of −4 kPa(g) to 50 kPa(g). The outlet temperature is typically in the range of 45-150° C. with a pressure of −4 kPa(g) to 50 kPa(g). For example, the SOx removal section may be a scrubbing section in which a stream 465 comprising caustic (aqueous NaOH) is introduced into the SOx removal section 460 where it reacts with the SOx, HCl, and $Cl_2$ in the flue gas if present. An aqueous stream 470 comprising at least one of $Na_2SO_3$, $NaHSO_3$, $Na_2SO_4$, and NaCl exits the SOx removal section 460. If desired, a reducing agent such as $NaHSO_4$ or $H_2O_2$, can be included to react with the $Cl_2$ to form HCl which reacts to form NaCl. Alternatively, stream 465 could be an $NH_3$ based solution (e.g., aqueous or anhydrous $NH_3$). The $NH_3$ reacts with the SOx to form $(NH_4)_2SO_4$. The $NH_3$ reacts with the $Cl_2$ to form $N_2$ and HCl, followed by the reaction of the HCl with the $NH_3$ forming $NH_4Cl$. A separate reducing agent is not needed when $NH_3$ is used. In this case, the aqueous stream 470 would be $H_2O$, $(NH_4)_2SO_4$ and $NH_4Cl$.

If NOx removal is not needed, exhaust stream 475, consisting essentially of one or more of $H_2O$, $CO_2$, $N_2$, $O_2$ and NOx, exits the SOx removal section 460.

The de-SOx outlet flue gas stream 480 from the SOx removal section 460 has a reduced level of $Na_2SO_4$, $Na_2CO_3$, HCl, $Cl_2$, SOx, and NOx compared to the incoming quenched flue gas stream 455. The de-SOx outlet flue gas stream 480 comprises one or more of $H_2O$, $CO_2$, $N_2$, $O_2$, and NOx.

If NOx above the allowable emission limit is present in the de-SOx outlet flue gas stream 480, the de-SOx outlet flue gas stream 480 is sent to the optional NOx removal section 490 to remove NOx. The inlet temperature of the NOx removal section 490 is typically in the range of 150-300° C. with a pressure of −5 kPa(g) to 50 kPa(g). The outlet temperature is typically in the range of 200-350° C. with a pressure of −5 kPa(g) to 50 kPa(g). The de-SOx outlet flue gas stream 480 may need to be heated to obtain the desired inlet temperature for the NOx removal section 490. For example, the NOx removal section 490 can be a selective catalytic reduction (SCR) section in which an ammonia and/or urea stream 485 is introduced into the SCR section where it reacts with the NOx and forms $N_2$ and $H_2O$. Any suitable SCR catalyst could be used, including but not limited to, ceramic carrier materials such as titanium oxide with active catalytic components such as oxides of base metals including vanadium, molybdenum, and tungsten, or an activated carbon based catalyst. The de-NOx outlet flue gas stream 495 comprises one or more of $H_2O$, $CO_2$, $N_2$, $O_2$.

Figure 5:
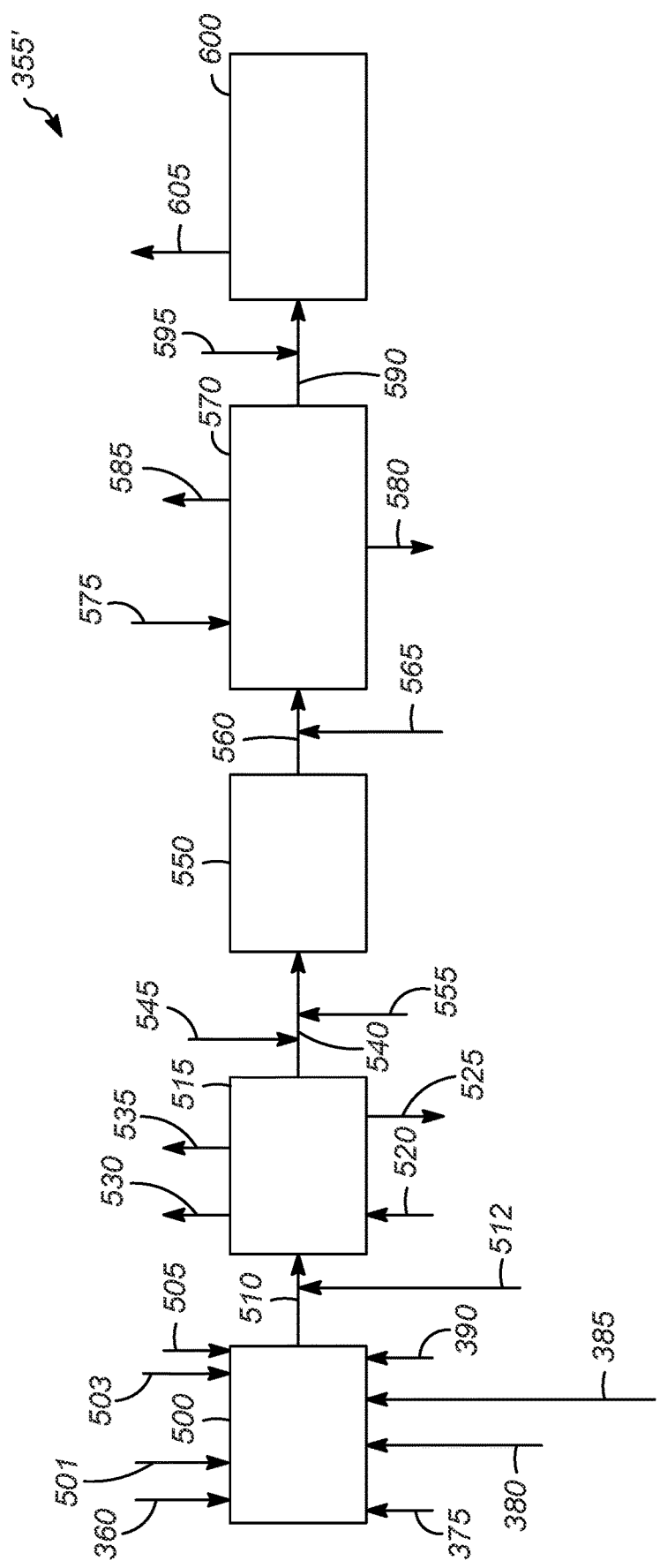
FIG. 5 is an illustration of another embodiment of a thermal oxidation system according to the present invention.

Another embodiment of the thermal oxidation system 355' is illustrated in FIG. 5. The thermal oxidation system 355' comprises a thermal oxidizing section 500, a waste heat recovery section 515, a SOx removal section comprising a SOx reaction section 550 and a filtration section 570, and an optional NOx removal section 600.

At least one of the spent air stream 360 from the spent air knockout drum 330, the mixed hydrocarbon waste stream 375 from the hydrocarbon buffer vessel 335, the burner fuel stream 380 from the fuel gas knockout drum 340, the phenolic water stream 385 from the phenolic water vessel 345, and the non-phenolic water stream 390 from the non-phenolic water vessel 350, along with make-up natural gas stream 501, quench stream 503, and combustion air stream 505 are introduced into the thermal oxidizing section 500, as described above.

At least one of the spent air stream 360 from the spent air knockout drum 330, the phenolic water stream 385 from the phenolic water vessel 345, and the non-phenolic water stream 390 from the non-phenolic water vessel 350 may optionally be pre-heated before being introduced into the thermal oxidizing section 500, as described above.

The inlet temperature of the thermal oxidizing section 500 is typically in the range of −30-500° C. with a pressure of −1 kPa(g) to 3000 kPa(g). The outlet temperature is typically in the range of 650-1300° C. with a pressure of −1 kPa(g) to 50 kPa(g). The residence time in the thermal oxidizing section 500 is between 0.5 and 2 seconds. Any suitable thermal oxidizing section 500 could be used, including, but not limited to, an adiabatic thermal oxidizer chamber or a non-adiabatic direct fired boiler. The thermal oxidizing section 500 can be forced draft, induced draft, or a combination of both. The inlet temperature of the optional SNCR section is typically in the range of 650-1300° C. with a pressure of −1 kPa(g) to 50 kPa(g). The outlet temperature is typically in the range of 650-1040° C. with a pressure of −1 kPa(g) to 50 kPa(g). The residence time in the SNCR section is between 0.2 and 1 seconds. The thermal oxidation step would be separated from the SNCR step via a choke wall in the vessel.

The flue gas stream 510 from the thermal oxidizing section 500 comprises one or more of $H_2O$, $CO_2$, $N_2$, $O_2$, SOx, $Na_2SO_4$, $Na_2CO_3$, NOx, HCl, and $Cl_2$. The flue gas stream 510 is sent to the waste heat recovery section 515. A quench stream 512 cools the flue gas stream 510 to a temperature below 720° C. and preferably be below 705° C. to avoid liquid salts fouling the boiler in the waste heat recover section 515. Boiler feed water or oil stream 520 enters the waste heat recovery section 515 where a portion is converted to steam or hot oil stream 530, with the remainder exiting as blowdown water or oil 525. Suitable waste heat recovery apparatus and methods are described above. The inlet temperature of the waste heat recovery section 515 is typically in the range of 500-720° C. with a pressure of −2 kPa(g) to 50 kPa(g). The outlet temperature is typically in the range of 200−400° C. with a pressure of −2 kPa(g) to 50 kPa(g). The recovered waste heat in steam or hot oil stream 530 can be in the form of low, medium, or high pressure saturated or superheated steam, hot oil, and/or electricity, as described above. The recovered waste heat in steam or hot oil stream 530 can be used one or more of: a vaporizer in the CHP concentration unit section 175, a dehydrator steam heat exchanger in the decomposition unit section 195, and a reboiler in the acetone-phenol fractionation unit section 230, or for other heat requirements.

If $Na_2SO_4$, $Na_2CO_3$, SOx, NOx, HCl, and $Cl_2$ removal are not required, exhaust stream 535, consisting essentially of one or more of $H_2O$, $CO_2$, $N_2$, $O_2$, $Na_2SO_4$, $Na_2CO_3$, SOx, NOx, HCl, and $Cl_2$ exits the waste heat recovery section 515.

The flue gas stream 540 from the waste heat recovery section 515 is sent to the SOx reaction section 550 to convert at least one of SOx, HCl, and $Cl_2$. The inlet temperature of the SOx reaction section 550 is typically in the range of 200−400° C. with a pressure of −3 kPa(g) to 50 kPa(g). The outlet temperature is typically in the range of 200−400° C. with a pressure of −3 kPa(g) to 50 kPa(g). Fresh sorbent 545 and optionally recycled sorbent 555 (comprising a mixture of one or more NaCl, $Na_2CO_3$, $Na_2SO_4$, $NaNO_3$, $CaCl_2$, $CaSO_4$, $CaCO_3$, $Ca(NO_3)_2$, $MgCl_2$, $MgCO_3$, $MgSO_4$, and $Mg(NO_3)_2$, depending on the compounds used in the reactant used, as discussed below) can be added to the flue gas stream 540. For example, the SOx reaction section 550 may contain a reactant, such as $NaHCO_3$, $NaHCO_3 \cdot Na_2CO_3 \cdot 2(H_2O)$, $CaCO_3$, $Ca(OH)_2$, and $Mg(OH)_2$, which reacts with the SOx, NOx, HCl, and $Cl_2$ to form NaCl, $Na_2CO_3$, $Na_2SO_4$, $NaNO_3$, $CaCl_2$, $CaSO_4$, $CaCO_3$, $Ca(NO_3)_2$, $MgCl_2$, $MgCO_3$, $MgSO_4$, $Mg(NO_3)_2$, and NOx. The de-SOx outlet flue gas stream 560 has a less $Na_2SO_4$, $Na_2CO_3$, HCl, $Cl_2$, SOx, and NOx compared to the incoming flue gas stream 540. The de-SOx outlet flue gas stream 560 comprises one or more of $H_2O$, $CO_2$, $N_2$, $O_2$, NaCl, $Na_2CO_3$, $Na_2SO_4$, $NaNO_3$, $CaCl_2$, $CaSO_4$, $CaCO_3$, $Ca(NO_3)_2$, $MgCl_2$, $MgCO_3$, $MgSO_4$, $Mg(NO_3)_2$, NOx, and $Cl_2$.

The de-SOx outlet flue gas stream 560 is combined with a quench stream 565 comprising air, and/or water, and/or quenched flue gas. The temperature of the de-SOx outlet flue gas stream 560 is typically reduced from 200-400° C. with a pressure of −3 kPa(g) to 50 kPa(g) to 150-250° C. with a pressure of −4 kPa(g) to 50 kPa(g). The quenched de-SOx outlet flue gas stream 560 is sent to the filtration section 570. The inlet temperature of the filtration section 570 is typically in the range of 150-350° C. with a pressure of −5 kPa(g) to 50 kPa(g). The outlet temperature is typically in the range of 150−350° C. with a pressure of −5 kPa(g) to 50 kPa(g). Suitable filtration sections 570 may include, but are not limited to, a bag filter, a ceramic filter, an electrostatic precipitator, or combinations thereof. An instrument air purge or high voltage DC 575 is introduced into the filtration section 570. In the case of the instrument air purge, it purges the retained material from the filter. In the case of the high voltage stream, it charges the cathodes of the ESP. The particulate is removed from the ESP by vibration. Dry residue stream 580 comprising at least one of NaCl, $Na_2CO_3$, $Na_2SO_4$, $NaNO_3$, $CaCl_2$, $CaSO_4$, $CaCO_3$, $Ca(NO_3)_2$, $MgCl_2$, $MgCO_3$, $MgSO_4$, and $Mg(NO_3)_2$ exits the filtration section 570. The filtered flue gas stream 590 comprises one or more of $H_2O$, $CO_2$, $N_2$, $O_2$, and NOx.

If NOx removal is not required, exhaust stream 585, consisting essentially of one or more of $H_2O$, $CO_2$, $N_2$, NOx, and $O_2$ exits the filtration section 570.

If NOx is present in the filtered flue gas stream 590, the filtered flue gas stream 590 is sent to the optional NOx removal section 600 to remove NOx as discussed above. The inlet temperature of the NOx removal section 600 is typically in the range of 150-300° C. with a pressure of −6 kPa(g) to 50 kPa(g). The outlet temperature is typically in the range of 200-350° C. with a pressure of −6 kPa(g) to 50 kPa(g). For example, the NOx removal section 600 can be a selective catalytic reduction (SCR) section in which an ammonia and/or urea stream 595 is introduced into the SCR section where it reacts with the NOx and forms $N_2$ and $H_2O$. Any suitable SCR catalyst could be used, including but not limited to, ceramic carrier materials such as titanium oxide with active catalytic components such as oxides of base metals including vanadium, molybdenum, and tungsten, or an activated carbon based catalyst. The de-NOx outlet flue gas stream 605 comprises one or more of $H_2O$, $CO_2$, $N_2$, and $O_2$.

Figure 6:
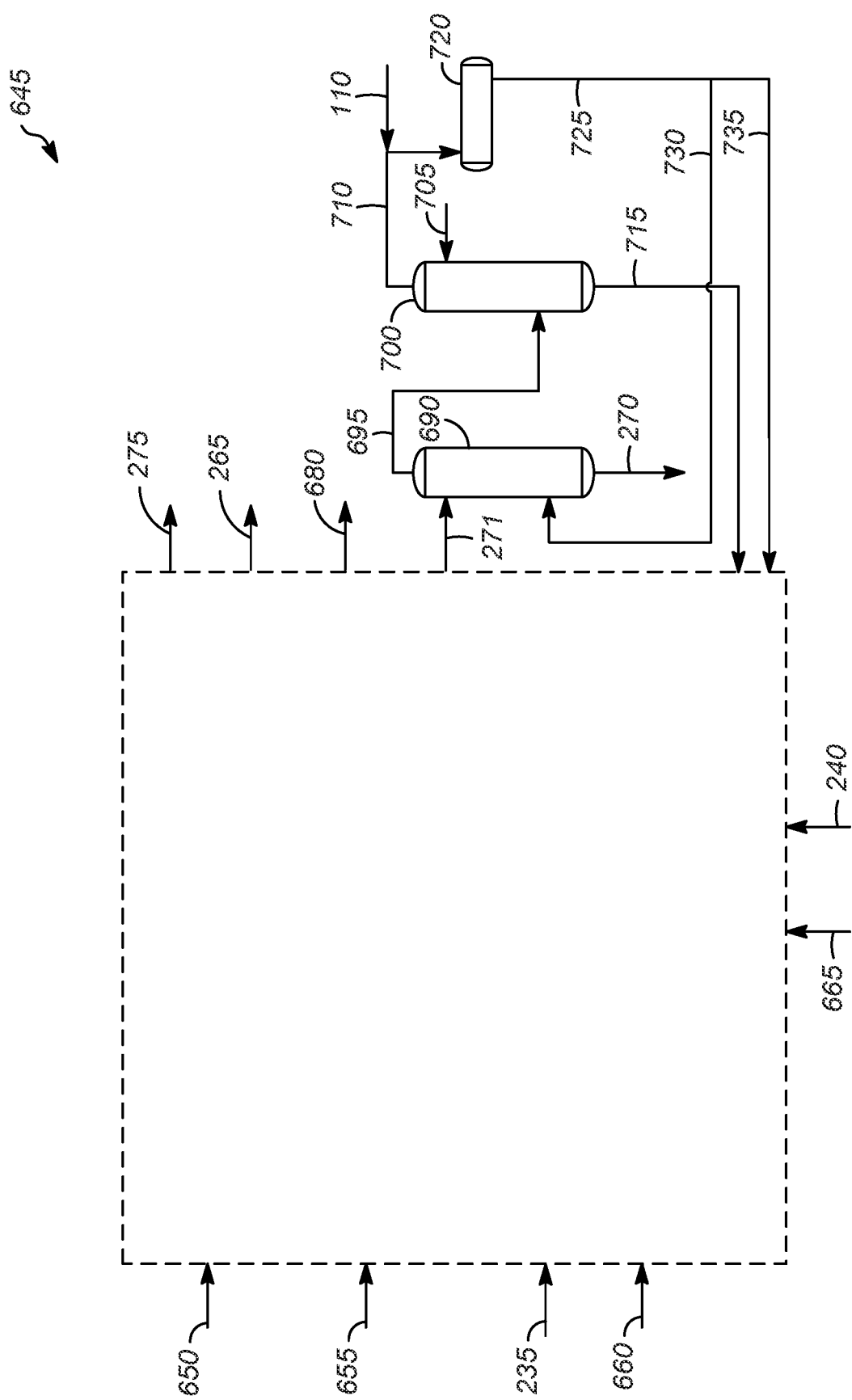
FIG. 6 is an illustration of a portion of a conventional phenol recovery section.

FIG. 6 illustrates a portion 645 of the phenol recovery unit section 260 for a conventional complex. The fractionation cumene-AMS-phenol stream 235 and the fractionation phenolic water stream 240 are sent to the phenol recovery unit section 260, along with water stream 650, make-up caustic stream 655, fresh cumene stream 660, and an acid injection stream 665. The cumene-AMS feed stream 275 is sent to the AMS hydrogenation unit section 280. Recycled sprung phenol stream 265 is sent to the neutralization unit section 215. A water wash waste stream 680 exits the portion 645 of the phenol recovery unit section 260. A first phenolic waste water stream 271 is sent to an oil extraction column 690 where it is separated into a phenolic rich cumene solvent stream 695 comprising cumene and phenol (e.g., 50-1000 wppm phenol, balance cumene) and final phenolic waste water stream 270. The phenolic rich cumene solvent stream 695 is sent to solvent caustic wash column 700. Makeup caustic stream 705 is introduced into solvent caustic wash column 700 to remove phenol from the phenolic rich cumene solvent stream 695. Recycle sodium phenate stream 715 is returned to the portion 645 of phenol recovery unit section 260. The phenol portion of this stream exits with the recycled sprung phenol stream 265. Lean solvent stream 710 comprising cumene (e.g., 0-50 wppm phenol) and fresh cumene feed 120 are sent to the solvent drum 720. Cumene recycle stream 725 is divided into oil extraction column cumene recycle stream 730 and PRU cumene recycle stream 735. Oil extraction column cumene recycle stream 730 is returned to the oil extraction column 690. PRU cumene recycle stream 735 is returned to the portion 645 of the phenol recovery unit section 260.

Figure 7:
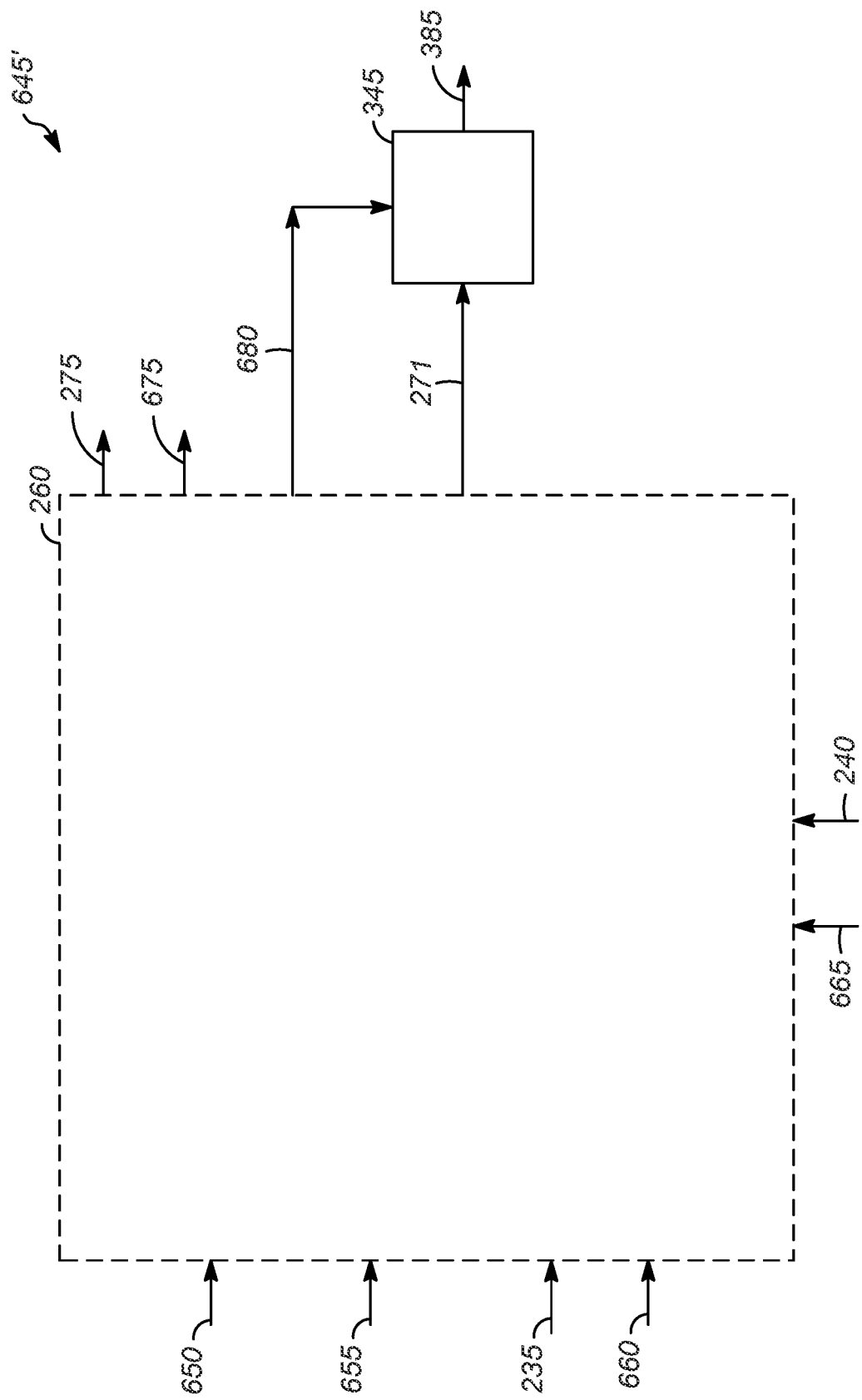
FIG. 7 is an illustration of a portion of a phenol recovery unit section according to the present invention.

FIG. 7 illustrates the portion 645' of the phenol recovery unit section 260 according to an embodiment of the present invention. In this arrangement, the oil extraction column 690 and solvent caustic wash column 700 have been eliminated, significantly reducing equipment cost. The water wash waste stream 680 and first phenolic waste water stream 271 are sent to the phenolic water vessel 345. The phenolic water stream 385 from the phenolic water vessel 345 is sent to the thermal oxidation system 355. This arrangement reduces the amount of caustic (NaOH) and $H_2SO_4$ because the phenolic water is sent to the thermal oxidation system 355.

Figure 8:
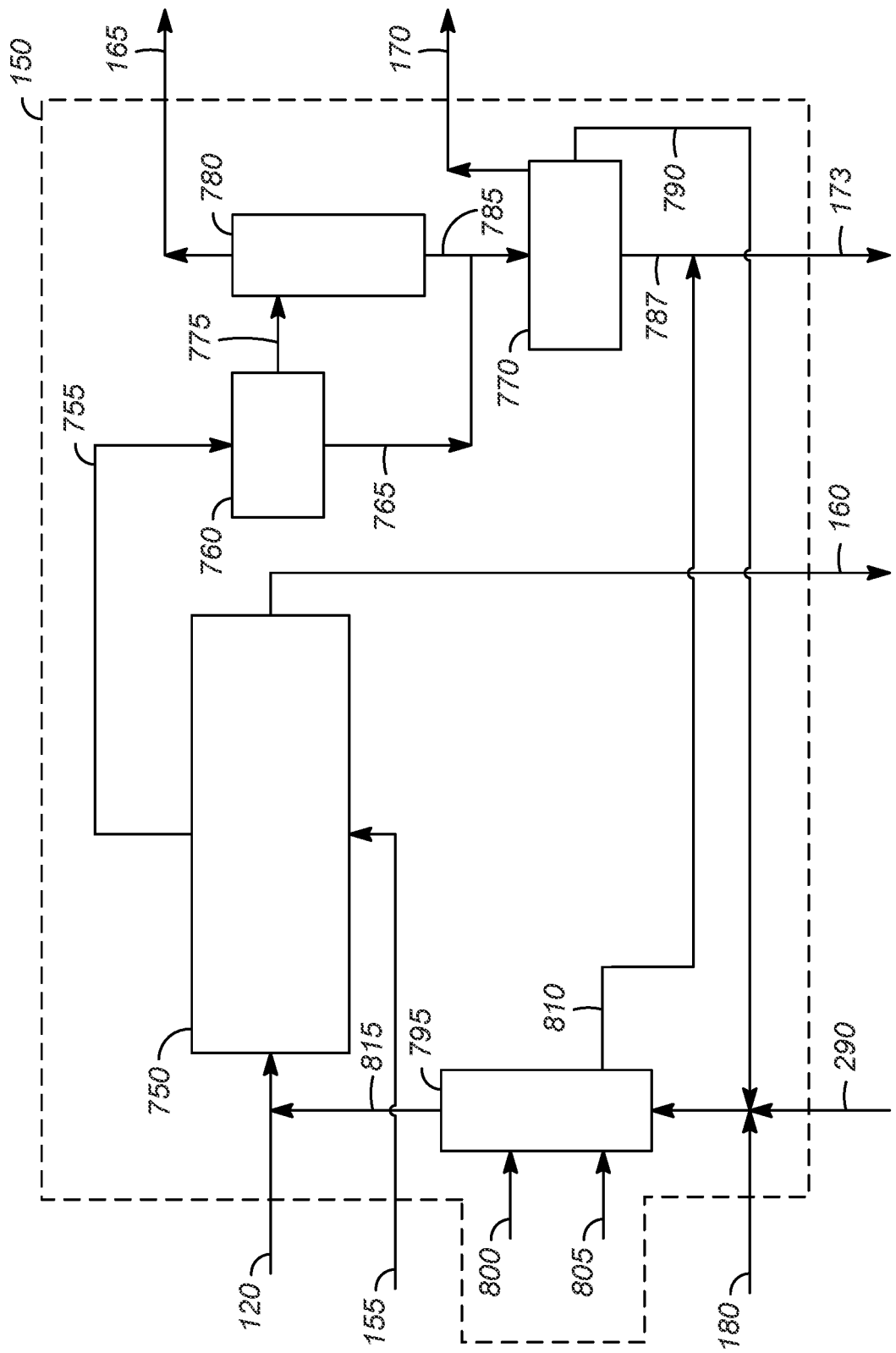
FIG. 8 is an illustration of one embodiment of a conventional oxidation section.

FIG. 8 illustrates one embodiment of a conventional oxidation unit section 150. The cumene stream 120 and the oxidation gas stream 155 are sent to an oxidation reactor 750 where the cumene is oxidized to CHP. The oxidation product stream 160 is sent to the CHP concentration unit section 175, as described above.

The oxidation spent air stream 755 is cooled in an oxidizer vent gas cooler 760 where it is separated into a cooled vent gas stream 775 and an oxidizer vent gas cooler condensate stream 765. The cooled vent gas stream 775 is sent to a vent gas treatment unit 780 for treatment. The oxidation spent air stream 165 from the vent gas treatment unit 780 is sent to the thermal oxidizer 305. The oxidizer vent gas cooler condensate stream 765 from the oxidizer vent gas cooler 760 and a vent gas treatment unit condensate stream 785 from the vent gas treatment unit 780 are sent to decanter vessel 770. Decanter vent stream 170 is sent to the thermal oxidizer 305. Decanter water effluent stream 787 exits the decanter vessel 770. The decanter cumene recycle stream 790 is sent to a cumene feed wash column 795. The concentration section recycle cumene stream 180 from the CHP concentration unit section 175 and the MSHP recycled cumene stream 290 from the AMS hydrogenation unit section 280 may also be sent to the cumene feed wash column 795. A recycle cumene wash water stream 800 and a recycle cumene wash caustic stream 805 are introduced into the cumene feed wash column 795. The washed cumene stream 815 is sent to the oxidation reactor 750. A recycle cumene wash water waste stream 810 exits the cumene feed wash column 795, is combined with the decanter water effluent stream 787 to form peroxide-containing oxidation waste water stream 173. Peroxide-containing oxidation waste water stream 173 can be sent directly to the waste water treatment plant 315, or optionally to the peroxide destruction unit section 320 to form peroxide-free oxidation waste water stream 322 before being sent to the waste water treatment plant 315.

Figure 9:
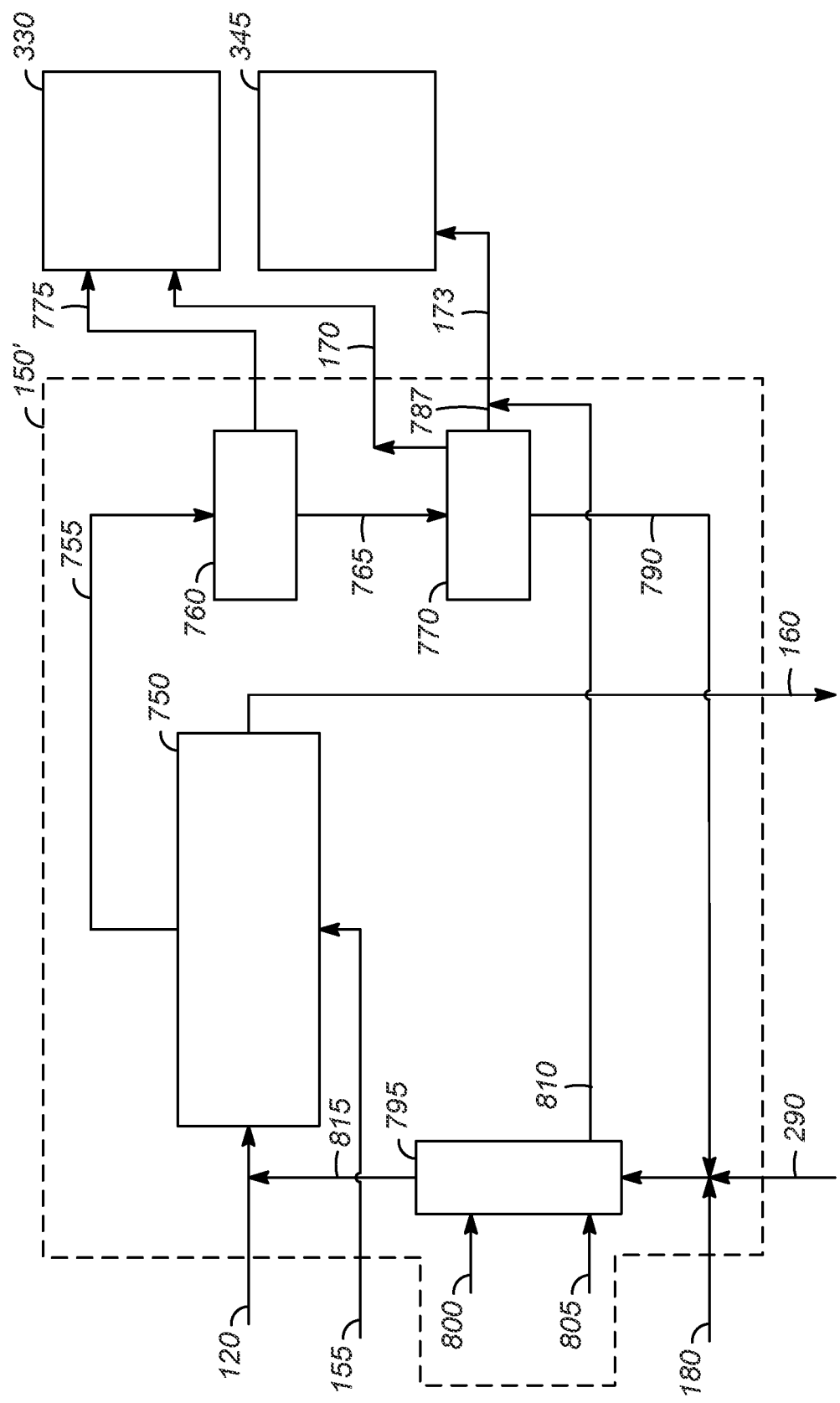
FIG. 9 is an illustration of the embodiment of the oxidation unit section of FIG. 8 according to the present invention.

FIG. 9 illustrates a similar oxidation reaction unit section 150' according to the present invention. In this embodiment, the vent gas treatment unit 780 is eliminated. The oxidizer vent gas cooler condensate stream 765 from the oxidizer vent gas cooler 760 is sent to decanter vessel 770. The cooled vent gas stream 775 from the oxidizer vent gas cooler 760 is sent to the spent air knockout drum 330. Decanter vent stream 170 from the decanter vessel 770 is sent the spent air knockout drum 330. Decanter water effluent stream 787 is combined with the recycle cumene wash water waste stream 810 from the cumene feed wash column 795 to form peroxide-containing oxidation waste water stream 173. Peroxide-containing oxidation waste water stream 173 can be sent directly to the phenolic water vessel 345 or optionally to the peroxide destruction unit section 320 to form peroxide-free oxidation waste water stream 322 before being sent to the phenolic water vessel 345.

Figure 10:
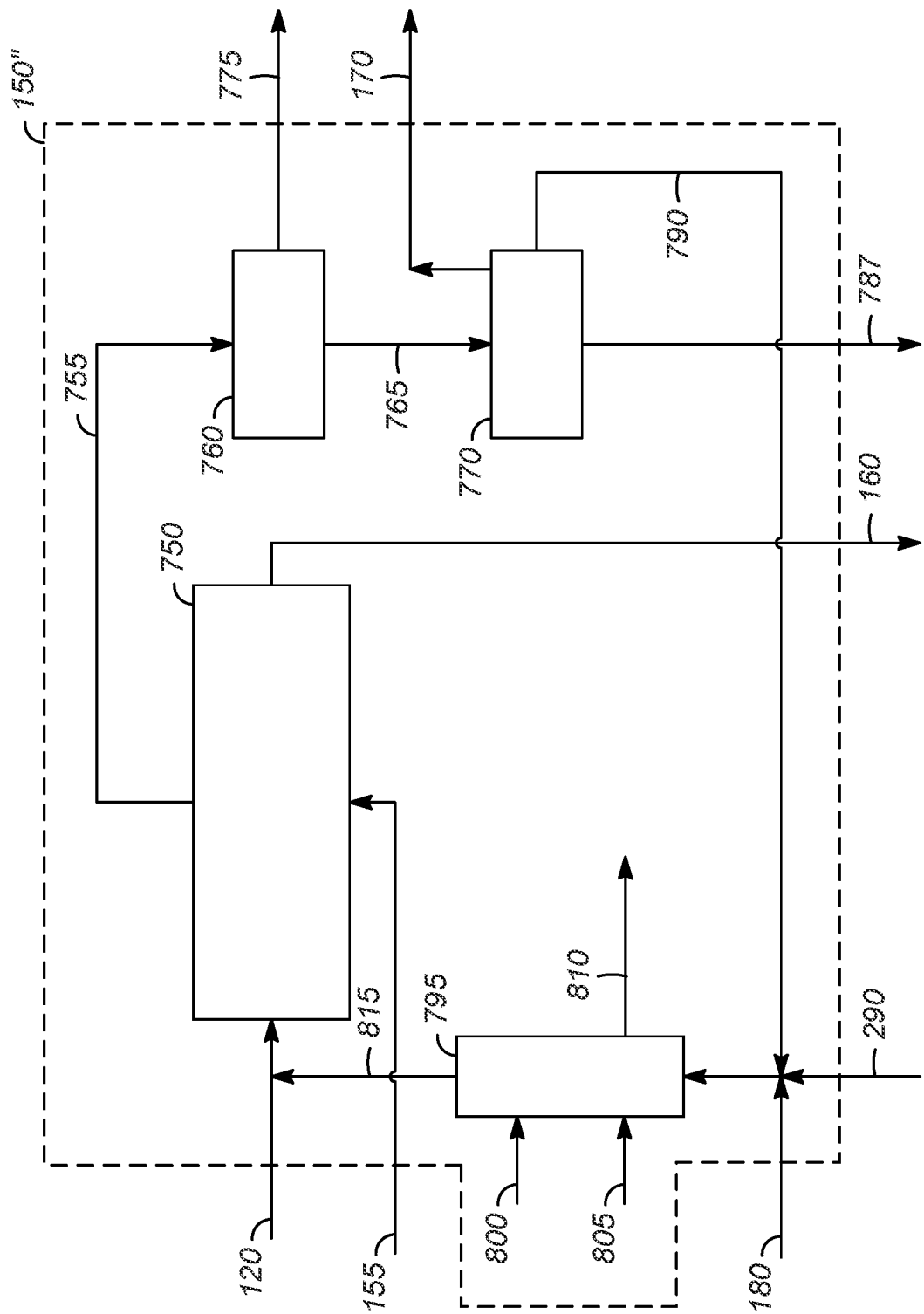
FIG. 10 is an illustration of another embodiment of a conventional oxidation section.

FIG. 10 illustrates another embodiment of a conventional oxidation unit section 150". In this case, there is no vent gas treatment unit 780. In this embodiment, the oxidation spent air stream 755 is cooled in an oxidizer vent gas cooler 760 where it is separated into a cooled vent gas stream 775 and an oxidizer vent gas cooler condensate stream 765. The cooled vent gas stream 775 is sent to the thermal oxidizer 305. The oxidizer vent gas cooler condensate stream 765 from the oxidizer vent gas cooler 760 is sent to decanter vessel 770. Decanter vent stream 170 is sent to the thermal oxidizer 305. Decanter water effluent stream 787 is sent to the waste water treatment plant 315. The decanter cumene recycle stream 790 is sent to a cumene feed wash column 795. The remainder of the process is as described for FIG. 8.

Figure 11:
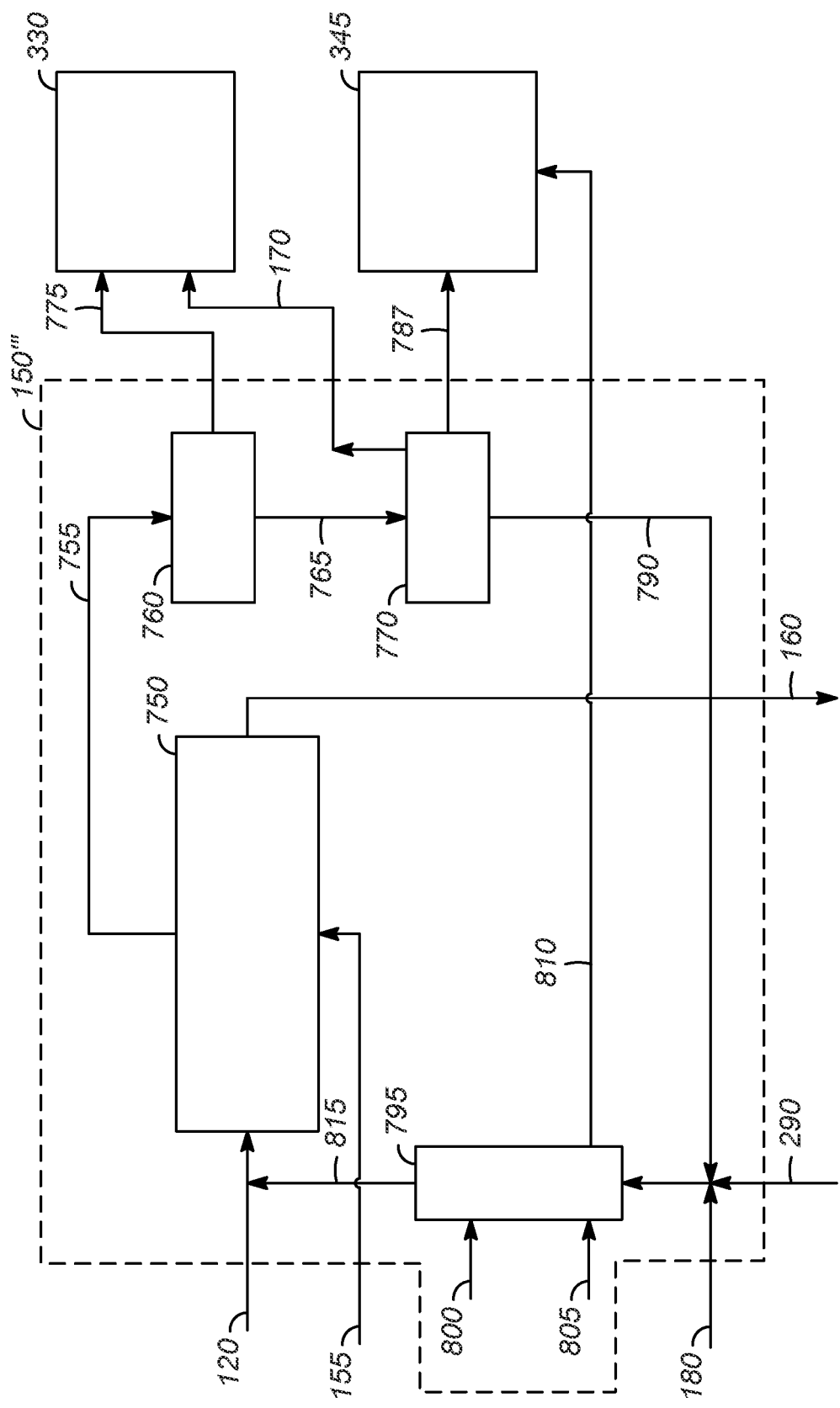
FIG. 11 is an illustration of the embodiment of the oxidation unit section of FIG. 10 according to the present invention.

FIG. 11 illustrates a similar oxidation reaction unit section 150''' according to the present invention. In this embodiment, the cooled vent gas stream 775 from the oxidizer vent gas cooler 760 is sent to the spent air knockout drum 330. Decanter vent stream 170 from the decanter vessel 770 is sent the spent air knockout drum 330. Decanter water effluent stream 787 is sent to the phenolic water vessel 345. The recycle cumene wash water waste stream 810 from the cumene feed wash column 795 is sent to the phenolic water vessel 345.

Figure 12:
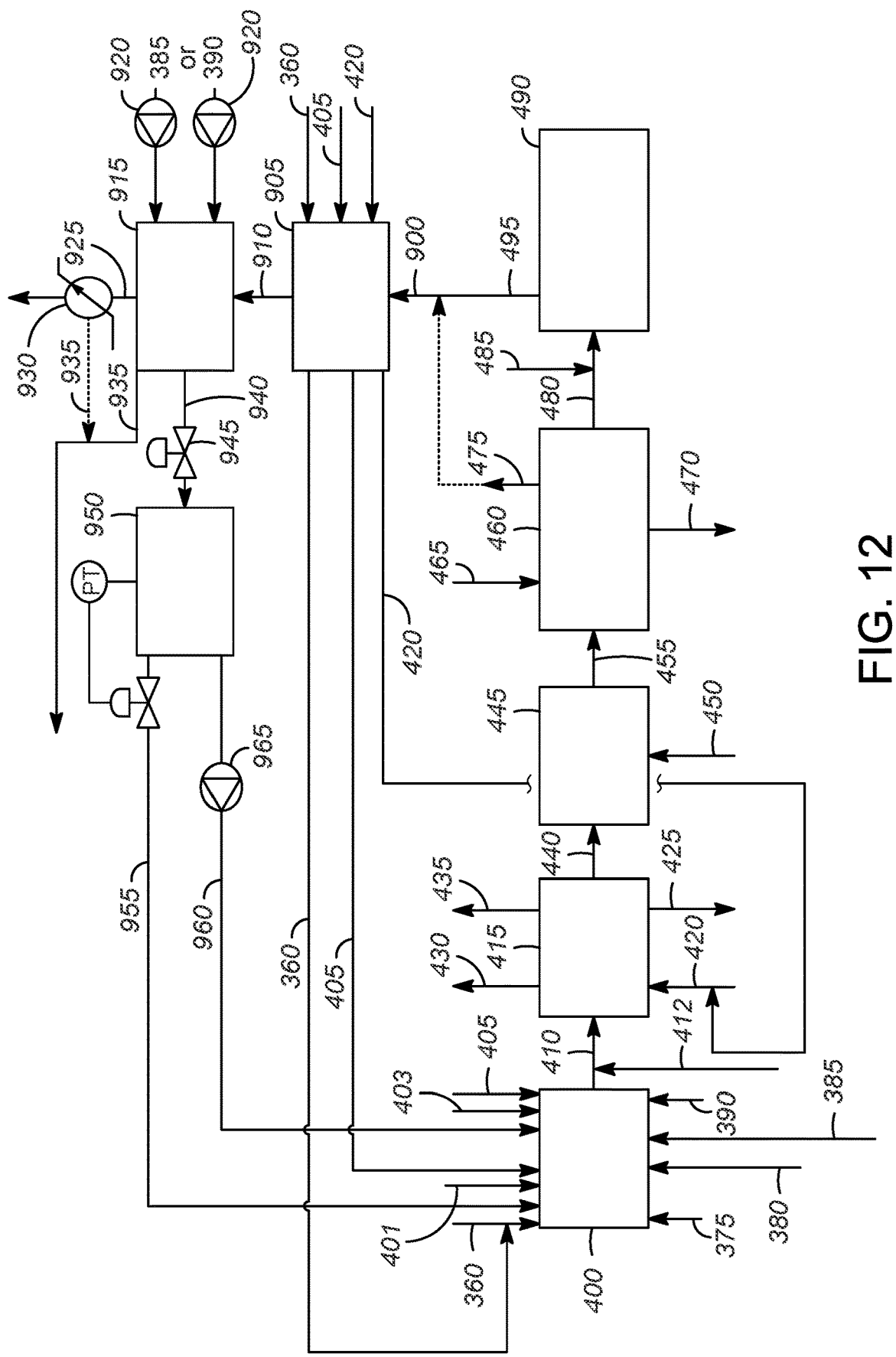
FIG. 12 is an illustration of one embodiment of the thermal oxidation system of FIG. 4 with improved energy recovery.

FIG. 12 illustrates an embodiment of the thermal oxidation system 355 of FIG. 4 with improved energy recovery. In this embodiment, energy can be recovered from the exhaust vapor stream 900 by cooling the vapor and condensing the water in the exhaust vapor stream 900. The condensate stream can be used as process water for other parts of the process, in some cases after treatment like neutralization and/or deaeration and/or filtration.

The exhaust vapor stream 900 may be sent to an optional secondary heat exchanger 905. The exhaust vapor stream 900 can be the de-NOx outlet flue gas stream 495 or exhaust stream 475. The exhaust vapor stream 900 is sent to the second side of the secondary heat exchanger 905.

A process stream is sent to the first side of the secondary heat exchanger 905. There can be one or more secondary heat exchangers 905, depending on temperature of the exhaust vapor stream 900 and the number of process streams that are to be heated.

Figure 13:
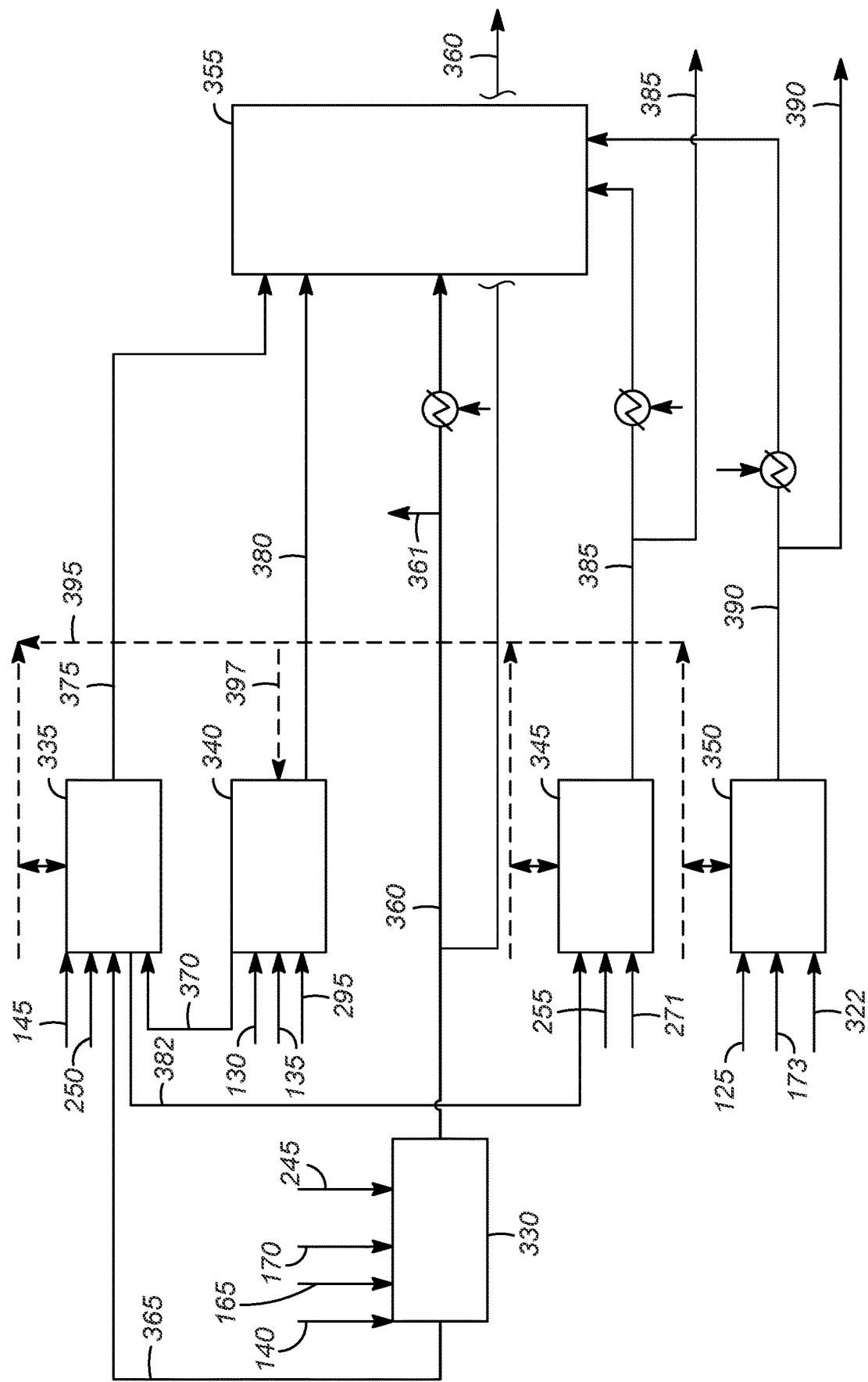
FIG. 13 is an illustration of the source of the process waste water streams used in the energy recovery system.

The process stream can be all or a portion of the spent air stream 360 from the spent air knockout drum 330, as shown in FIG. 13. Other options for the process stream include all or a portion of the combustion air stream 405, and all or a portion of the boiler feed water or oil stream 420.

The process stream is heated by the heat exchange with the exhaust vapor stream 900 which is cooled as a result to form a first cooled exhaust vapor stream 910.

The heated spent air stream 360 is sent to the thermal oxidizing section 400 of the thermal oxidation system 355. Heated combustion air stream 405 would also be sent to the thermal oxidizing section 400, while heated boiler feed water or oil stream 420 would be sent to the waste heat recovery section 415 thereby increasing the steam generation or hot oil generation efficiency.

A process waste water stream is passed through the first side of the primary heat exchanger 915. There can be one or more primary heat exchangers 915 depending on the temperature of the exhaust vapor stream 900 or first cooled exhaust vapor stream 910 and the number of process waste water streams that are to be heated.

The process waste water stream can be compressed in a pump and/or compressor 920 from a pressure of about 0-75 psig to a pressure of about 100-400 psig, for example, before it is introduced into the primary heat exchanger 915 to avoid flashing and/or boiling in the primary heat exchanger 915.

The process waste water stream can be all or a portion of at least one of the phenolic water stream 385 from the phenolic water vessel 345 and the non-phenolic water stream 390 from the non-phenolic water vessel 350.

The first cooled exhaust vapor stream 910 is sent to the primary heat exchanger 915 where it is passed through the second side of the primary heat exchanger 915. Alternatively, in the absence of the secondary heat exchanger 905, exhaust vapor stream 900 is sent to the primary heat exchanger 915.

The first cooled exhaust vapor stream 910 entering the primary heat exchanger 915 has a temperature above the dew point. The heat exchange with the process waste water stream lowers the temperature of the first cooled exhaust vapor stream 910. In some cases, the temperature will be lowered to a temperature at or below the dew point which results in condensation of the water out of the first cooled exhaust vapor stream 910. The resulting second cooled exhaust vapor stream 925 can be sent to an exhaust stack and released to the atmosphere.

In other cases, the temperature will not be lowered sufficiently to condense water (any, most, or all) from the first cooled exhaust vapor stream 910. In this case, an optional third exchanger 930 can be used to lower the temperature of the second cooled exhaust vapor stream 925 to a temperature at or below the dew point leading to the formation of water condensate. The cooling medium for the third heat exchanger can be cold/ambient air or cold water, for example.

Figure 14:
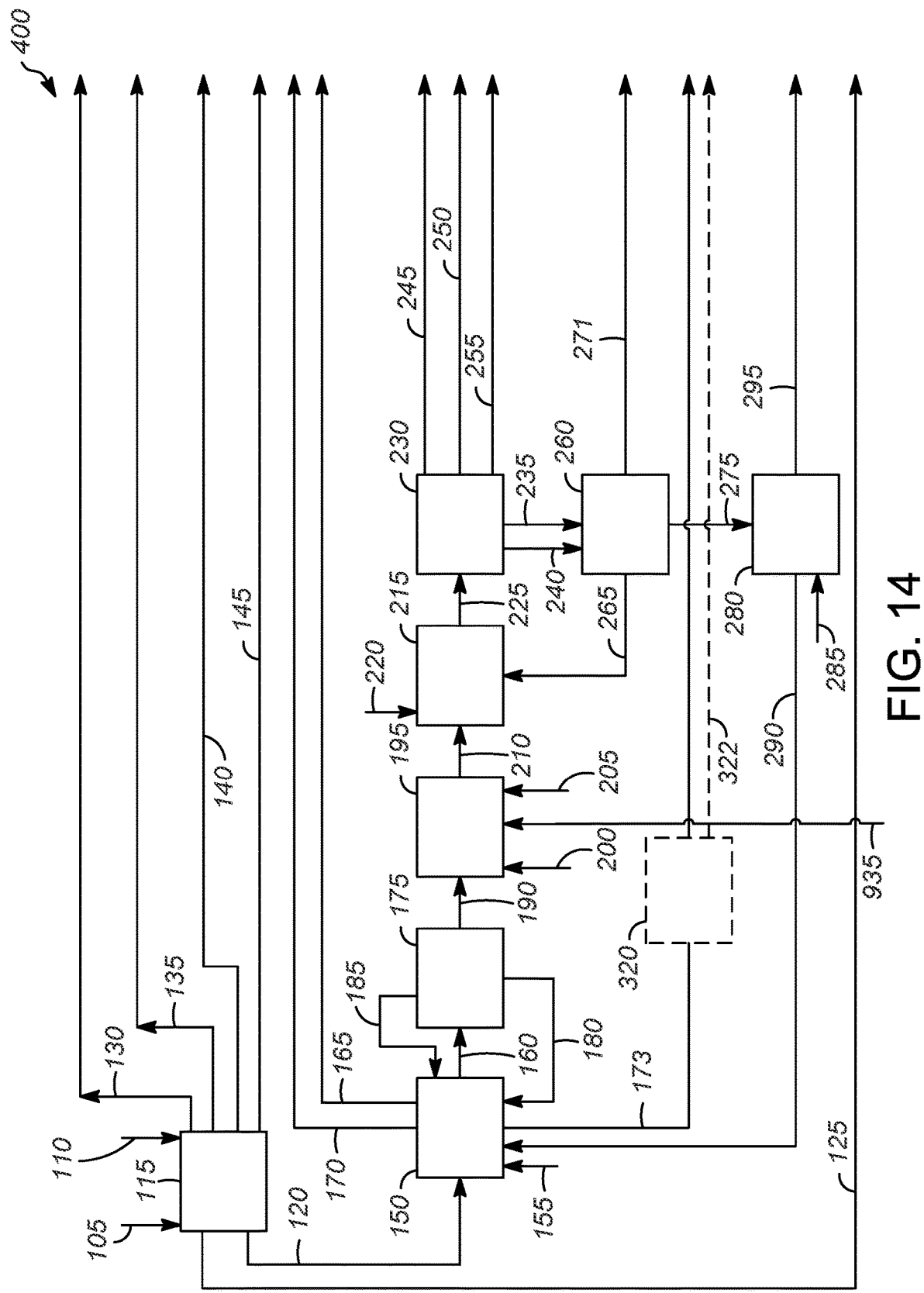
FIG. 14 is an illustration of the use of the condensate stream formed in the energy recovery system.
Figure 15:
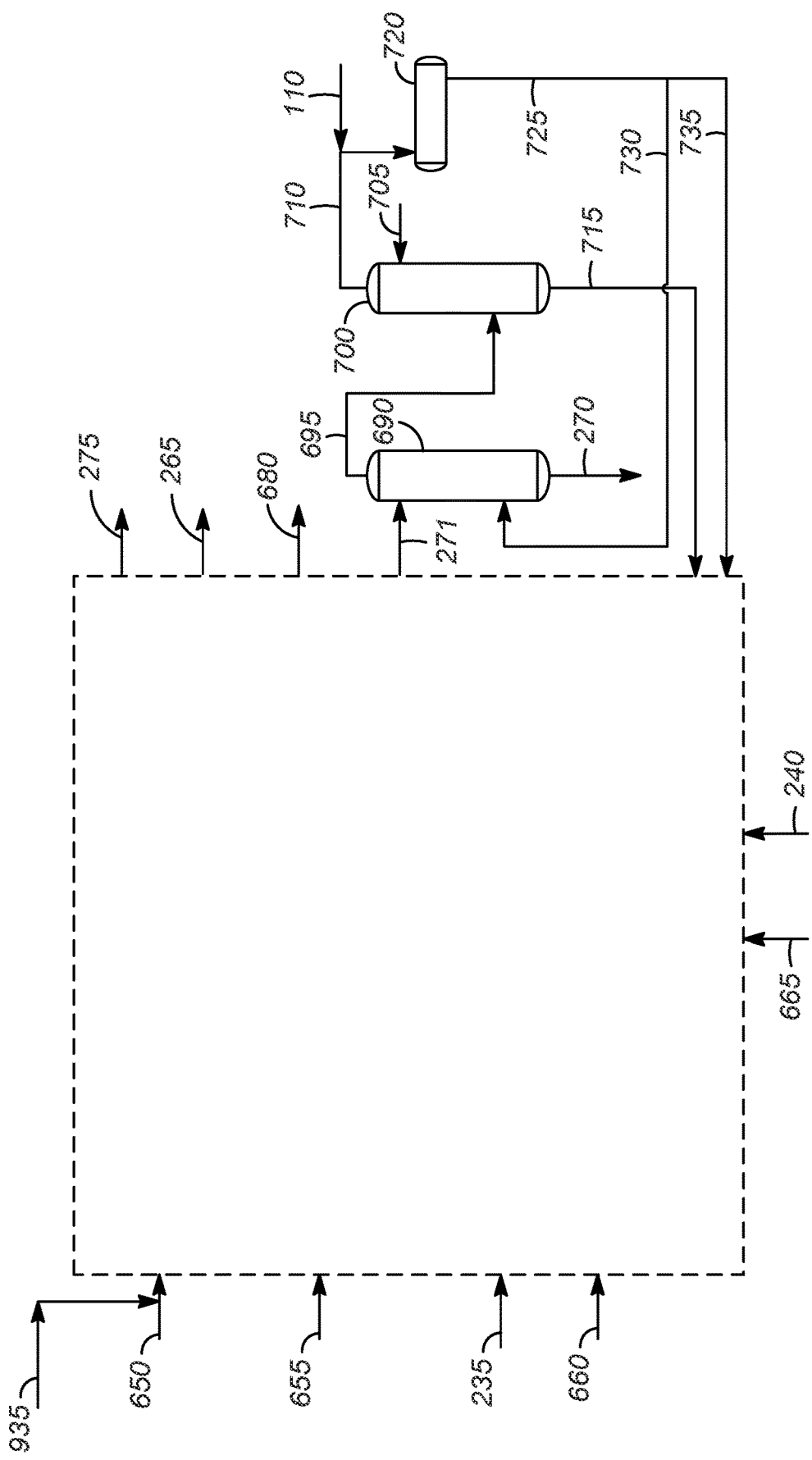
FIG. 15 is another illustration of the use of the condensate stream formed in the energy recovery system.

The water condensate is recovered and exits the primary heat exchanger 915 and/or the third heat exchanger as condensate stream 935. Condensate stream 935 can be sent to decomposition unit section 195 as shown in FIG. 14, and/or the phenol recovery unit section 260 as shown in FIG. 15, and/or used as quench stream 450 as shown in FIG. 12, in some cases after treatment like neutralization and/or deaeration and/or filtration The heated process waste water stream 940 from the primary heat exchanger 915 is sent through throttling or let down valve 945 to flash tank 950, which is at lower pressure (e.g., at a pressure of about 1-20 psig) than the primary heat exchanger 915. When the higher pressure heated process waste water stream 940 enters the lower pressure flash tank 950, it is flashed into a vapor stream 955 and a liquid stream 960. The vapor stream 955 and liquid stream 960 are sent to the thermal oxidizing section 400 of the thermal oxidation system 355. There can be an optional pump and/or compressor 965 on the line for the liquid stream 960.

Figure 16:
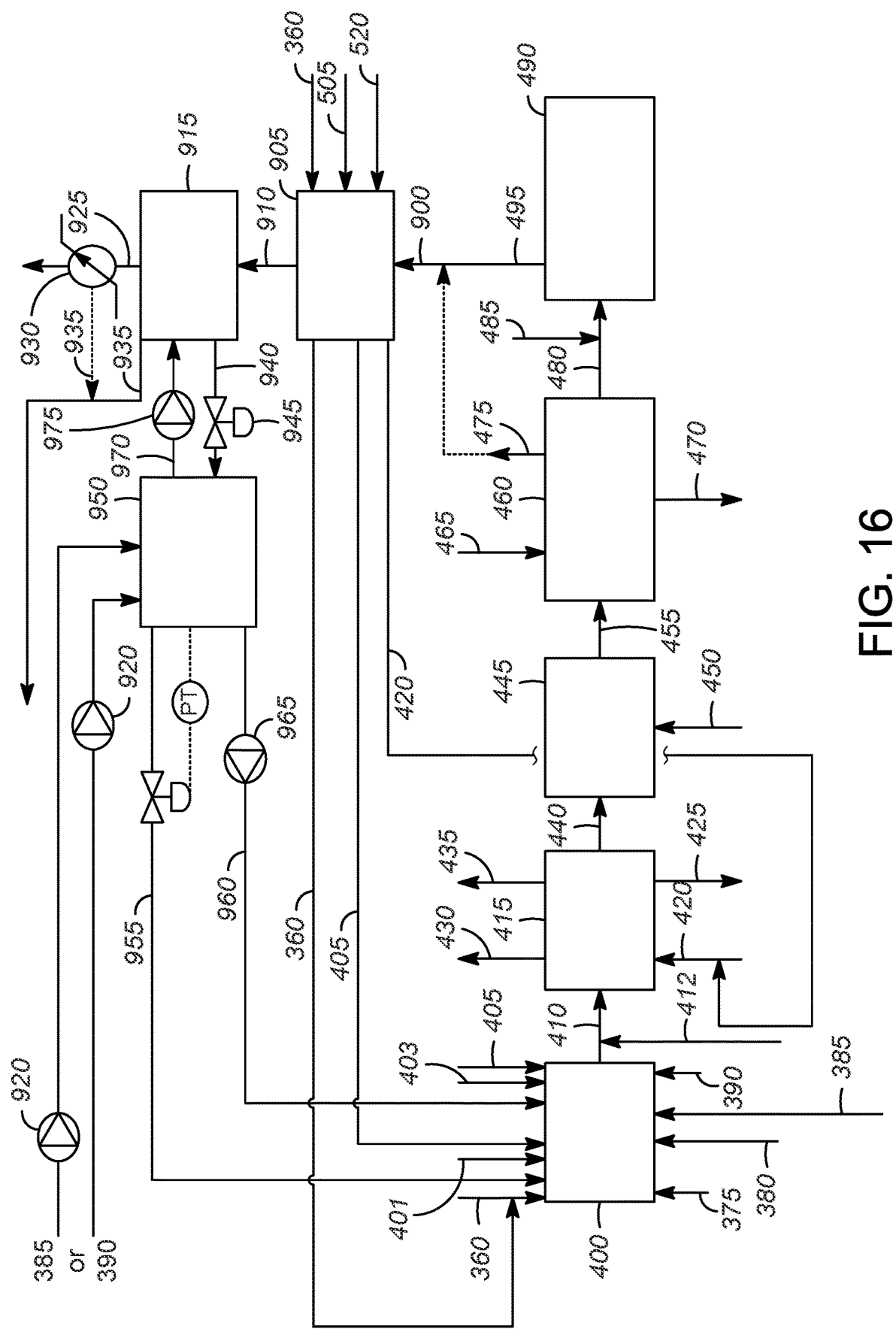
FIG. 16 is an illustration of another embodiment of the thermal oxidation system of FIG. 4 with improved energy recovery.

FIG. 16 illustrates an alternate energy recovery system for the thermal oxidation system 355 of FIG. 4. In this arrangement, the process waste water stream (with optional compression in a pump and/or compressor 920) is sent to the flash tank 950 for an initial flash separation. A portion 970 of the liquid from the flash tank 950 may be compressed in optional pump and/or compressor 975 and sent to the first side of the primary heat exchanger 915. The heated process waste water stream 940 is passed through throttling or let down valve 945 to reduce the pressure and returned to the flash tank 950 where further separation takes place.

Water is recycled from the flash tank to the primary heat exchanger and back. The ratio of the process waste water feed to the flash vessel to the recycle rate (i.e., the flow rate from the flash tank to the primary heat exchanger and back) is about 1:2 to 1:10.

This process is designed to minimize the time the process waste water stream spends in the primary heat exchanger 915 to avoid the formation of steam in the primary heat exchanger 915.

Figure 17:
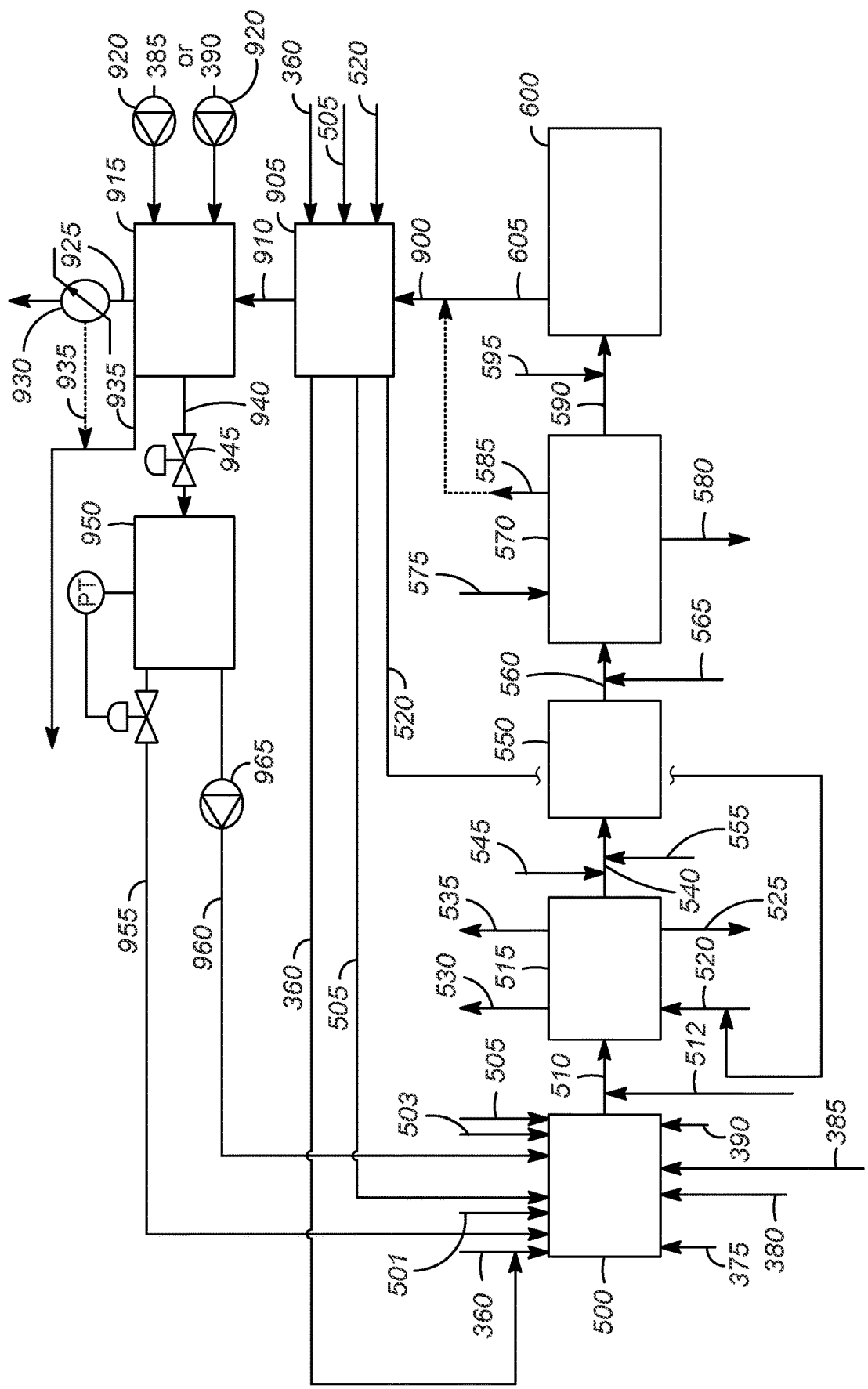
FIG. 17 is an illustration of one embodiment of the thermal oxidation system of FIG. 5 with improved energy recovery.

FIG. 17 shows a similar energy recovery system for the thermal oxidizing system of FIG. 5. In this embodiment, the exhaust vapor stream 900 can be the de-NOx outlet flue gas stream 605 or exhaust stream 585.

The exhaust vapor stream 900 may be sent to the second side of the optional secondary heat exchanger 905. A process stream is sent to the first side of the secondary heat exchanger 905. There can be one or more secondary heat exchangers 905, depending on temperature of the exhaust vapor stream and the number of process streams that are to be heated.

The process stream can be all or a portion of the spent air stream 360 from the spent air knockout drum 330, as shown in FIG. 13. Other options for the process stream include all or a portion of the combustion air stream 505, and all or a portion of the boiler feed water or oil stream 520.

The process stream is heated by the heat exchange with the exhaust vapor stream 900 which is cooled as a result. The heated spent air stream 360 is sent to the thermal oxidizing section 500 of the thermal oxidation system 355. Heated combustion air stream 505 would also be sent to the thermal oxidizing section 500, while heated boiler feed water or oil stream 520 would be sent to the waste heat recovery section 515 thereby increasing the steam generation or hot oil generation efficiency.

A process waste water stream is passed through the first side of a primary heat exchanger 915. There can be one or more primary heat exchangers 915. The process waste water stream can optionally be compressed in a pump and/or compressor 920 before it is introduced into the primary heat exchanger 915.

The process waste water stream can be all or a portion of at least one of the phenolic water stream 385 from the phenolic water vessel 345 and the non-phenolic water stream 390 from the non-phenolic water vessel 350.

The first cooled exhaust vapor stream 910 is passed through the second side of the primary heat exchanger 915. Alternatively, in the absence of the secondary heat exchanger 905, exhaust vapor stream 900 is sent to the primary heat exchanger 915.

The first cooled exhaust vapor stream 910 entering the primary heat exchanger 915 has a temperature above the dew point. The heat exchange with the process waste water stream lowers the temperature of the first cooled exhaust vapor stream 910. In some cases, the temperature will be lowered to a temperature at or below the dew point which results in condensation of the moisture out of the first cooled exhaust vapor stream 910. The resulting second cooled exhaust vapor stream 925 can be sent to an exhaust stack and released to the atmosphere.

In other cases, the temperature will not be lowered sufficiently to condense water (any, most, or all) from the first cooled exhaust vapor stream 910. In this case, an optional third exchanger 930 can be used to lower the temperature of the second cooled exhaust vapor stream 925 to a temperature at or below the dew point leading to the formation of condensate. The cooling medium for the third heat exchanger can be cold/ambient air or cold water, for example.

The condensate is recovered and exits the primary heat exchanger 915 and/or the third heat exchanger as condensate stream 935. Condensate stream 935 can be sent to decomposition unit section 195 (FIG. 14), and/or the phenol recovery unit section 260 (FIG. 15).

The heated process waste water stream 940 is sent through throttling valve 945 to flash tank 950, which is at lower pressure (e.g., at a pressure of about 1-20 psig) than the primary heat exchanger 915. When the higher pressure heated process waste water stream 940 enters the lower pressure flash tank 950, it is flashed into a vapor stream 955 and a liquid stream 960. The vapor stream 955 and liquid stream 960 are sent to the thermal oxidizing section 500 of the thermal oxidation system 355. There can be an optional pump and/or compressor 965 on the line for the liquid stream 960.

Figure 18:
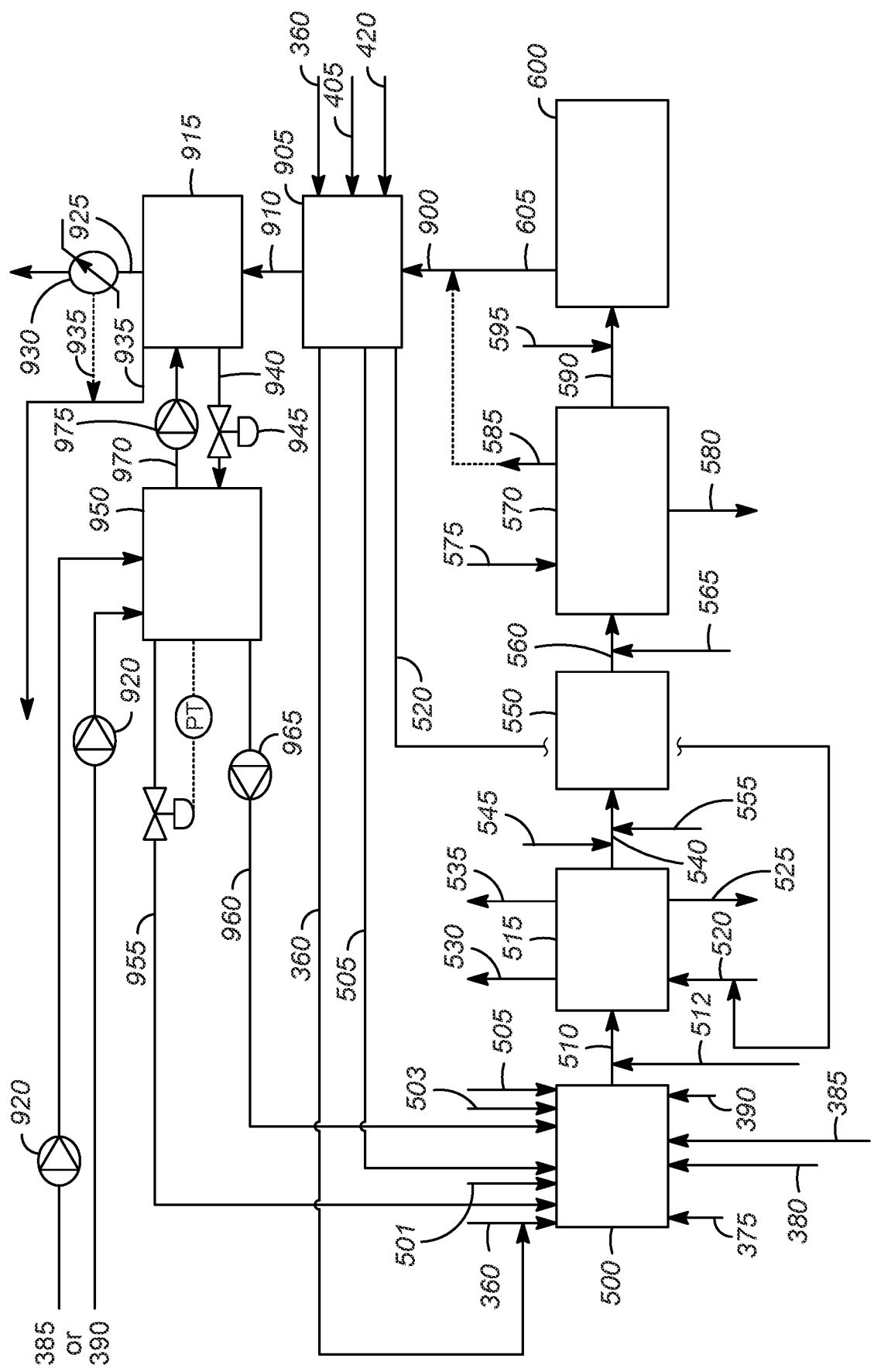
FIG. 18 is an illustration of one embodiment of the thermal oxidation system of FIG. 5 with improved energy recovery.

FIG. 18 illustrates the alternate arrangement in which the process waste water stream is initially sent to the flash tank 950, as described above with respect to FIG. 16.

Figure 19:
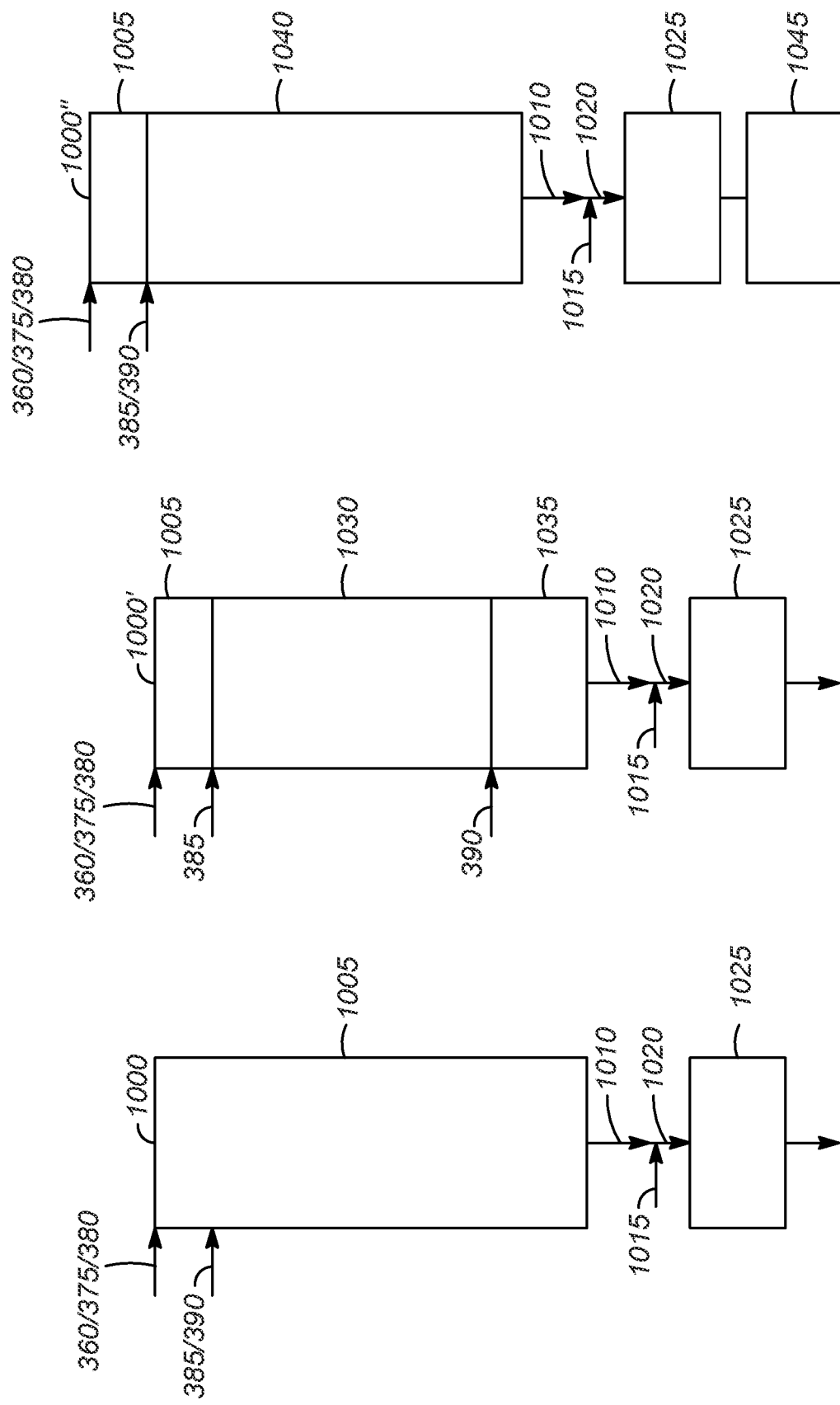
FIGS. 19A-C are illustrations of different embodiments of a thermal oxidizing section.

FIGS. 19A, 19B, and 19C illustrate different embodiments of a thermal oxidizing section and downstream conditioning, waste heat recovery and applying to 19C only, catalytic oxidation section. Other sections of the thermal oxidation system including the SOx recovery section and the optional NOx recovery section are not shown, as the objective is to illustrate the different temperature profiles of the thermal oxidation system and how this can lead to reduced utility requirements.

In FIG. 19A, the thermal oxidizing section 1000 comprises a single high temperature section 1005 having a minimum temperature needed to combust the compounds in the various streams (e.g., about 980° C.). Gaseous waste streams, (e.g., spent air stream 360 from the spent air knockout drum 330), hydrocarbon liquid streams (e.g., the mixed hydrocarbon waste stream 375 from the hydrocarbon buffer vessel 335, and/or the burner fuel stream 380 from the fuel gas knockout drum 340), phenolic waste water streams (e.g., the phenolic water stream 385 from the phenolic water vessel 345), and non-phenolic waste water streams (e.g. the non-phenolic water stream 390 from the non-phenolic water vessel 350) are all introduced at the first end of the high temperature section 1005. As discussed previously, these streams have different incoming temperatures, and some or all may need to be pre-heated.

The temperature of the high temperature section 1005 is maintained at or above the minimum temperature to combust the compounds in the various waste streams. The conditions are determined by the constituent auto ignition temperature (AIT). For example, cumene hydroperoxide has an AIT of 148° C., cumene has an AIT of 424° C., phenol has an AIT of 715° C., and benzene has an AIT of 560° C. The temperature for efficient oxidation is generally about 93° C. to about 260° C. above the AIT of the most difficult to oxidize organic compound in the waste stream. The destruction efficiency of volatile organic compounds (VOC) is a function of temperature, (turbulence) and residence time. For example, at 149° C. above AIT and 0.5 s residence time, the destruction efficiency is 95%. At 204° C. above AIT and 0.5 s residence time, the destruction efficiency is 98%. At 246° C. above AIT and 0.75 s residence time, the destruction efficiency is 99%. At 288° C. above AIT and 1.0 s residence time, the destruction efficiency is 99.9%. At 343° C. and 2.0 s residence time, the destruction efficiency is 99.99%.

The flue gas stream 1010 exiting the high temperature section 1005 is at or above the minimum temperature. If the sulfur salts are at too high a temperature (being above the sticky/tacky point and/or melting point), they can foul the waste heat recovery section 1025 due to condensation in the event that there are cold spots below the sticky/tacky point and/or melting point. Therefore, a quench stream 1015 of water, air, and/or recycled flue gas is used to reduce the temperature of the flue gas stream 1010 to a temperature below the temperature that the salts in the flue gas condense (e.g., less than about 704° C.-720° C.). The cooled flue gas stream 1020 is then sent to the waste heat recovery section 1025 and on to the rest of the thermal oxidation system.

In FIG. 19B, the thermal oxidizing section 1000' includes a high temperature section 1005, a medium temperature section 1030, and a low temperature section 1035.

Gaseous waste streams, (e.g., spent air stream 360 from the spent air knockout drum 330) and hydrocarbon liquid streams (e.g., the mixed hydrocarbon waste stream 375 from the hydrocarbon buffer vessel 335, and/or the burner fuel stream 380 from the fuel gas knockout drum 340) are introduced at the first end of the high temperature section 1005. The high temperature section 1005 has the minimum temperature to combust the compounds in the gaseous waste streams and hydrocarbon liquid streams (e.g., about 980° C.).

The phenolic waste water streams (e.g., the phenolic water stream 385 from the phenolic water vessel 345) are introduced at the second end of the high temperature section 1005. The phenolic waste water streams reduce the temperature of the flue gas, and the medium temperature section 1030 has a lower temperature than the high temperature section 1005. The medium temperature section 1030 has a minimum temperature to ensure destruction of the phenolic compounds (e.g., about 900° C.). The medium temperature section 1030 is maintained at or above the minimum temperature.

The non-phenolic waste water streams (e.g. the non-phenolic water stream 390 from the non-phenolic water vessel 350) are introduced at the second end of the medium temperature section 1030 which reduces the temperature of the flue gas further. The low temperature section 1040 has a minimum temperature for combustion of the non-phenolic compounds (e.g., of about 788° C.). The low temperature section 1035 is maintained at or above the minimum temperature.

The flue gas stream 1010 exiting the low temperature section 1035 is at the minimum temperature of the low temperature section 1035 (e.g., about 788° C.). A quench stream 1015 of water, air, and/or recycled flue gas is used to reduce the temperature of the flue gas stream 1010 to a temperature below the temperature that the salts in the flue gas condense (e.g., less than about 704-720° C.). The cooled flue gas stream 1020 is then sent to the waste heat recovery section 1025 and on to the rest of the thermal oxidation system.

In FIG. 19C, the thermal oxidizing section 1000" includes a high temperature section 1005 and a low temperature section 1040. In this embodiment, the gaseous waste streams, (e.g., spent air stream 360 from the spent air knockout drum 330), hydrocarbon liquid streams (e.g., the mixed hydrocarbon waste stream 375 from the hydrocarbon buffer vessel 335, and/or the burner fuel stream 380 from the fuel gas knockout drum 340) are introduced at the first end of the high temperature section 1005, which is maintained at a temperature above the minimum needed to combust the components in the gaseous waste streams and the liquid hydrocarbon streams (e.g., about 980° C.).

The phenolic waste water streams (e.g., the phenolic water stream 385 from the phenolic water vessel 345), and non-phenolic waste water streams (e.g. the non-phenolic water stream 390 from the non-phenolic water vessel 350) are introduced at the second end of the high temperature section 1005. The temperature of the low temperature section 1040 is lower temperature than the high temperature section 1005, and it depends on the amounts of the phenolic and non-phenolic streams. The low temperature section 1040 does not sufficiently destroy the phenolic and/or benzene compounds to comply with most environmental limits.

A quench stream 1015 of water or air is used to reduce the temperature of the flue gas stream 1010 to a temperature below the temperature that the salts in the flue gas condense (e.g., less than about 704-720° C.), if needed. In some embodiments, the temperature of the low temperature section 1040 will be below the temperature that the salts in the flue gas condense, and no quench will be required. The cooled flue gas stream 1020 is then sent to the waste heat recovery section 1025.

Figure 20:
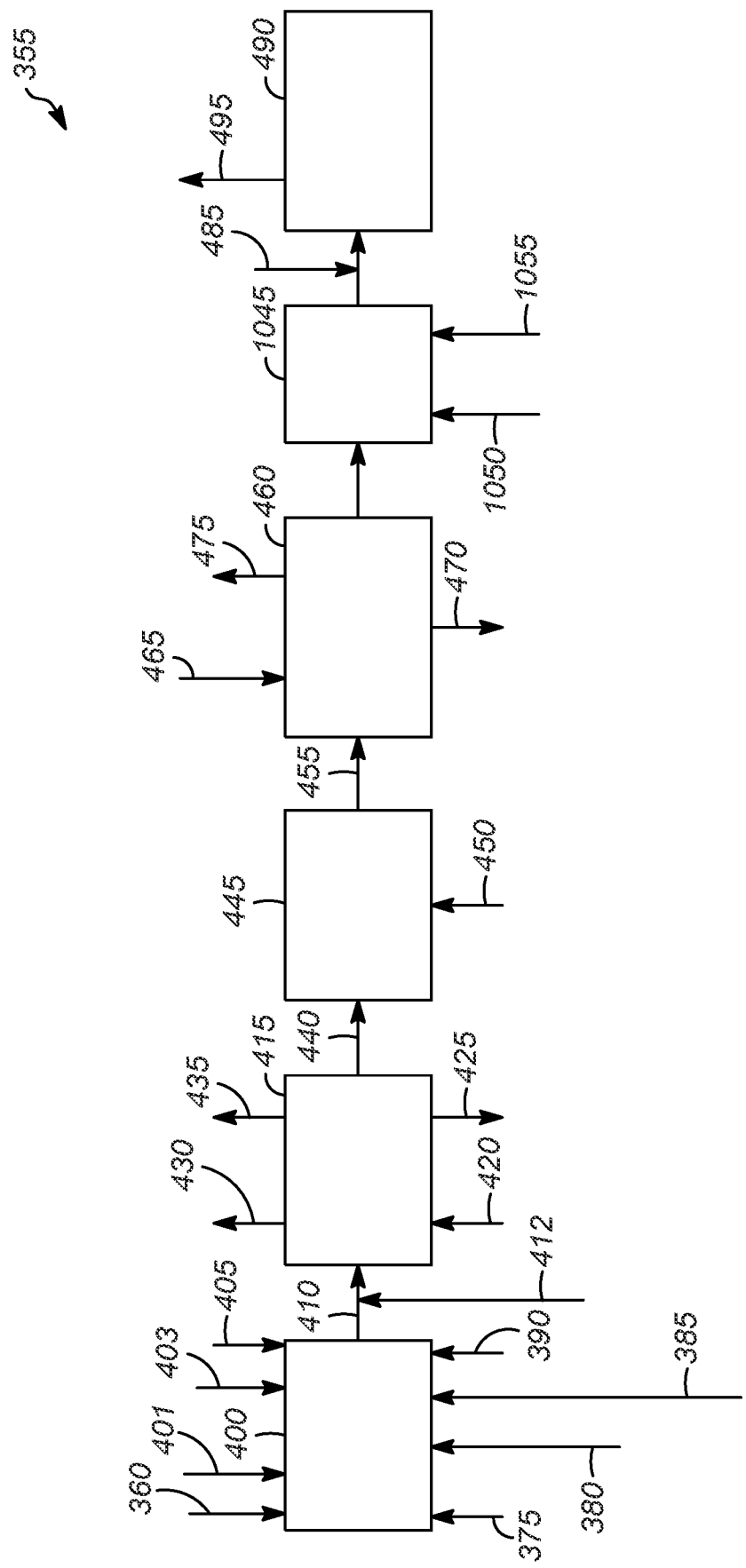
FIG. 20 is an illustration of another embodiment of the thermal oxidation system of FIG. 4.
Figure 21:
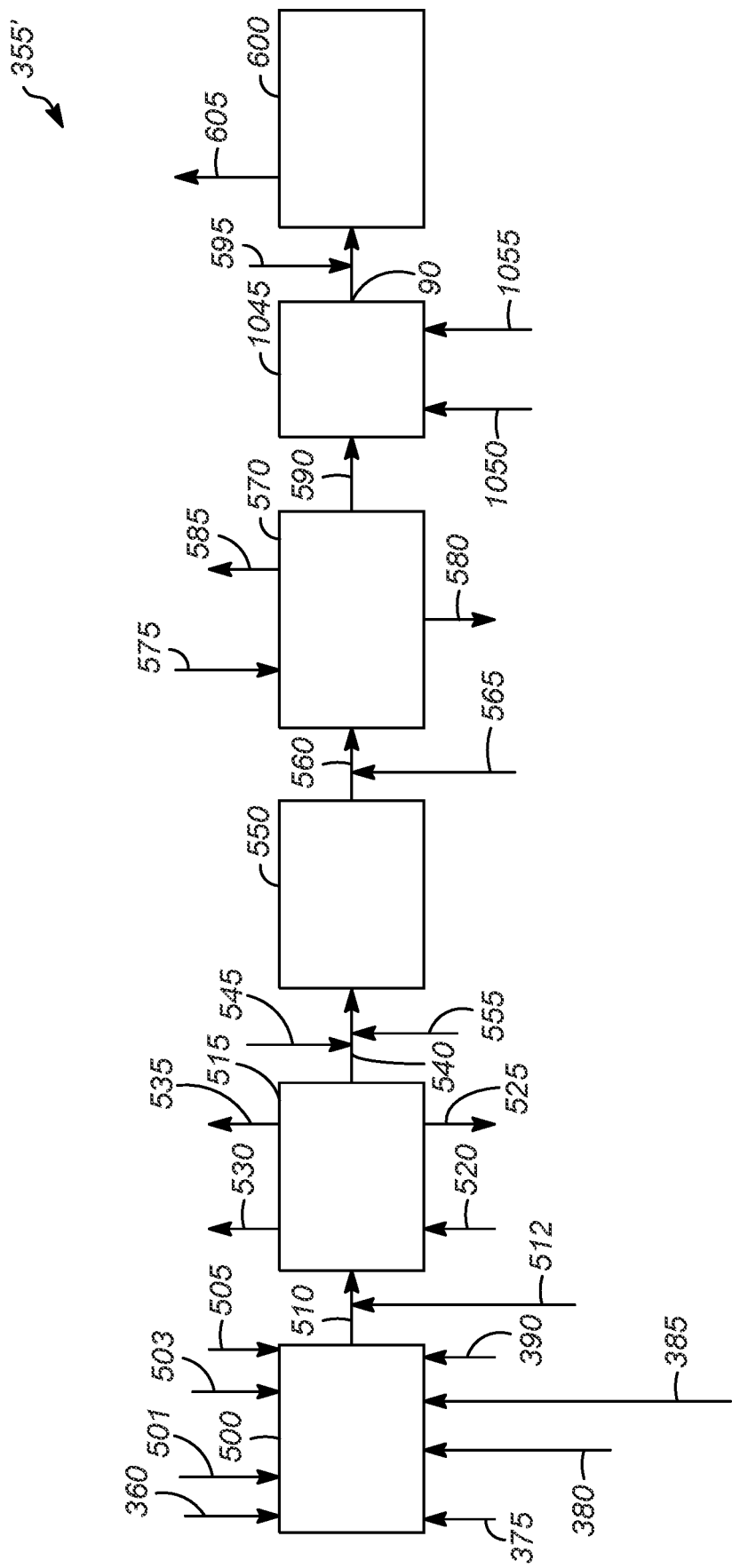
FIG. 21 is an illustration of another embodiment of the thermal oxidation system of FIG. 5.

A catalytic oxidation section 1045 completes the destruction of the phenolic and/or benzene compounds. The catalytic oxidizer is positioned after the SOx removal section and before the NOx removal section (if present) as shown in FIGS. 20-21. It is typically operated at a temperature in the range of about 200-400° C.

FIG. 20 illustrates another embodiment of the thermal oxidation system of FIG. 4 incorporating the catalytic oxidation section 1045. The catalytic oxidation section 1045 is positioned between the SOx removal section 460, and the NOx removal section 490. Combustion air 1050 and fuel 1055 are introduced into the catalytic oxidation section 1045, if needed. The quench stream 1015 at the exit of the thermal oxidizing section is shown as well.

FIG. 21 illustrates another embodiment of the thermal oxidation system of FIG. 5 incorporating the catalytic oxidation section 1045. The catalytic oxidation section 1045 is located after the SOx removal section comprising the SOx reaction section 550 and filtration section 570, and before the optional NOx removal section 600. The catalyst for the catalytic oxidizing section is a base metal oxide (e.g., Ti, V, Cr, and the like) and/or precious metal (e.g., Pt, Pd, and the like) on a carrier material (e.g., alumina, silica and the like). The substrate can be in the form of pellets or a honeycomb, for example. The average lifetime of the catalyst is about 30,000 to 40,000 hours.

Combustion air 1050 and fuel 1055 are introduced into the catalytic oxidation 1045 as needed. The quench stream 101 at the exit of the thermal oxidizing section is shown as well.

EXAMPLE

Table 1 is a computer simulation illustrating the effect of the different thermal oxidizing sections and catalytic oxidizing sections shown in FIGS. 19A-C. All three embodiments produce the desired emission targets of 10 mg/Nm$^3$ of non-methane hydrocarbons, 1 mg/Nm$^3$ of benzene, and 5 mg/Nm$^3$ of phenol. However, the amount of make-up fuel gas, combustion air, and quench water make-up needed vary significantly. The arrangement having staged introduction of components and the catalytic oxidizing section required about half the amount of fuel gas and combustion air as the configuration without staging, while the staged arrangement without the catalytic oxidizing section is between the two. In addition, the use of staged introduction of components substantially reduced the amount of quench water make-up. The amount of steam produced is less in the two configurations having staged introduction of components.

The arrangement of FIG. 19A results in the removal of 99.99% of the benzene in the gas and liquid waste streams and 99.9% of the phenol in the gas and liquid waste streams in the high temperature section 1005.

The arrangement of FIG. 19B results in the removal of 99.99% of the benzene in the gas waste streams and 99.9% of the phenol in the gas waste streams in the high temperature section 1005. 99.99% of the benzene in the liquid waste streams and 96% of the phenol in the liquid waste streams are removed in the medium temperature section 1030.

The arrangement of FIG. 19C results in the removal of 99.99% of the benzene in the gas waste streams and 99.9% of the phenol in the gas waste streams in the high temperature section 1005. 30% of the benzene in the liquid waste streams and 10% of the phenol in the liquid waste streams are removed in the low temperature section 1040. The catalytic oxidation section 1045 removes 90% of the residual benzene in the flue gas and 90% of the residual phenol in the flue gas.

TABLE 1

|  | FIG. 19A (no staging) | FIG. 19B (staging) | FIG. 19C (staging + CatOx) |
|---|---|---|---|
| Make-up fuel gas (lb/hr) | 8,748 | 5,530 | 3,937 |
| Combustion air (lb/hr) | 203,408 | 134,879 | 100,157 |
| Quench water make-up (lb/hr) | 35,500 | 7,650 | 0 |
| Flue gas flow rate (lb/hr) | 393,201 | 293,604 | 249,640 |
| Steam* production (lb/hr) | 95,290 | 68,883 | 49,628 |
| DRE benzene & phenol | | | |
| In high temperature TO section | Benzene: 99.99% (gas & liquid waste) Phenol: 99.9% (gas & liquid waste) | Benzene: 99.99% (gas waste) Phenol: 99.9% (gas waste) Benzene: 99.9% (liquid waste) Phenol: 96% (liquid waste) | Benzene: 99.99% (gas waste) Phenol: 99.9% (gas waste) |
| In medium temperature TO section | NA | | NA |
| In low temperature TO section | NA | NA | Benzene: 30% (liquid waste) Phenol: 10% (liquid waste) |
| In CatOx section | NA | NA | Benzene: 90% (flue gas)*** Phenol: 90% (flue gas)*** |
| Emission target @ 3% O2, dry basis (mg/Nm$^3$) | NMHC** = 10 Benzene = 1 Phenol = 5 | NMEIC** = 10 Benzene = 1 Phenol = 5 | NMEIC** = 10 Benzene = 1 Phenol = 5 |

*MP steam of 220 psi(g)
**NMEIC = non methane hydrocarbon
***% removal of residual phenol and benzene Any of the above lines, conduits, units, devices, vessels, surrounding environments, zones or similar may be equipped with one or more monitoring components including sensors, measurement devices, data capture devices or data transmission devices. Signals, process or status measurements, and data from monitoring components may be used to monitor conditions in, around, and on process equipment. Signals, measurements, and/or data generated or recorded by monitoring components may be collected, processed, and/or transmitted through one or more networks or connections that may be private or public, general or specific, direct or indirect, wired or wireless, encrypted or not encrypted, and/or combination(s) thereof; the specification is not intended to be limiting in this respect.

Signals, measurements, and/or data generated or recorded by monitoring components may be transmitted to one or more computing devices or systems. Computing devices or systems may include at least one processor and memory storing computer-readable instructions that, when executed by the at least one processor, cause the one or more computing devices to perform a process that may include one or more steps. For example, the one or more computing devices may be configured to receive, from one or more monitoring component, data related to at least one piece of equipment associated with the process. The one or more computing devices or systems may be configured to analyze the data. Based on analyzing the data, the one or more computing devices or systems may be configured to determine one or more recommended adjustments to one or more parameters of one or more processes described herein. The one or more computing devices or systems may be configured to transmit encrypted or unencrypted data that includes the one or more recommended adjustments to the one or more parameters of the one or more processes described herein.

It should be appreciated and understood by those of ordinary skill in the art that various other components such as valves, pumps, filters, coolers, etc. were not shown in the drawings as it is believed that the specifics of same are well within the knowledge of those of ordinary skill in the art and a description of same is not necessary for practicing or understanding the embodiments of the present invention.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

As used herein, the terms "unit," "zone," and "section" can refer to an area including one or more equipment items as appropriate for the type of unit, zone, or section and/or one or more sub-zones or sub-sections. Equipment items can include, but are not limited to, one or more reactors or reactor vessels, separation vessels, adsorbent chamber or chambers, distillation towers, heaters, exchangers, pipes, pumps, compressors, and controllers. Additionally, an equipment item, such as a reactor, dryer, adsorbent chamber or vessel, can further include one or more sections, sub-sections, zones, or sub-zones.

SPECIFIC EMBODIMENTS

While the following is described in conjunction with specific embodiments, it will be understood that this description is intended to illustrate and not limit the scope of the preceding description and the appended claims.

A first embodiment of the invention is a process for producing phenol comprising oxidizing a fresh cumene feed stream in an oxidation unit section to form an oxidation product stream comprising cumene hydroperoxide (CHP), dimethylphenylcarbinol (DMPC), and cumene, and at least one of an oxidation waste water stream, an oxidation spent air stream, and a decanter vent stream; concentrating the oxidation product stream in a CHP concentration unit section to form a concentrated CHP stream and a concentration vent gas stream; decomposing the concentrated CHP stream in a decomposition unit section using a decomposition acid to form an acidic crude product stream comprising phenol, acetone, cumene, and AMS; neutralizing the acidic crude product with a neutralization agent in a neutralization unit section to form a neutralized crude product stream; fractionating the neutralized crude product stream in an acetone-phenol fractionation unit section into a fractionation cumene-AMS-phenol stream, and at least one of a fractionation phenolic water stream, a fractionation organic product stream, a fractionation waste water stream, and a fractionation hydrocarbon vent gas stream; separating the fractionation cumene-AMS-phenol stream in a phenol recovery unit section into a cumene-AMS feed stream, and at least one of a recycled sprung phenol stream comprising phenol and cumene, and a phenolic waste water stream; hydrogenating the cumene-AMS feed stream in an AMS hydrogenation unit section to form a MSHP recycled cumene stream; at least one of introducing at least one of the fractionation organic product stream from the fractionation unit section, a fuel gas knockout drum hydrocarbon liquid stream from a fuel gas knockout drum, and a spent air knockout drum liquid stream from a spent air knockout drum into a hydrocarbon buffer vessel; introducing at least one of an AMS hydrogen vent gas stream from the AMS hydrogenation unit section, a hydrocarbon buffer vessel vent gas stream from the hydrocarbon buffer vessel, a phenolic vent gas stream from a phenolic water vessel, and a non-phenolic vent gas stream from a non-phenolic water vessel into the fuel gas knockout drum; introducing at least one of the fractionation waste water stream the acetone-phenol fractionation unit section, the phenolic waste water stream from the phenol recovery unit section, and a skimmed water phase from the hydrocarbon buffer vessel into a phenolic water vessel; introducing at least one of the oxidation waste water stream from the oxidation unit section and a benzene column water stream from a cumene production unit into a non-phenolic water vessel; and thermally oxidizing one or more of a mixed hydrocarbon waste stream from the hydrocarbon buffer vessel, a burner fuel gas stream from the fuel gas knockout drum, a phenolic water stream from the phenolic water vessel, and a non-phenolic water stream from the non-phenolic water vessel in a thermal oxidation system. An embodiment of the invention is one, any or all of prior embodiments in this paragraph up through the first embodiment in this paragraph wherein thermally oxidizing the one or more of the mixed hydrocarbon waste stream from the hydrocarbon buffer vessel, the burner fuel gas stream from the fuel gas knockout drum, the phenolic water stream from the phenolic water vessel, and the non-phenolic water stream from the non-phenolic water vessel comprises thermally oxidizing the one or more of the mixed hydrocarbon waste stream from the hydrocarbon buffer vessel, the burner fuel gas stream from the fuel gas knockout drum, the phenolic water stream from the phenolic water vessel, the non-phenolic water stream from the non-phenolic water vessel in a thermal oxidizing section forming a flue gas consisting essentially of at least one of $H_2O$, $CO_2$, $N_2$, $O_2$, HCl, $Cl_2$, $Na_2SO_4$, $Na_2CO_3$, SOx, and NOx; recovering waste heat from the flue gas in a waste heat recovery section; optionally quenching the flue gas in a quench section after recovering the waste heat to form a quenched flue gas consisting essentially of at least one of $H_2O$, $CO_2$, $N_2$, $O_2$, HCl, $Cl_2$, $Na_2SO_4$, $Na_2CO_3$, SOx, and NOx; optionally removing at least one of $Na_2SO_4$, $Na_2CO_3$, SOx, HCl, and $Cl_2$ from the flue gas or the quenched flue gas in a SOx removal section to form a de-SOx outlet flue gas consisting essentially of at least one of $H_2O$, $CO_2$, $N_2$, $O_2$, NOx, wherein removing the SOx from the flue gas comprises contacting a caustic solution or an $NH_3$ based solution with the quenched flue gas in a scrubbing section to form the de-SOx outlet flue gas and a liquid effluent comprising at least one of $H_2O$, $Na_2SO_3$, $Na_2SO_4$, $NaHSO_3$, $Na_2CO_3$, NaCl, $(NH_4)_2SO_4$, and $NH_4Cl$; or reacting the flue gas with a reactant in an SOx reaction section to form a reaction section flue gas consisting essentially of at least one of $H_2O$, $CO_2$, $N_2$, $O_2$, NaCl, $Na_2CO_3$, $Na_2SO_4$, $NaNO_3$, $CaCl_2$, $CaSO_4$, $CaCO_3$, $Ca(NO_3)_2$, $MgCl_2$, $MgCO_3$, $MgSO_4$, $Mg(NO_3)_2$, $Cl_2$, and NOx wherein the reactant comprises $NaHCO_3$, $NaHCO_3 \cdot Na_2CO_3 \cdot 2(H_2O)$, $CaCO_3$, $Ca(OH)_2$, and $Mg(OH)_2$; and optionally filtering the reaction section flue gas in an optional filter section to remove at least one of NaCl, $Na_2CO_3$, $Na_2SO_4$, $NaNO_3$, $CaCl_2$, $CaSO_4$, $CaCO_3$, $Ca(NO_3)_2$, $MgCl_2$, $MgCO_3$, $MgSO_4$, and $Mg(NO_3)_2$ to form the de-SOx outlet flue gas; and optionally removing NOx from the flue gas in an optional NOx removal section, the quenched flue gas or the de-SOx outlet flue gas to form a de-NOx outlet flue gas consisting essentially of at least one of $H_2O$, $CO_2$, $N_2$, and $O_2$. An embodiment of the invention is one, any or all of prior embodiments in this paragraph up through the first embodiment in this paragraph further comprising providing the recovered waste heat to one or more of a vaporizer in the CHP concentration unit section, a dehydrator steam heat exchanger in the decomposition unit section, and a reboiler in the acetone-phenol fractionation unit section. An embodiment of the invention is one, any or all of prior embodiments in this paragraph up through the first embodiment in this paragraph wherein quenching the flue gas comprises quenching the flue gas with at least one of air, de-SOx outlet flue gas, de-NOx outlet flue gas, and water. An embodiment of the invention is one, any or all of prior embodiments in this paragraph up through the first embodiment in this paragraph wherein the water comprises a water stream from the non-phenolic water vessel or an outside water stream. An embodiment of the invention is one, any or all of prior embodiments in this paragraph up through the first embodiment in this paragraph further comprising introducing a water wash waste stream from the phenol recovery unit section and the phenolic waste water stream from the phenol recovery unit section into the phenolic water vessel. An embodiment of the invention is one, any or all of prior embodiments in this paragraph up through the first embodiment in this paragraph further comprising introducing at least one of the oxidation spent air stream from the oxidation unit section, the decanter vent stream from the oxidation unit section, and the fractionation hydrocarbon vent gas stream from the acetone-phenol fractionation unit section into a spent air knockout drum; optionally preheating a spent air stream from the spent air knockout drum; and thermally oxidizing the spent air stream from the spent air knockout drum in the thermal oxidation system. An embodiment of the invention is one, any or all of prior embodiments in this paragraph up through the first embodiment in this paragraph wherein oxidizing the fresh cumene feed stream in the oxidation unit section to form the oxidation product stream comprises passing the fresh cumene feed and an oxidation air feed stream to at least one oxidation reactor to form the oxidation product stream and an oxidation spent air stream; cooling the oxidation spent air stream in an oxidizer vent gas cooler before introducing the oxidation spent air stream into a spent air knockout drum, and forming a condensate stream; passing the condensate stream to a decanter vessel and forming the decanter vent stream, the oxidation waste water stream, and a decanter cumene recycle stream; washing the decanter cumene recycle stream with a recycle cumene wash water stream and a recycle cumene wash caustic stream in a cumene feed wash column to form a washed cumene stream and a recycle cumene wash water waste stream; passing the washed cumene stream to the oxidation reactors; passing the recycle cumene wash water waste stream to the non-phenolic water vessel; and optionally at least one of passing the MSHP recycle cumene stream from the AMS hydrogenation unit section to the cumene feed wash column and passing a concentration section recycle cumene stream from the CHP concentration unit section to the cumene feed wash column. An embodiment of the invention is one, any or all of prior embodiments in this paragraph up through the first embodiment in this paragraph further comprising at least one of; recycling a concentration section recycled cumene stream from the CHP concentration unit section to the oxidation unit section; recycling the concentration vent gas stream from the CHP concentration unit section to the oxidation unit section; recycling the recycled sprung phenol stream from the phenol recovery unit section to the neutralization unit section; and passing the oxidation waste water stream to a peroxide destruction section to convert peroxides in the oxidation waste water stream to at least one of alcohols, ketones, aldehydes, organic acids and water to form a peroxide-free oxidation waste water stream before introducing the peroxide-free oxidation waste water stream into the non-phenolic water vessel. An embodiment of the invention is one, any or all of prior embodiments in this paragraph up through the first embodiment in this paragraph further comprising reacting propylene and benzene in a cumene production zone to produce the cumene feed stream, and at least one of a cumene production unit hydrocarbon waste stream, a propane vent stream, a benzene drag stream, and a cumene production unit vent gas stream; and at least one of introducing the cumene production unit hydrocarbon waste stream into the hydrocarbon buffer vessel; introducing at least one of the propane vent stream and the benzene drag stream into the fuel gas knockout drum; and introducing the cumene production unit vent gas stream into the spent air knockout drum. An embodiment of the invention is one, any or all of prior embodiments in this paragraph up through the first embodiment in this paragraph further comprising preheating at least one of the phenolic water stream from the phenolic water vessel and the non-phenolic water stream from the non-phenolic water vessel before thermally oxidizing the at least one of the phenolic water stream and the non-phenolic water stream using at least one of the recovered waste heat from the thermal oxidation system and a low pressure steam stream from the cumene production unit. An embodiment of the invention is one, any or all of prior embodiments in this paragraph up through the first embodiment in this paragraph further comprising controlling a pressure in at least one of the hydrocarbon buffer vessel, the phenolic water vessel, and the non-phenolic water vessel in a push-pull system by introducing at least one of fuel gas, liquefied petroleum gas, and waste gas into the at least one of the hydrocarbon buffer vessel, the phenolic water vessel, and the non-phenolic water vessel; and sending excess at least one of the fuel gas, liquefied petroleum gas, and waste gas to the fuel gas knockout drum. An embodiment of the invention is one, any or all of prior embodiments in this paragraph up through the first embodiment in this paragraph wherein the phenolic water stream is atomized and injected into a burner flame or directly downstream of the calculated flame length in the thermal oxidizer section and wherein the non-phenolic water is injected at a position downstream of the calculated atomization and evaporation distance of the phenolic water stream. An embodiment of the invention is one, any or all of prior embodiments in this paragraph up through the first embodiment in this paragraph further comprising passing a process waste water stream though a first side of a primary heat exchanger, wherein the process waste water stream comprises all or a portion of at least one of the phenolic water stream and the non-phenolic water stream; passing an exhaust vapor stream from the thermal oxidation system through a second side of the primary heat exchanger, wherein the exhaust vapor stream comprises the exhaust stream or the de-NOx outlet flue gas stream; transferring heat from the exhaust vapor stream to the process water stream, cooling the exhaust vapor stream forming a cooled exhaust stream and heating the process waste water stream forming a heated process waste water stream; reducing a pressure of the heated process waste water stream; passing the reduced pressure heated process waste water stream to a flash tank having a pressure lower than a pressure in the primary heat exchanger, forming a vapor stream and a liquid stream; passing the vapor stream and the liquid stream to the thermal oxidizing section of the thermal oxidation system; and passing the cooled exhaust stream to an exhaust stack. An embodiment of the invention is one, any or all of prior embodiments in this paragraph up through the first embodiment in this paragraph further comprising passing a process stream through a first side of a secondary heat exchanger, wherein the process stream is at least one of a spent air stream from a spent air knockout drum, a combustion air stream, and a boiler feed water or oil stream; passing the exhaust vapor stream to a second side of the secondary heat exchanger before passing the exhaust vapor stream to the primary heat exchanger to reduce a temperature of the exhaust vapor stream and to heat the at least one process stream and form a second cooled exhaust vapor stream and at least one of a heated spent air stream, a heated combustion air stream, and a heated boiler feed water or oil stream; passing the second cooled exhaust vapor stream to the primary heat exchanger and wherein passing the exhaust vapor stream from the thermal oxidation system through the second side of the primary heat exchanger comprises passing the second cooled exhaust vapor stream through a second side of the primary heat exchanger; and at least one of passing the heated spent air stream to the thermal oxidizing section of the thermal oxidation system; passing the heated combustion air stream to the thermal oxidizing section of the thermal oxidation system; and passing the heated boiler feed water or oil stream to the waste heat recovery section. An embodiment of the invention is one, any or all of prior embodiments in this paragraph up through the first embodiment in this paragraph further comprising introducing the process waste water stream to the flash tank forming a liquid and a vapor before passing the process waste water stream to the primary heat exchanger; and compressing at least a portion of the liquid; wherein passing the process waste water stream through the first side of the primary heat exchanger comprises passing a portion of the compressed liquid from the flash tank to the primary heat exchanger; wherein reducing the pressure of the heated process waste water stream comprises reducing the pressure of the heated compressed liquid from the primary heat exchanger; and wherein passing the reduced pressure heated process waste water stream to the flash tank comprises passing the reduced pressure heated compressed liquid to the flash tank. An embodiment of the invention is one, any or all of prior embodiments in this paragraph up through the first embodiment in this paragraph wherein the exhaust vapor stream is cooled in the primary heat exchanger to a temperature at or below a dew point to condense water from the exhaust vapor stream, forming a first condensate stream. An embodiment of the invention is one, any or all of prior embodiments in this paragraph up through the first embodiment in this paragraph further comprising passing the first condensate stream to at least one of the phenol recovery unit section and the decomposition unit section. An embodiment of the invention is one, any or all of prior embodiments in this paragraph up through the first embodiment in this paragraph wherein the cooled exhaust vapor stream is passed to a third heat exchanger before being passed to the exhaust stack, and wherein the cooled exhaust vapor stream is further cooled in the third heat exchanger to a temperature at or below a dew point to condense water from the cooled exhaust vapor stream, forming a second condensate stream. An embodiment of the invention is one, any or all of prior embodiments in this paragraph up through the first embodiment in this paragraph further comprising passing the second condensate stream to at least one of the phenol recovery unit section and the decomposition unit section. An embodiment of the invention is one, any or all of prior embodiments in this paragraph up through the first embodiment in this paragraph further comprising compressing the process waste water stream before passing the process waste water stream to the primary heat exchanger. An embodiment of the invention is one, any or all of prior embodiments in this paragraph up through the first embodiment in this paragraph wherein the thermal oxidizing section comprises a high temperature section and wherein the mixed hydrocarbon waste stream from the hydrocarbon buffer vessel, the burner fuel gas stream from the fuel gas knockout drum, the phenolic water stream from the phenolic water vessel, and the non-phenolic water stream from the non-phenolic water vessel when present are introduced into the high temperature section and wherein the high temperature section has a minimum temperature for combustion of the mixed hydrocarbon waste stream from the hydrocarbon buffer vessel, and the burner fuel gas stream from the fuel gas knockout drum. An embodiment of the invention is one, any or all of prior embodiments in this paragraph up through the first embodiment in this paragraph wherein the thermal oxidizing section comprises a high temperature section, a medium temperature section, and a low temperature section, and wherein the mixed hydrocarbon waste stream from the hydrocarbon buffer vessel, and the burner fuel gas stream from the fuel gas knockout drum when present are introduced into a first end of the high temperature section, and wherein the phenolic water stream from the phenolic water vessel when present is introduced at a second end of the high temperature section, and wherein the non-phenolic water stream from the non-phenolic water vessel when present is introduced at the low temperature section, and wherein the high temperature section has a minimum temperature for combustion of the mixed hydrocarbon waste stream from the hydrocarbon buffer vessel, and the burner fuel gas stream from the fuel gas knockout drum, wherein the medium temperature section has a minimum temperature for combustion of phenolic compounds, and wherein the low temperature section has a temperature for combustion of non-phenolic compounds. An embodiment of the invention is one, any or all of prior embodiments in this paragraph up through the first embodiment in this paragraph wherein the thermal oxidizing section comprises a high temperature section and a low temperature section, and wherein the mixed hydrocarbon waste stream from the hydrocarbon buffer vessel, and the burner fuel gas stream from the fuel gas knockout drum when present are introduced into the high temperature section, and wherein the phenolic water stream from the phenolic water vessel and the non-phenolic water stream from the non-phenolic water vessel when present are introduced into the low temperature section, and wherein the high temperature section has a minimum temperature for combustion of the mixed hydrocarbon waste stream from the hydrocarbon buffer vessel, and the burner fuel gas stream from the fuel gas knockout drum, and wherein the low temperature section has a temperature for combustion of non-phenolic compounds and a portion of the phenolic compounds and; and further comprising oxidizing additional phenolic compounds and benzene in the presence of a catalyst in a catalytic oxidizing section positioned after the SOx removal section and before the optional NOx removal section. An embodiment of the invention is one, any or all of prior embodiments in this paragraph up through the first embodiment in this paragraph wherein the SOx removal section comprises the SOx reaction section and the optional filter section.

A second embodiment of the invention is a process for producing phenol comprising reacting propylene and benzene in a cumene production zone to produce a fresh cumene feed stream, and at least one of a cumene production unit hydrocarbon waste stream, a benzene column water stream, a propane vent stream, a benzene drag stream, and a cumene production unit vent gas stream; oxidizing the fresh cumene feed stream in an oxidation unit section to form an oxidation product stream comprising cumene hydroperoxide (CHIP), dimethylphenylcarbinol (DMPC), and cumene, and at least one of an oxidation waste water stream, an oxidation spent air stream, and a decanter vent stream; concentrating the oxidation product stream in a CHP concentration unit section to form a concentrated CHP stream and a concentration vent gas stream; decomposing the concentrated CHP stream in a decomposition unit section using a decomposition acid to form an acidic crude product stream comprising phenol, acetone, cumene, and AMS; neutralizing the acidic crude product with a neutralization agent in a neutralization unit section to form a neutralized crude product stream; fractionating the neutralized crude product stream in a acetone-phenol fractionation unit section into a fractionation cumene-AMS-phenol stream, and at least one of a fractionation phenolic water stream, a fractionation organic product stream, a fractionation waste water stream, and a fractionation hydrocarbon vent gas stream; separating the fractionation cumene-AMS-phenol stream in a phenol recovery unit section into a cumene-AMS feed stream, and at least one of a recycled sprung phenol stream comprising phenol and cumene, and a phenolic waste water stream; recycling the recycled sprung phenol stream to the neutralization unit section; hydrogenating the cumene-AMS feed stream in an AMS hydrogenation unit section to form a MSHP recycled cumene stream and an AMS hydrogen vent stream; at least one of introducing at least one of the fractionation organic product stream from the fractionation unit section, the cumene production unit hydrocarbon waste stream from the cumene production unit, a fuel gas knockout drum hydrocarbon liquid stream from a fuel gas knockout drum, and a spent air knockout drum liquid stream from a spent air knockout drum into a hydrocarbon buffer vessel; introducing at least one of the AMS hydrogen vent gas stream from the AMS hydrogenation unit section, the propane vent stream from the cumene production unit, the benzene drag stream from the cumene production unit, a hydrocarbon buffer vessel vent gas stream from the hydrocarbon buffer vessel, a phenolic vent gas stream from a phenolic water vessel, and a non-phenolic vent gas stream from a non-phenolic water vessel into the fuel gas knockout drum; introducing at least one of the fractionation waste water stream the acetone-phenol fractionation unit section, the phenolic waste water stream from the phenol recovery unit section, and a skimmed water phase from the hydrocarbon buffer vessel into the phenolic water vessel; introducing at least one of the oxidation waste water stream from the oxidation unit section and a benzene column water stream from the cumene production unit into the non-phenolic water vessel; thermally oxidizing one or more of a mixed hydrocarbon waste stream from the hydrocarbon buffer vessel, a burner fuel gas stream from the fuel gas knockout drum, a phenolic water stream from the phenolic water vessel, a non-phenolic water stream from the non-phenolic water vessel in a thermal oxidation system, comprising thermally oxidizing the one or more of the mixed hydrocarbon waste stream from the hydrocarbon buffer vessel, the burner fuel gas stream from the fuel gas knockout drum, the phenolic water stream from the phenolic water vessel, the non-phenolic water stream from the non-phenolic water vessel in a thermal oxidizing section forming a flue gas consisting essentially of at least one of $H_2O$, $CO_2$, $N_2$, O2, $Na_2SO_4$, $Na_2CO_3$, HCl, $Cl_2$, SOx, and NOx; recovering waste heat from the flue gas in a waste heat recovery section; optionally quenching the flue gas in a quench section after recovering the waste heat to form a quenched flue gas consisting essentially of at least one of $H_2O$, $CO_2$, $N_2$, $O_2$, $Na_2SO_4$, $Na_2CO_3$, HCl, $Cl_2$, SOx, and NOx; optionally removing at least one of $Na_2SO_4$, $Na_2CO_3$, SOx, HCl, and $Cl_2$ from the flue gas or the quenched flue gas in a SOx removal section to form a de-SOx outlet flue gas consisting essentially of at least one of $H_2O$, $CO_2$, $N_2$, $O_2$, NOx, wherein removing the SOx from the flue gas comprises contacting a caustic solution or an NH3 based solution with the quenched flue gas in a scrubbing section to form the de-SOx outlet flue gas and a liquid effluent comprising at least one of $H_2O$, $Na_2SO_3$, $Na_2SO_4$, $NaHSO_3$, $Na_2CO_3$, NaCl, $(NH_4)_2SO_4$, and $NH_4Cl$; or reacting the flue gas with a reactant in an SOx reaction section to form a reaction section flue gas consisting essentially of at least one of $H_2O$, $CO_2$, $N_2$, $O_2$, NaCl, $Na_2CO_3$, $Na_2SO_4$, $NaNO_3$, $CaCl_2$, $CaSO_4$, $CaCO_3$, $Ca(NO_3)2$, $MgCl_2$, $MgCO_3$, $MgSO_4$, $Mg(NO_3)_2$, $Cl_2$, and NOx wherein the reactant comprises $NaHCO_3$, $NaHCO_3 \cdot Na_2CO_3 \cdot 2(H_2O)$, $CaCO_3$, $Ca(OH)_2$, and $Mg(OH)_2$; and optionally filtering the reaction section flue gas in a filter section to remove at least one of NaCl, $Na_2CO_3$, $Na_2SO_4$, $NaNO_3$, $CaCl_2$, $CaSO_4$, $CaCO_3$, $Ca(NO_3)_2$, $MgCl_2$, $MgCO_3$, $MgSO_4$, and $Mg(NO_3)_2$ to form the de-SOx outlet flue gas; and optionally removing NOx from the flue gas, the quenched flue gas, or the de-SOx outlet flue gas to form de-NOx outlet flue gas consisting essentially of at least one of $H_2O$, $CO_2$, $N_2$, and $O_2$. An embodiment of the invention is one, any or all of prior embodiments in this paragraph up through the second embodiment in this paragraph further comprising introducing at least one of the oxidation spent air stream from the oxidation unit section, the decanter vent stream from the oxidation unit section, the fractionation hydrocarbon vent gas stream from the acetone-phenol fractionation unit section, and the cumene production unit vent gas stream from the cumene production unit into the spent air knockout drum; optionally preheating a spent air stream from the spent air knockout drum; and thermally oxidizing the spent air stream from the spent air knockout drum in the thermal oxidation system. An embodiment of the invention is one, any or all of prior embodiments in this paragraph up through the second embodiment in this paragraph further comprising providing the recovered waste heat to one or more of a vaporizer in the CHP concentration unit section, a dehydrator steam heat exchanger in the decomposition unit section, and a reboiler in the acetone-phenol fractionation unit section. An embodiment of the invention is one, any or all of prior embodiments in this paragraph up through the second embodiment in this paragraph further comprising at least one of introducing a water wash waste stream from the phenol recovery unit section and the phenolic waste water stream from the phenol recovery unit section into the phenolic water vessel; and introducing at least one of the oxidation spent air stream from the oxidation unit section, the decanter vent stream from the oxidation unit section, the concentration vent gas stream from the CHP concentration unit section, and the fractionation hydrocarbon vent gas stream from the acetone-phenol fractionation unit section into the spent air knockout drum. An embodiment of the invention is one, any or all of prior embodiments in this paragraph up through the second embodiment in this paragraph further comprising preheating at least one of the phenolic water stream from the phenolic water vessel and the non-phenolic water stream from the non-phenolic water vessel before thermally oxidizing the at least one of the spent air stream, the phenolic water stream and the non-phenolic water stream using at least one of the recovered waste heat from the thermal oxidation system and a low pressure steam stream from the cumene production unit.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

What is claimed is:
1. A process for producing phenol comprising:
oxidizing a fresh cumene feed stream in an oxidation unit section to form an oxidation product stream comprising cumene hydroperoxide (CHP), dimethylphenylcarbinol (DMPC), and cumene, and at least one of an oxidation waste water stream, an oxidation spent air stream, and a decanter vent stream;
concentrating the oxidation product stream in a CHP concentration unit section to form a concentrated CHP stream and a concentration vent gas stream;
decomposing the concentrated CHP stream in a decomposition unit section using a decomposition acid to form an acidic crude product stream comprising phenol, acetone, cumene, and AMS;
neutralizing the acidic crude product with a neutralization agent in a neutralization unit section to form a neutralized crude product stream;
fractionating the neutralized crude product stream in an acetone-phenol fractionation unit section into a fractionation cumene-AMS-phenol stream, and at least one of a fractionation phenolic water stream, a fractionation organic product stream, a fractionation waste water stream, and a fractionation hydrocarbon vent gas stream;
separating the fractionation cumene-AMS-phenol stream in a phenol recovery unit section into a cumene-AMS feed stream, and at least one of a recycled sprung phenol stream comprising phenol and cumene, and a phenolic waste water stream;
hydrogenating the cumene-AMS feed stream in an AMS hydrogenation unit section to form a MSHP recycled cumene stream;
at least one of:
    introducing at least one of the fractionation organic product stream from the fractionation unit section, a fuel gas knockout drum hydrocarbon liquid stream from a fuel gas knockout drum, and a spent air knockout drum liquid stream from a spent air knockout drum into a hydrocarbon buffer vessel;
    introducing at least one of an AMS hydrogen vent gas stream from the AMS hydrogenation unit section, a hydrocarbon buffer vessel vent gas stream from the hydrocarbon buffer vessel, a phenolic vent gas stream from a phenolic water vessel, and a non-phenolic vent gas stream from a non-phenolic water vessel into the fuel gas knockout drum;
    introducing at least one of: the fractionation waste water stream the acetone-phenol fractionation unit section, the phenolic waste water stream from the phenol recovery unit section, and a skimmed water phase from the hydrocarbon buffer vessel into a phenolic water vessel;
    introducing at least one of the oxidation waste water stream from the oxidation unit section and a benzene column water stream from a cumene production unit into a non-phenolic water vessel; and
thermally oxidizing one or more of: a mixed hydrocarbon waste stream from the hydrocarbon buffer vessel, a burner fuel gas stream from the fuel gas knockout drum, a phenolic water stream from the phenolic water vessel, and a non-phenolic water stream from the non-phenolic water vessel in a thermal oxidation system.

2. The process of claim 1 wherein thermally oxidizing the one or more of: the mixed hydrocarbon waste stream from the hydrocarbon buffer vessel, the burner fuel gas stream from the fuel gas knockout drum, the phenolic water stream from the phenolic water vessel, and the non-phenolic water stream from the non-phenolic water vessel comprises:
thermally oxidizing the one or more of: the mixed hydrocarbon waste stream from the hydrocarbon buffer vessel, the burner fuel gas stream from the fuel gas knockout drum, the phenolic water stream from the phenolic water vessel, the non-phenolic water stream from the non-phenolic water vessel in a thermal oxidizing section forming a flue gas consisting essentially of at least one of $H_2O$, $CO_2$, $N_2$, $O_2$, HCl, $Cl_2$, $Na_2SO_4$, $Na_2CO_3$, SOx, and NOx;
recovering waste heat from the flue gas in a waste heat recovery section;
optionally quenching the flue gas in a quench section after recovering the waste heat to form a quenched flue gas consisting essentially of at least one of $H_2O$, $CO_2$, $N_2$, $O_2$, HCl, $Cl_2$, $Na_2SO_4$, $Na_2CO_3$, SOx, and NOx;
optionally removing at least one of $Na_2SO_4$, $Na_2CO_3$, SOx, HCl, and $Cl_2$ from the flue gas or the quenched flue gas in a SOx removal section to form a de-SOx outlet flue gas consisting essentially of at least one of $H_2O$, $CO_2$, $N_2$, $O_2$, NOx, wherein removing the SOx from the flue gas comprises:
contacting a caustic solution or an $NH_3$ based solution with the quenched flue gas in a scrubbing section to form the de-SOx outlet flue gas and a liquid effluent comprising at least one of $H_2O$, $Na_2SO_3$, $Na_2SO_4$, $NaHSO_3$, $Na_2CO_3$, NaCl, $(NH_4)_2SO_4$, and $NH_4Cl$; or
reacting the flue gas with a reactant in an SOx reaction section to form a reaction section flue gas consisting essentially of at least one of $H_2O$, $CO_2$, $N_2$, $O_2$, NaCl, $Na_2CO_3$, $Na_2SO_4$, $NaNO_3$, $CaCl_2$), $CaSO_4$, $CaCO_3$, $Ca(NO_3)_2$, $MgCl_2$, $MgCO_3$, $MgSO_4$, $Mg(NO_3)_2$, $Cl_2$, and NOx wherein the reactant comprises $NaHCO_3$, $NaHCO_3 \cdot Na_2CO_3 \cdot 2(H_2O)$, $CaCO_3$, $Ca(OH)_2$, and $Mg(OH)_2$; and
optionally filtering the reaction section flue gas in an optional filter section to remove at least one of NaCl, $Na_2CO_3$, $Na_2SO_4$, $NaNO_3$, $CaCl_2$), $CaSO_4$, $CaCO_3$, $Ca(NO_3)_2$, $MgCl_2$, $MgCO_3$, $MgSO_4$, and $Mg(NO_3)_2$ to form the de-SOx outlet flue gas; and
optionally removing NOx from the flue gas in an optional NOx removal section, the quenched flue gas or the de-SOx outlet flue gas to form a de-NOx outlet flue gas consisting essentially of at least one of $H_2O$, $CO_2$, $N_2$, and $O_2$.

3. The process of claim 2 further comprising:
providing the recovered waste heat to one or more of: a vaporizer in the CHP concentration unit section, a dehydrator steam heat exchanger in the decomposition unit section, and a reboiler in the acetone-phenol fractionation unit section.

4. The process of claim 1 further comprising:
introducing at least one of: the oxidation spent air stream from the oxidation unit section, the decanter vent stream from the oxidation unit section, and the fractionation hydrocarbon vent gas stream from the acetone-phenol fractionation unit section into a spent air knockout drum;
optionally preheating a spent air stream from the spent air knockout drum; and
thermally oxidizing the spent air stream from the spent air knockout drum in the thermal oxidation system.

5. The process of claim 1 wherein oxidizing the fresh cumene feed stream in the oxidation unit section to form the oxidation product stream comprises:
passing the fresh cumene feed and an oxidation air feed stream to at least one oxidation reactor to form the oxidation product stream and an oxidation spent air stream;
cooling the oxidation spent air stream in an oxidizer vent gas cooler before introducing the oxidation spent air stream into a spent air knockout drum, and forming a condensate stream;
passing the condensate stream to a decanter vessel and forming the decanter vent stream, the oxidation waste water stream, and a decanter cumene recycle stream;
washing the decanter cumene recycle stream with a recycle cumene wash water stream and a recycle cumene wash caustic stream in a cumene feed wash column to form a washed cumene stream and a recycle cumene wash water waste stream;
passing the washed cumene stream to the oxidation reactors;
passing the recycle cumene wash water waste stream to the non-phenolic water vessel; and
optionally at least one of passing the MSHP recycle cumene stream from the AMS hydrogenation unit section to the cumene feed wash column and passing a concentration section recycle cumene stream from the CHP concentration unit section to the cumene feed wash column.

6. The process of claim 1 further comprising at least one of:
recycling a concentration section recycled cumene stream from the CHP concentration unit section to the oxidation unit section;
recycling the concentration vent gas stream from the CHP concentration unit section to the oxidation unit section;
recycling the recycled sprung phenol stream from the phenol recovery unit section to the neutralization unit section; and
passing the oxidation waste water stream to a peroxide destruction section to convert peroxides in the oxidation waste water stream to at least one of alcohols, ketones, aldehydes, organic acids and water to form a peroxide-free oxidation waste water stream before introducing the peroxide-free oxidation waste water stream into the non-phenolic water vessel.

7. The process of claim 1 further comprising:
reacting propylene and benzene in a cumene production zone to produce the cumene feed stream, and at least one of: a cumene production unit hydrocarbon waste stream, a propane vent stream, a benzene drag stream, and a cumene production unit vent gas stream; and
at least one of:
introducing the cumene production unit hydrocarbon waste stream into the hydrocarbon buffer vessel;
introducing at least one of: the propane vent stream and the benzene drag stream into the fuel gas knockout drum; and
introducing the cumene production unit vent gas stream into the spent air knockout drum.

8. The process of claim 2 further comprising:
preheating at least one of the phenolic water stream from the phenolic water vessel and the non-phenolic water stream from the non-phenolic water vessel before thermally oxidizing the at least one of the phenolic water stream and the non-phenolic water stream using at least one of the recovered waste heat from the thermal oxidation system and a low pressure steam stream from the cumene production unit.

9. The process of claim 1 further comprising:
controlling a pressure in at least one of the hydrocarbon buffer vessel, the phenolic water vessel, and the non-phenolic water vessel in a push-pull system by introducing at least one of fuel gas, liquefied petroleum gas, and waste gas into the at least one of the hydrocarbon buffer vessel, the phenolic water vessel, and the non-phenolic water vessel; and sending excess at least one of the fuel gas, liquefied petroleum gas, and waste gas to the fuel gas knockout drum.

10. The process of claim 1 wherein the phenolic water stream is atomized and injected into a burner flame or directly downstream of the calculated flame length in the thermal oxidizer section and wherein the non-phenolic water stream is injected at a position downstream of the calculated atomization and evaporation distance of the phenolic water stream.

11. The process of claim 2 further comprising:
passing a process waste water stream though a first side of a primary heat exchanger, wherein the process waste water stream comprises all or a portion of at least one of the phenolic water stream and the non-phenolic water stream;
passing an exhaust vapor stream from the thermal oxidation system through a second side of the primary heat exchanger, wherein the exhaust vapor stream comprises the exhaust stream or the de-NOx outlet flue gas stream;
transferring heat from the exhaust vapor stream to the process water stream, cooling the exhaust vapor stream forming a cooled exhaust stream and heating the process waste water stream forming a heated process waste water stream;
reducing a pressure of the heated process waste water stream;
passing the reduced pressure heated process waste water stream to a flash tank having a pressure lower than a pressure in the primary heat exchanger, forming a vapor stream and a liquid stream;
passing the vapor stream and the liquid stream to the thermal oxidizing section of the thermal oxidation system; and
passing the cooled exhaust stream to an exhaust stack.

12. The process of claim 11 further comprising:
passing a process stream through a first side of a secondary heat exchanger, wherein the process stream is at least one of a spent air stream from a spent air knockout drum, a combustion air stream, and a boiler feed water or oil stream;
passing the exhaust vapor stream to a second side of the secondary heat exchanger before passing the exhaust vapor stream to the primary heat exchanger to reduce a temperature of the exhaust vapor stream and to heat the at least one process stream and form a second cooled exhaust vapor stream and at least one of a heated spent air stream, a heated combustion air stream, and a heated boiler feed water or oil stream;
passing the second cooled exhaust vapor stream to the primary heat exchanger and wherein passing the exhaust vapor stream from the thermal oxidation system through the second side of the primary heat exchanger comprises passing the second cooled exhaust vapor stream through a second side of the primary heat exchanger; and
at least one of:
passing the heated spent air stream to the thermal oxidizing section of the thermal oxidation system;
passing the heated combustion air stream to the thermal oxidizing section of the thermal oxidation system; and
passing the heated boiler feed water or oil stream to the waste heat recovery section.

13. The process of claim 11 further comprising:
introducing the process waste water stream to the flash tank forming a liquid and a vapor before passing the process waste water stream to the primary heat exchanger; and
compressing at least a portion of the liquid;
wherein passing the process waste water stream through the first side of the primary heat exchanger comprises passing a portion of the compressed liquid from the flash tank to the primary heat exchanger;
wherein reducing the pressure of the heated process waste water stream comprises reducing the pressure of the heated compressed liquid from the primary heat exchanger; and
wherein passing the reduced pressure heated process waste water stream to the flash tank comprises passing the reduced pressure heated compressed liquid to the flash tank.

14. The process of claim 11 wherein the exhaust vapor stream is cooled in the primary heat exchanger to a temperature at or below a dew point to condense water from the exhaust vapor stream, forming a first condensate stream.

15. The process of claim 11 further comprising:
passing the first condensate stream to at least one of the phenol recovery unit section and the decomposition unit section.

16. The process of claim 11 wherein the cooled exhaust vapor stream is passed to a third heat exchanger before being passed to the exhaust stack, and wherein the cooled exhaust vapor stream is further cooled in the third heat exchanger to a temperature at or below a dew point to condense water from the cooled exhaust vapor stream, forming a second condensate stream; and
optionally passing the second condensate stream to at least one of the phenol recovery unit section and the decomposition unit section.

17. The process of claim 11 further comprising:
compressing the process waste water stream before passing the process waste water stream to the primary heat exchanger.

18. The process of claim 2 wherein the thermal oxidizing section comprises a high temperature section and wherein the mixed hydrocarbon waste stream from the hydrocarbon buffer vessel, the burner fuel gas stream from the fuel gas knockout drum, the phenolic water stream from the phenolic water vessel, and the non-phenolic water stream from the non-phenolic water vessel when present are introduced into the high temperature section and wherein the high temperature section has a minimum temperature for combustion of the mixed hydrocarbon waste stream from the hydrocarbon buffer vessel, and the burner fuel gas stream from the fuel gas knockout drum.

19. The process of claim 2 wherein the thermal oxidizing section comprises a high temperature section, a medium temperature section, and a low temperature section, and wherein the mixed hydrocarbon waste stream from the hydrocarbon buffer vessel, and the burner fuel gas stream from the fuel gas knockout drum when present are introduced into a first end of the high temperature section, and wherein the phenolic water stream from the phenolic water vessel when present is introduced at a second end of the high temperature section, and wherein the non-phenolic water stream from the non-phenolic water vessel when present is introduced at the low temperature section, and wherein the high temperature section has a minimum temperature for combustion of the mixed hydrocarbon waste stream from the hydrocarbon buffer vessel, and the burner fuel gas stream from the fuel gas knockout drum, wherein the medium temperature section has a minimum temperature for combustion of phenolic compounds, and wherein the low temperature section has a temperature for combustion of non-phenolic compounds.

20. The process of claim 2 wherein the thermal oxidizing section comprises a high temperature section and a low temperature section, and wherein the mixed hydrocarbon waste stream from the hydrocarbon buffer vessel, and the burner fuel gas stream from the fuel gas knockout drum when present are introduced into the high temperature section, and wherein the phenolic water stream from the phenolic water vessel and the non-phenolic water stream from the non-phenolic water vessel when present are introduced into the low temperature section, and wherein the high temperature section has a minimum temperature for combustion of the mixed hydrocarbon waste stream from the hydrocarbon buffer vessel, and the burner fuel gas stream from the fuel gas knockout drum, and wherein the low temperature section has a temperature for combustion of non-phenolic compounds and a portion of the phenolic compounds and; and further comprising:
oxidizing additional phenolic compounds and benzene in the presence of a catalyst in a catalytic oxidizing section positioned after the SOx removal section and before the optional NOx removal section.

* * * * *

UNITED STATES PATENT AND TRADEMARK OFFICE
CERTIFICATE OF CORRECTION

| | | |
|---|---|---|
| PATENT NO. | : 11,780,795 B2 | Page 1 of 1 |
| APPLICATION NO. | : 17/361690 | |
| DATED | : October 10, 2023 | |
| INVENTOR(S) | : Jan De Ren et al. | |

It is certified that error appears in the above-identified patent and that said Letters Patent is hereby corrected as shown below:

In the Claims

Claim 11, Column 39 Line 12 should read:
"...passing a process waste water stream through a first side of..."

Signed and Sealed this
Second Day of July, 2024

Katherine Kelly Vidal
Director of the United States Patent and Trademark Office